(12) United States Patent
Benita et al.

(10) Patent No.: US 9,421,173 B2
(45) Date of Patent: Aug. 23, 2016

(54) NANO DELIVERY SYSTEMS FOR SIRNA

(71) Applicant: YISSUM RESEARCH DEVELOPMENT COMPANY OF THE HEBREW UNIVERSITY OF JERUSALEM LTD., Jerusalem (IL)

(72) Inventors: Simon Benita, Tel Aviv (IL); Orit Amsalem, Jerusalem (IL); Taher Nassar, Kfar Turaan (IL)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 14/345,154
(22) PCT Filed: Sep. 20, 2012
(86) PCT No.: PCT/IL2012/050382
  § 371 (c)(1),
  (2) Date: Mar. 14, 2014
(87) PCT Pub. No.: WO2013/042125
  PCT Pub. Date: Mar. 28, 2013

(65) Prior Publication Data
  US 2015/0037427 A1    Feb. 5, 2015

Related U.S. Application Data

(60) Provisional application No. 61/537,241, filed on Sep. 21, 2011.

(51) Int. Cl.
  *A61K 9/00* (2006.01)
  *A61K 9/127* (2006.01)
  (Continued)

(52) U.S. Cl.
  CPC ........... *A61K 9/5153* (2013.01); *A61K 9/0019* (2013.01); *A61K 9/1271* (2013.01);
  (Continued)

(58) Field of Classification Search
  CPC ............... A61K 31/713; A61K 47/48869; A61K 9/0019; A61K 9/1271; A61K 9/1272; A61K 9/5146; A61K 9/5153; A61K 9/5169; A61K 9/5192; C12N 15/1138; C12N 15/88; C12N 2310/14; C12N 2320/52; C12N 2810/859
  See application file for complete search history.

(56) References Cited

U.S. PATENT DOCUMENTS

| | | | |
|---|---|---|---|
| 2003/0082237 A1* | 5/2003 | Cha | A61K 47/48861 424/490 |
| 2004/0204377 A1* | 10/2004 | Rana | 514/44 |

(Continued)

FOREIGN PATENT DOCUMENTS

| | | |
|---|---|---|
| JP | 2007-099631 A | 4/2007 |
| WO | 2007/029361 A1 | 3/2007 |

(Continued)

OTHER PUBLICATIONS

Beck-Broichsitter, Moritz et al., "Characterization of novel spray-dried polymeric particles for controlled pulmonary drug delivery," Journal of Controlled Release, 158, 329-335, 2012.

(Continued)

*Primary Examiner* — Aradhana Sasan
(74) *Attorney, Agent, or Firm* — Oliff PLC

(57) ABSTRACT

The present invention makes use of a unique methodology of double nano-encapsulation for protecting and controlling the release of active agents, either hydrophobic or hydrophilic, from stable nanoparticles of opposite characteristics. The protection of the active agent was achieved by loading the agent to be protected, into nanocarriers, which were subsequently encapsulated into sub-micron nanoparticles. The sub-micron nanoparticles formation has been successfully achieved by the use of novel nano spray techniques.

29 Claims, 42 Drawing Sheets

(51) Int. Cl.
  A61K 9/51   (2006.01)
  A61K 31/713   (2006.01)
  A61K 47/48   (2006.01)
  C12N 15/88   (2006.01)
  C12N 15/113   (2010.01)
(52) U.S. Cl.
  CPC ............ *A61K9/1272* (2013.01); *A61K 9/5146* (2013.01); *A61K 9/5169* (2013.01); *A61K 9/5192* (2013.01); *A61K 31/713* (2013.01); *A61K 47/48869* (2013.01); *C12N 15/1138* (2013.01); *C12N 15/88* (2013.01); *C12N 2310/14* (2013.01); *C12N 2320/52* (2013.01); *C12N 2810/859* (2013.01)

(56) References Cited

U.S. PATENT DOCUMENTS

| | | | |
|---|---|---|---|
| 2005/0142567 A1* | 6/2005 | Su | G01N 21/6428 435/6.11 |
| 2005/0271732 A1* | 12/2005 | Seeney | A61K 9/0009 424/489 |
| 2009/0169637 A1 | 7/2009 | Makino et al. | |
| 2009/0263331 A1* | 10/2009 | Wu et al. | 424/9.323 |
| 2009/0312402 A1 | 12/2009 | Contag et al. | |
| 2010/0310670 A1 | 12/2010 | Okada et al. | |
| 2011/0256059 A1 | 10/2011 | Sanchez Barreiro et al. | |

FOREIGN PATENT DOCUMENTS

| | | | | |
|---|---|---|---|---|
| WO | 2007/083316 A2 | 7/2007 | | |
| WO | 2007/111163 A1 | 10/2007 | | |
| WO | 2009/006905 A1 | 1/2009 | | |
| WO | WO 2009 151539 A1 * | 12/2009 | ......... | A61K 31/7088 |
| WO | 2010/049562 A1 | 5/2010 | | |
| WO | 2011/119881 A1 | 9/2011 | | |
| WO | 2011/153348 A2 | 12/2011 | | |

OTHER PUBLICATIONS

Heng, Desmond. et al., "The nano spray dryer B-90," Expert Opin Drug Deliv., 8(7), 965-972, 2011.
Jensen, Ditte Marie Krohn et al., "Spray drying of siRNA-containing PLGA nanoparticles intended for inhalation," Journal of Controlled Release, 142., 138-145, 2010.
Kara, Nour, "The Ligand Nanoparticle Conjugation Approach for Targeted Cancer Therapy," Current Drug Metabolism, 13, -20, 2012.
Kraisit, Pakorn et al., "Nanoparticle formation by using shellac and chitosan for a protein delievey system," Pharmaceutical Development and Technology, 1-8, 2012.
Lee, Sue Huey et al., "Nano spray drying: A novel method for preparing protein nanoparticles for protein therapy," International Journal of Pharmaceutics, 403, 192-200, 2011.
Li, Xiang et al., "Nanoparticles by spray drying using innovative new technology: The Büchi Nano Spray Dryer B-90," Journal of Controlled Release, 147, 304-310, Jul. 24, 2010.
Nassar, Taher et al., "Novel double coated nanocapsules for intestinal delivery and enhanced oral bioavailability of tacrolimus, a P-gp substrate drug," Journal of Controlled Release, 133, 77-84, 2009.
Schmid, Katja et al., "Evaluation of a Vibrating Mesh Spray Dryer for Preparation of Submicron Particles," Respiratory Drug Delivery Europe, 323-326, 2009.
Tahara, Yoshiro et al., "A novel double-coating carrier produced by solid-in-oil and solid-in-water nanodispersion technology for delivery of genes and proteins into cells," Journal of Controlled Release, 161, 713-721, May 9, 2012.
Takashima, Yuuki et al., "Spray-drying preparation of microparticles containing cationic PLGA nanospheres as gene carriers for avoiding aggregation of nanospheres," International Journal of Pharmaceutics. 343., p. 262-269, May 26, 2007.
Wadhwani, P. et al., "Membrane-Active Peptides and the Clustering of Anionic Lipids," Biophysical Journal. 103., p. 265-274, Jul. 2012.
Stevenson, Mark et al.,"Delivery of siRNA mediated by histidine-containing reducible polycations," Journal Controlled Release. 130., p. 46-56, May 24, 2008.
Landen, Charles et al., "Therapeutic EphA2 Gene Targeting In vivo Using Neutral Liposomal Small Interfering RNA Delivery," Cancer Res. 65., p. 6910-6918, Aug. 1, 2005.
Pille, J. et al., "Intravenous Delivery of Anti-RhoA Small Interfering RNA Loaded in Nanoparticles of Chitosan in Mice: Safety and Efficacy in Xenografted Aggressive Breast Cancer," Human Gene Therapy. 17., p. 1019-1026, Oct. 2006.
Zamboni, Williams et al., "Liposomal, Nanoparticle, and Conjugated Formulations of AnticancerAgents," Clin Cancer Res. 11., p. 8230-8234, Dec. 1, 2005.
Sapra Puja et al., "Ligand-Targeted Liposomes for Cancer Treatment," Current Drug Delivery. 2., p. 369-381, 2005.
Wagner Ernst et al., "Targeted nucleic acid delivery into tumors: new avenues for cancer therapy," Biomedicine Pharmacotherapy. 58., p. 152-161, 2004.
Stuart D.D. et al., "A new liposomal formulation for antisense oligodeoxynucleotides with small size, high incorporation efficiency and good stability," Biochimica et Biophysica Acta. 1463., p. 219-229, 2000.
Wheeler, J.J. et al. "Stabilized plasmid-lipid particles: construction and characterization". Gene Therapy. 6., p. 271-281. 1999.
Maurer, Norbert et al. "Spontaneous Entrapment of Polynucleotides upon Electrostatic Interaction with Ethanol-Destabilized Cationic Liposomes". Biophysical. Journal. 80., p. 2310-2326, May 2001.
Anchordoquy, Thomas J. et al. "Maintenance of Transfection Rates and Physical Characterization of Lipid/DNA Complexes after Freeze-Drying and Rehydration". Archives of Biochemistry and Biophysics. 348., p. 199-206, Dec. 1, 1997.
Koster V.S. et al. "Particle size in parenteral fat emulsions, what are the true limitations?". International Journal of Pharmaceutics. 134., p. 235-238, 1996.
Petros Robby et al. "Strategies in the design of nanoparticles for therapeutic applications". Nature Reviews Drug Discovery. 9., p. 615-627, Aug. 2010.
Maeda H. et al. "Tumor vascular permeability and the EPR effect in macromolecular therapeutics: a review". Journal Controlled Release. 65, p. 271-284, 2000.
Veronese Francesco et al. "PEGylation,successful approach to drug delivery". Drug Discovery Today. 10(21)., p. 1451-1458, Nov. 2005.
Wang Jie et al. "Delivery of siRNA Therapeutics: Barriers and Carriers". The AAPS Journal. 12(4), p. 492-503, Dec. 2010.
Kurreck Jens. "Antisense technologies Improvement through novel chemical modifications". Eur. J. Biochem. 270., p. 1628-1644, 2003.
Fessi H. et al. "Nanocapsule formation by interfacial polymer deposition following solvent displacement".International Journal of Pharmaceutics. 55, p. R1-R4, 1989.
Lin W. et al. "Preparation of Sub-100 nm Human Serum Albumin Nanospheres Using a pH-Coacervation Method". Journal of Drug Targeting. 1., p. 237-243, 1993.
Hagigit, Tal et al. "The influence of cationic lipid type on in-vitro release kinetic profiles of antisense oligonucleotide from cationic nanoemulsions". European Journal of Pharmaceutics and Biopharmaceutics. 70, p. 248-259, Mar. 14, 2008.
Wartlick Heidrun et al. "Tumour cell delivery of antisense oligonucleotides by human serum albumin nanoparticles," Journal of Controlled Release. 96., p. 483-495, 2004.
Deluca, Patrick et al. "Parental Drug-Delivery System". Pharmaceutics and Pharmacy Practice. p. 238-250, 1982.
Trissel, Lawrence, "Intravenous Infusion Solutions". ASHP Handbook on Injectable Drugs. 4th ed., p. 622-630, 1986.

* cited by examiner

```
SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Synthetic combined DNA/RNA molecule,
      EGFR-SiRNA S

<400> SEQUENCE: 1
ccauaaaugc uacgaauaut t                                                   21

<210> SEQ ID NO 2
<211> LENGTH: 21
<212> TYPE: DNA
<213> ORGANISM: Artificial Sequence
<220> FEATURE:
<223> OTHER INFORMATION: Synthetic combined DNA/RNA molecule,
      EGFR-SiRNA AS

<400> SEQUENCE: 2
auauucguag cauuuaugga g                                                   21

<210> SEQ ID NO 3
<211> LENGTH: 21
<212> TYPE: DNA
<213> ORGANISM: Artificial Sequence
<220> FEATURE:
<223> OTHER INFORMATION: Synthetic combined DNA/RNA molecule, scrambled
      SiRNA S

<400> SEQUENCE: 3
```

-continued uaacgacgcg acgacguaat t                                    21

<210> SEQ ID NO 4
<211> LENGTH: 21
<212> TYPE: DNA
<213> ORGANISM: Artificial Sequence
<220> FEATURE:
<223> OTHER INFORMATION: Synthetic combined DNA/RNA molecule, scrambled
      SiRNA AS

<400> SEQUENCE: 4
uuacgucguc gcgucguuat t                                    21

<210> SEQ ID NO 5
<211> LENGTH: 21
<212> TYPE: DNA
<213> ORGANISM: Artificial Sequence
<220> FEATURE:
<223> OTHER INFORMATION: Synthetic combined DNA/RNA molecule,
      GFP-SiRNA S

<400> SEQUENCE: 5
auaucauggc cgacaagcat t                                    21

<210> SEQ ID NO 6
<211> LENGTH: 21
<212> TYPE: DNA
<213> ORGANISM: Artificial Sequence
<220> FEATURE:
<223> OTHER INFORMATION: Synthetic combined DNA/RNA molecule,
      GFP-SiRNA AS

<400> SEQUENCE: 6
ugcuugucgg ccaugauaut t                                    21

<210> SEQ ID NO 7
<211> LENGTH: 21
<212> TYPE: DNA
<213> ORGANISM: Artificial Sequence
<220> FEATURE:
<223> OTHER INFORMATION: Synthetic combined DNA/RNA molecule, Chol-GFP
      SiRNA S

<400> SEQUENCE: 7
auaucauggc cgacaagcat t                                    21

<210> SEQ ID NO 8
<211> LENGTH: 21
<212> TYPE: DNA
<213> ORGANISM: Artificial Sequence
<220> FEATURE:
<223> OTHER INFORMATION: Synthetic combined DNA/RNA molecule, Chol-GFP
      SiRNA AS

<400> SEQUENCE: 8
ugcuugucgg ccaugauaut t                                    21

<210> SEQ ID NO 9
<211> LENGTH: 21
<212> TYPE: DNA
<213> ORGANISM: Artificial Sequence
<220> FEATURE:
<223> OTHER INFORMATION: Synthetic combined DNA/RNA molecule,
      Anti-EGFR-SiRNA S

<400> SEQUENCE: 9

```
ccauaaaugc uacgaauaut t                                             21

<210> SEQ ID NO 10
<211> LENGTH: 21
<212> TYPE: DNA
<213> ORGANISM: Artificial Sequence
<220> FEATURE:
<223> OTHER INFORMATION: Synthetic combined DNA/RNA molecule, Anti-EGFR
      SiRNA AS

<400> SEQUENCE: 10
auauucguag cauuuauggt t                                             21

<210> SEQ ID NO 11
<211> LENGTH: 21
<212> TYPE: DNA
<213> ORGANISM: Artificial Sequence
<220> FEATURE:
<223> OTHER INFORMATION: Synthetic combined DNA/RNA molecule,
      Anti-EGFR-SiRNA S

<400> SEQUENCE: 11
ccauaaaugc uacgaauaut t                                             21

<210> SEQ ID NO 12
<211> LENGTH: 21
<212> TYPE: DNA
<213> ORGANISM: Artificial Sequence
<220> FEATURE:
<223> OTHER INFORMATION: Synthetic combined DNA/RNA molecule, Anti-EGFR
      SiRNA AS

<400> SEQUENCE: 12
auauucguag cauuuauggt t                                             21
```

NANO DELIVERY SYSTEMS FOR SIRNA

FIELD OF THE INVENTION

This invention generally relates to nano delivery systems.

BACKGROUND

The discovery of RNA interference (RNAi) has opened up an entirely new field of biology and medicine. The ability of RNAi to specifically silence target genes has yielded not only a new tool for basic research but also raised the concept of developing medicines based on RNAi. RNAi works through the targeting of mRNA via sequence-specific matches and results in degradation of target mRNA or its translational inhibition, leading to the loss of protein expression. This is pharmacologically achieved via the introduction of small 19-21 bp dsRNA molecules called small interfering RNA (siRNA). Since its discovery 10 years ago, siRNA has been widely investigated in vitro for its utility in treating various diseases, such as cancer, neurodegenerative and infectious diseases.

A major barrier to further development of siRNA has been the inability to effectively deliver siRNA in vivo due to the large molecular weight (for example, 13 kDa) and polyanionic nature (e.g. 40 negative phosphate charges). Naked siRNA does not freely cross the cell membrane. Furthermore, unmodified, naked siRNAs are relatively unstable in blood and serum, as they are rapidly degraded by endo- and exonucleases, meaning that they have short half-lives in vivo. Typically, chemical modifications can be introduced into the RNA duplex structure so as to enhance biological stability without adversely affecting gene-silencing activity. Alternatively, they can be formulated with a delivery system that not only enhances cell uptake but also affords biological stability. Several chemical modifications to the backbone, base, or sugar of the RNA have been employed to enhance siRNA stability and activity. However, delivery systems are still required to facilitate siRNA access to its intracellular sites of action.

Indeed, various delivery systems have been developed to enhance the uptake of siRNA into the target tissues after systemic administration. These include the use of polymers [1], lipids [2] or nanoparticles [3,4]. Most of these vectors are cationic to ensure efficient interaction of particles with negatively-charged siRNA nucleotides and to facilitate their cell entry. However, the ability of these cationic particles to deliver siRNA systemically is often poor due to rapid uptake by reticuloendothelial (RES) organs [5], thereby hindering the delivery of these particles to the site of interest. To overcome this problem, polyethylene glycol (PEG) has been used extensively in the formulation as it decreases RES uptake of these particles. This PEGylation also permits the accumulation of the particles in sites where defective vasculature is present, such as tumors, owing to the "Enhanced Permeability and Retention" phenomenon [6].

For lipid-based delivery vectors, various methods for formulating polynucleotide-loaded PEGylated particles have been reported to date, including post-insertion [7], reverse-phase evaporation [8], detergent dialysis [9] and ethanol dialysis [10]. However, most of these methods, though effective, require relatively complicated and lengthy formulation procedures with the resulting particles suspended in an aqueous state. This has led to long-term storage issues including aggregation and/or fusion of the particles, hydrolysis of the lipids, and instability of siRNA nucleotides in an aqueous environment. Moreover, these formulations are also prone to be affected by stresses occurring during transport, such as agitation or temperature fluctuation [11]. These problems, along with the significantly increased effort required for large-scale production of these particles using the existing formulation procedures will limit the widespread adoption of siRNA-containing lipid-based products in the clinics. Clearly, there is a need to develop relatively simple and effective method to formulate siRNA-loaded nanocarriers where the final product is also suitable for long-long term storage.

In the past two decades, several therapeutics based on nanosized particles in the range of 1-1,000 nm have been successfully introduced for the treatment of cancer, pain, and infectious disease. Hydrophilic bio-macromolecules (such as peptides or siRNA), usually exhibiting poor membrane permeability and high sensitivity to environmental conditions (heat, pH, enzymatic degradation) are considered adequate candidates for intracellular delivery by means of nanocarriers. Such nanocarriers can prolong the blood circulation time of these macromolecules which suffer from short physiological half lives, followed by a rapid clearance. However, the number of clinically relevant nanocarriers used for such a purpose is scarce, and major challenges still remain to be solved, especially for their efficient delivery via the parenteral route of administration. siRNAs represent a class of hydrophilic bio-macromolecules where the application of appropriate nanocarriers is most needed to exploit their full therapeutic potential.

REFERENCES

[1] Stevenson M. et al., *J Control Release* 2008, 130, p. 46-56
[2] Landen C. N. et al., *Cancer Res.* 2005, 65, p. 6910-9918
[3] Pille J. et al., *Hum. Gene. Ther.* 2006, 17, p. 1019-1026
[4] WO 2007/083316
[5] Zamboni W. et al., *Clin. Cancer Res.* 2005, 11, p. 8230-8234
[6] Sapra P. et al., *Curr. Drug Deliv.* 2005, 2, p. 369-381
[7] Wagner E. et al., *Biomed. Pharmacother.* 2004, 58, p. 152-161
[8] Stuart D. et al., *Biochimica et Biophysica Acta* 2000, 1463, p. 219-229
[9] Wheeler J. J. et al., *Gene Ther.* 1999, 6, p. 271-281
[10] Maurer N. et al., *Biophys. J.* 2001, 80, p. 2310-2326
[11] Anchordoquy T. J. et al., *Arch. Biochem. Biophys.* 1997, 348, p. 199-206
[12] Koster V. S., et al., *Intl. J. Pharmaceu.* 1996, 134(1-2), p. 235-238
[13] Petros R. A. and DeSimone J. M., *Nature Rev. Drug Discovery* 2010, 9(8), p. 615-627
[14] Maeda H. et al., *J. Control. Release* 2000, 65(1-2), p. 271-284
[15] Veronese F. M. and Pasut G., *Drug Discovery Today* 2005, 10(21), p. 1451-1458
[16] Heng, D. et al., *Expert Opin. Drug Deliv.* 2011, 8(7), p. 965-972
[17] Wang J. et al., *AAPS Journal* 2010, 12(4), p. 492-503
[18] Kurreck J., *Eur. J. Biochem.* 2003, 270(8), p. 1628-1644
[19] Fessi H. et al., *Intl. J. Pharmaceu.* 1989, 55(1), p. R1-R4
[20] Lin W. et al., *J. Drug Targ.* 1993, 1, p. 237-243
[21] Hagigit T. et al. *Eur. J. Pharmaceu. Biopharmaceu.* 2008, 70(1), p. 248-259
[22] Wartlick H. et al., *J. Control. Release* 2004, 96(3), p. 483-495

[23] Lee S. H. et al., *Intl. J. Pharmaceu.* 2011, 403, p. 192-200

[24] Schmid K. et al., *Respir. Drug Deliv. Europe* 2009, p. 323-326

SUMMARY OF THE INVENTION

The present invention makes use of a unique methodology of double nano-encapsulation for protecting and controlling the release of active agents, either hydrophobic or hydrophilic agents, such as siRNA (or its different chemical derivatives such as cholesterol labeled siRNA), from stable nanoparticles of opposite characteristics (hydrophobic or hydrophilic). The protection of the active agent was achieved by loading the agent to be protected, into nanocarriers, which were subsequently encapsulated into sub-micron nanoparticles. The sub-micron nanoparticles (nanocapsules or nanospheres) formation has been successfully achieved by the use of novel nanospray techniques.

The delivery systems of the invention provide a platform for systemic delivery of hydrophilic bio-macromolecules (such as siRNA) or hydrophobic bio-macromolecules improving the drug's half-life, biodistribution and pharmacokinetics.

Thus, the present invention also relates to a drug delivery system comprising double-encapsulated active agents, enabling stabilization of either hydrophilic or hydrophobic active agents, and permitting their targeted delivery into cells.

In one of its aspects, the invention provides a nanoparticle encapsulating a plurality of nanocarriers (one or more), at least one of said plurality of nanocarriers containing at least one active agent, said nanoparticle having an averaged diameter of between 400 and 950 nm.

In some embodiments, the double-encapsulation of the active agent to form nanoparticles according to the invention is obtainable by nanospraying, as detailed herein. The process of nanospraying may further comprise drying the nanoparticles obtained by the nanospraying method. The drying may be achieved by evaporation of the media solvents by using, for example, lyophillization, thermal drying, reduced pressure, solvent extraction and other techniques.

In additional embodiments, the nanoparticles are selected from:

i. where the active agent is hydrophobic, the nanocarrier material is hydrophobic and the nanoparticle material is hydrophilic;
ii. where the active agent is hydrophilic, the nanocarrier material is hydrophilic and the nanoparticle material is hydrophobic;
iii. where the active agent is hydrophobic, the nanocarrier material is hydrophobic and the nanoparticle material is hydrophobic; and
iv. where the active agent is hydrophilic, the nanocarrier material is hydrophilic, and the nanoparticle material is hydrophilic.

In other embodiments, the active agent is siRNA. In some embodiments, where the active agent is siRNA, the nanocarrier further comprises a polycationic lipid. In some embodiments, the polycationic lipid is 1,2-dioleoyl-3-trimethylammonium-propane (DOTAP).

As may be understood by a person versed in the art, the term "material" refers to the material(s) from which the nanoparticle or nanocarrier is made of. Thus, the term "nanocarrier material" refers to material(s) from which the nanocarrier is made of. Similarly, the "nanoparticle material" is the material(s) from which the nanoparticle is made of. The plurality of nanocarriers may be made of different materials. The nanocarrier material(s) is, in some embodiments, different from the nanoparticle material.

In some embodiments, the nanocarrier may be composed of a metallic material, or may contain a metallic material in combination with a non-metallic material. In some embodiments, the nanocarriers are gold nanospheres.

The material hydrophobicity or hydrophilicity may be due to the material intrinsic behaviors towards water, as further discussed below, or may be achieved (or tuned) by modifying the material by one or more of cross-linking said material, derivatization of the material, charge induction to said material (rendering it positively or negatively charged), complexing or conjugating said material to another material and by any other means known in the art.

Thus, in accordance with the present invention, the selection of a material may be based on the material intrinsic properties or based on the material's ability to undergo such aforementioned modification to render it more or less hydrophobic or hydrophilic.

In some embodiments, the nanoparticle material and/or the nanocarrier material may be cross-linked in order to reduce material hydrophilicity (decrease solubility in aqueous media).

In another aspect of the present invention, there is provided a nanoparticle encapsulating a plurality of nanocarriers, at least one of said plurality of nanocarriers (one or more) containing at least one active agent, said nanoparticle being prepared by nano spraying, as defined herein.

In some embodiments, the nanoparticles have an averaged diameter of less than 4 micron. In other embodiments, the nanoparticles have an averaged diameter of less than 2 micron. In other embodiments, the nanoparticles have an averaged diameter of less than 1 micron. In further embodiments, said nanoparticles having averaged diameter of less than 950 nm. In some embodiments, the formed nanoparticles have averaged diameter of between 400 and 950 nm.

In some embodiments, the nanoparticles are selected from:

i. where the active agent is hydrophobic, the nanocarrier material is hydrophobic and the nanoparticle material is hydrophilic;
ii. where the active agent is hydrophilic, the nanocarrier material is hydrophilic and the nanoparticle material is hydrophobic;
iii. where the active agent is hydrophobic, the nanocarrier material is hydrophobic and the nanoparticle material is hydrophobic; and
iv. where the active agent is hydrophilic, the nanocarrier material is hydrophilic, and the nanoparticle material is hydrophilic.

In further embodiments, the nanoparticle material and/or the nanocarrier material may be cross-linked in order to reduce material hydrophilicity (decrease solubility in aqueous media).

In other embodiments, the active agent is siRNA. In some embodiments, where the active agent is siRNA, the nanocarrier further comprises a polycationic lipid. In some embodiments, the polycationic lipid is 1,2-dioleoyl-3-trimethylammonium-propane (DOTAP).

In another aspect of the invention, there is provided a nanoparticle encapsulating a plurality of nanocarriers (one or more), at least one of said plurality of nanocarriers containing at least one active agent, such that:

where the active agent is hydrophobic, the nanocarrier material is hydrophobic and the nanoparticle material is hydrophilic; the nanoparticle material being optionally further cross-linked to reduce their solubility in aqueous media; or where the active agent is hydrophilic, the nanocarrier material is hydrophilic, optionally cross-linked, and the nanoparticle material is hydrophobic.

In some embodiments, the nanoparticles have an averaged diameter of less than 4 micron. In other embodiments, the nanoparticles have an averaged diameter of less than 2 micron. In other embodiments, the nanoparticles have an averaged diameter of less than 1 micron. In further embodiments, said nanoparticles having averaged diameter of less than 950 nm. In still additional embodiments, the nanoparticles have averaged diameter of between 400 and 950 nm.

In some embodiments, said nanoparticles are formed by nanospraying-drying.

In other embodiments, the active agent is hydrophilic. In some embodiments, where the active agent is siRNA, the hydrophilic active agent is siRNA. In such embodiments, the nanocarrier further comprises a polycationic lipid. In some embodiments, the polycationic lipid is 1,2-dioleoyl-3-trimethylammonium-propane (DOTAP).

In another aspect of the invention, there is provided a nanoparticle encapsulating a plurality of nanocarriers, at least one of said plurality of nanocarriers (one or more) containing at least one active agent, wherein said nanoparticle having averaged diameter of between 400 and 950 nm, wherein:

where the active agent is hydrophobic, the nanocarrier material is hydrophobic and the nanoparticle material is hydrophilic; the nanoparticle material being optionally further cross-linked to reduce their solubility in aqueous media; or where the active agent is hydrophilic, the nanocarrier material is hydrophilic, optionally cross-linked, and the nanoparticle material is hydrophobic.

In some embodiments, said nanoparticles are formed by nanospraying.

In other embodiments, the active agent is hydrophilic. In some embodiments, where the active agent is siRNA, the hydrophilic active agent is siRNA. In such embodiments, the nanocarrier further comprises a polycationic lipid. In some embodiments, the polycationic lipid is 1,2-dioleoyl-3-trimethylammonium-propane (DOTAP).

In another aspect of the invention, there is provided a nanoparticle encapsulating a plurality of nanocarriers (one or more), at least one of said plurality of nanocarriers containing at least one active agent, wherein said nanoparticle having averaged diameter of between 400 and 950 nm, wherein:

where the active agent is hydrophobic, the nanocarrier material is hydrophobic and the nanoparticle material is hydrophilic; the nanoparticle material being optionally further cross-linked to reduce their solubility in aqueous media; or where the active agent is hydrophilic, the nanocarrier material is hydrophilic, optionally cross-linked, and the nanoparticle material is hydrophobic;

wherein said nanoparticles are formed by nanospraying.

In yet another aspect, the invention provides a nanoparticle encapsulating a plurality of nanocarriers (one or more), at least one of said plurality of nanocarriers containing at least one active agent, wherein said nanoparticle having averaged diameter of between 400 and 950 nm, said nanoparticle being prepared by nanospraying, as defined herein.

In some embodiments, the nanoparticles are selected from:

i. where the active agent is hydrophobic, the nanocarrier material is hydrophobic and the nanoparticle material is hydrophilic;

ii. where the active agent is hydrophilic, the nanocarrier material is hydrophilic and the nanoparticle material is hydrophobic;

iii. where the active agent is hydrophobic, the nanocarrier material is hydrophobic and the nanoparticle material is hydrophobic; and iv. where the active agent is hydrophilic, the nanocarrier material is hydrophilic, and the nanoparticle material is hydrophilic.

In further embodiments, the nanoparticle material and/or the nanocarrier material may be cross-linked in order to reduce material hydrophilicity (decrease solubility in aqueous media).

In other embodiments, the active agent is siRNA. In some embodiments, where the active agent is siRNA, the nanocarrier further comprises a polycationic lipid. In some embodiments, the polycationic lipid is 1,2-dioleoyl-3-trimethylammonium-propane (DOTAP).

The "nanoparticle" of the invention is a particulate carrier, a nanocapsule (NC) or a nanosphere (NS), which is biocompatible and sufficiently resistant to chemical and/or physical destruction, such that a sufficient amount of the nanoparticles remains substantially intact after administration into the human or animal body and for a sufficient period of time to reach the desired target organ (tissue). Generally, the nanoparticles are spherical in shape, having an average diameter of up 2 μm (micron) with the majority of the nanoparticles having averaged diameter of less than 1 μm (micron).

As indicated hereinabove, in some aspects and embodiments of the invention, the nanoparticles have averaged diameter of less than 1 micron. In some aspects and embodiments, the nanoparticles have averaged diameter of between about 400 and 950 nm. In other embodiments, the averaged diameter of said nanoparticle is between about 400 and 900 nm. In some other embodiments, the averaged diameter is between about 400 and 800 nm. In further embodiments, the averaged diameter is between about 400 and 700 nm. In additional aspects and embodiments, the nanoparticles have averaged diameter of between 400 and 600 nm.

It should be noted that the averaged diameter of nanoparticles may be measured by any method known to a person skilled in the art. The term "averaged diameter" refers to the arithmetic mean of measured diameters, wherein the diameters range ±25%, ±15%, ±10%, or ±5% of the mean. Where the nanoparticles are not spherical, the term refers to the effective average diameter being the largest dimension of the particle.

The nanoparticle of the invention should be large enough to be able to hold a plurality of nanocarriers, yet at the same time be of a smaller enough size to be able to undergo internalization.

The plurality (one or more) of "nanocarriers" which are contained within the nanoparticles of the invention, are themselves particulate carriers, each having an average diameter of less than 300, less than 250, or less than 200 nm. The nanocarriers may be in the form of nanocapsules (NC) or nanospheres (NS). Generally, the nanocarriers are spherical in shape. Where the shape of the nanocarriers is not spherical, the diameter refers to the longest dimension of the particle.

The number of nanocarriers which are encapsulated within a single nanoparticle according to the invention may vary depending on, e.g., the size of the nanocarrier or the relative sizes of the nanocarrier and the nanoparticle. Typically, each nanoparticle may contain between 1 and a few (6-7) dozens of nanocarriers (being said plurality of nanocarriers). In some embodiments, each nanoparticle comprises between 2 and 50 nanocarriers. In some embodiments, each nanoparticle comprises between 2 and 40 nanocarriers. In some embodiments, each nanoparticle comprises between 2 and 30 nanocarriers. In some embodiments, each nanoparticle comprises between 2 and 20 nanocarriers. In some embodiments, each nanoparticle comprises between 2 and 10 nanocarriers.

In some embodiments, each nanoparticle comprises more than 2 nanocarriers.

The nanocarriers are said to "contain" said at least one active agent. As exemplified hereinbelow, the at least one active agent may be contained in a core of said nanocarrier, and/or may be contained in the material matrix making up the nanocarrier, and/or may be associated with a surface region (one or more, or whole surface) of said nanocarriers.

In some embodiments, where the nanocarriers are metallic particles, e.g., gold nanospheres, the at least one active agent is associated with a surface region (one or more, or whole surface) of said metallic particles.

In some embodiments, the nanocarriers themselves are prepared by nano spraying, as detailed herein.

In some embodiments, the averaged diameter of a nanocarrier is at least about 50 nm.

In some embodiments, the averaged diameter of a nanocarrier is between about 100 and 300 nm. In other embodiments, the averaged diameter is between about 200 and 300 nm. In other embodiments, the averaged diameter is between about 50 and 300 nm. In other embodiments, the averaged diameter is between about 50 and 250 nm. In further embodiments, the averaged diameter is between about 50 and 200 nm. In further embodiments, the averaged diameter is between about 50 and 150 nm. In further embodiments, the averaged diameter is between about 50 and 100 nm.

As a person versed in the art would understand, the "hydrophilicity" of the materials is a characteristic of materials exhibiting affinity for water, while the "hydrophobic" materials possess the opposite response to water.

The solubility or insolubility of the nanoparticles in aqueous media may be altered by cross-linking the nanocarrier or final nanoparticle material to increase or decrease the final nanoparticle solubility in such media.

For the chosen application, the nanoparticle and/or the nanocarrier may be in the form of a "nanocapsules", namely having a core/shell structure, with a polymeric shell and a core which may be empty or which may contain at least one oily or aqueous phase. Alternatively the nanoparticles and/or nanocarriers may be of a substantially uniform composition, namely as "nanospheres" (NSs) of a continuous material, not featuring a distinct core/shell structure.

In some embodiments, the nanoparticles of the invention and the plurality of nanocarriers contained therein are in the form of nanocapsules. In other embodiments, the nanoparticles and the nanocarriers are both nanospheres. In some other embodiments, the nanoparticles may be in the form of nanocapsules and the nanocarriers may in the form of nanospheres. In further embodiments, the nanoparticles may be in the form of nanospheres and the nanocarriers may in the form of nanocapsules.

The term "encapsulation" (or any lingual variation thereof) refers to, e.g., the containment of at least one nanocarrier within a nanoparticle, or to the containment of an active material in a nanocarrier (as defined hereinabove). Therefore, according to some embodiments, the nanoparticles are said to encapsulate one or more nanocarriers.

In some other embodiments, the nanoparticles encapsulate a plurality of nanocarriers being selected from nanocapsules, nanospheres and mixtures thereof. Notwithstanding the form of the polarity of nanocarriers (NS and/or NC), the nanoparticles of the invention may encapsulate a plurality of nanocarriers of different materials and/or different active agents. The nanoparticles of the invention, for example, may contain a plurality of nanocarriers of the same polymeric material (thus having the same hydrophilic/hydrophobic properties), with one or more different active agents. Similarly, the nanoparticles of the invention may contain a plurality of nanocarriers of different polymeric materials, however containing each the same active agent.

In some aspects of the invention, there are provided mixtures of nanoparticles of the invention, said mixtures comprising one or more types of nanoparticles, said one or more nanoparticles types differing from each other by at least any one of:
1. nanocarrier material,
2. nanoparticle material,
3. active agent,
4. nanoparticle/nanocarrier form (NS or NC),
5. nanoparticle/nanocarrier size.

As stated above, in some aspects and embodiments of the invention, the nanoparticles are obtainable by nanospraying. This process comprises transporting (e.g., delivering, spraying) through a screen (e.g., mesh) having one or more orifices (holes, openings, punctures, pinholes) of a predetermined size (diameter), a colloidal composition comprising a plurality of nanocarriers and a nanoparticle material e.g., a polymeric material, in a liquid medium, said plurality of nanocarriers comprising at least one active agent and said nanoparticle material is at least partially soluble in said liquid medium, the size of said orifices determining the (maximal) size (diameter) of the nanoparticles.

In some embodiments, the orifices allow production of nanoparticles having averaged diameter of less than 4 micron, or less than 2 micron, or less than 1 micron, or less than 950 nm, or between 400 and 950 nm, or between about 400 and 900 nm, or between about 400 and 800 nm, or between about 400 and 700 nm, or between 400 and 600 nm.

To permit such nanoparticle sizes, the orifices size (hole diameter) is selected to range from 7 micron to 1 micron. In some embodiments, the screen is between 4 and 6 micron mesh size. In some embodiments, the screen is 4 micron mesh size.

In some embodiments, the colloidal composition is prepared by mixing a plurality of nanocarriers with a nanoparticle material e.g., a polymeric material, in a liquid medium.

In some embodiments, the nanospraying method further comprises the step of drying the nanoparticles.

In some embodiments, the nanocarriers are obtained by nanospraying.

The nanoparticles of the invention are mainly comprised of polymers. The term "polymer" includes homopolymers, copolymers, such as for example, block, graft, random and alternating copolymers as well as terpolymers, further including their derivatives, combinations and blends thereof. In addition to the above, the term includes all geometrical configurations of such structures including linear, block, graft, random, alternating, branched structures, and combination thereof.

The polymers utilized in the construction of the nanoparticles are biodegradable, namely, they degrade during in vivo use. In general, degradation attributable to biodegradability involves the degradation of a biodegradable polymer into its component subunits, or digestion, e.g., by a biochemical process carried out for example by enzymes, of the polymer into smaller, non-polymeric subunits. The degradation may proceed in one or both of the following: biodegradation involving cleavage of bonds in the polymer matrix, in which case, monomers and oligomers typically result, or the biodegradation involving cleavage of a bond internal to side chain or that connects a side chain to the polymer backbone. In some embodiments, biodegradation encompasses both general types of biodegradation. The polymers are additionally biocompatible, namely, they are substantially non-toxic or lacking injurious impact on the living tissues or living systems to which they come in contact with.

The nanoparticles of the invention may be used as a drug delivery platform, enabling penetration and release of active agents into targeted cells or organelles within the cell. To facilitate cell membrane penetration, the nanoparticles of the invention may be associated with different targeting agents.

In some embodiments, the outer surfaces of the nanoparticles are associated with at least one targeting agent. In such embodiments, the at least one targeting agent is selected from monoclonal antibodies, such as trastuzumab (Herceptin®) recognizing HER-2 receptor overexpressed in solid tumors; AMBLK8 recognizing H ferritin, cetuximab (Erbitux®) recognizing EGFR receptors; Rituximab (MabThera®) recognizing CD20; bevacizumab (Avastin®) inhibiting the function of a natural protein called "vascular endothelial growth factor" (VEGF) that stimulates new blood vessel formation; ranibizumab (Lucentis®), providing stronger binding to VEGF-A; small molecules such as folic acid or folate; hyaluronic acid or hyaluronan; tumor penetrating peptides, typically about 6-15 kDa; epidermal growth factor (EGF); transferrin; ferritin; Arginine-Glycine-Aspartic acid (RGD) peptide; epithelial cell adhesion molecule (EpCAM); intercellular adhesion molecule 1 (ICAM-1); carcinoembrionic antigen (CEA); vasoactive intestinal peptide; CA 15-3 antigen; MUC1 protein; CD20; CD33; integrins; lymphatic targeting moieties (such as LyP-1); aptamers, such as PSMA aptamer or VEGF aptamer; oligosaccharides and others.

In some embodiments, the targeting agent is bevacizumab (Avastin®) or Ranibizumab (Lucentis®).

As used herein, the term "association" or any lingual variation thereof refers to the chemical or physical interaction which holds two entities together (e.g., the nanoparticle and the targeting agent, the nanocarrier surface with a linker moiety or with an active agent, or any interaction referred to as such). The interaction may be any type of chemical or physical bonding interaction known to a person skilled in the art. Non-limiting examples of such interactions (associations) include ionic bonding, covalent bonding, coordination bonding, complexation, hydrogen bonding, van der Waals bonding, hydrophobicity-hydrophilicity interactions, etc. In some embodiments, the association is via covalent bonding. In other embodiments, the association is via coordinative bonding. It should be understood to a person skilled in the art that in some cases the associative interactions between two atoms or two chemical entities may involve more than one type of chemical and/or physical interactions.

Once inside a living cell in vivo or in vitro, the active agent has to be delivered to the proper organelle, or alternatively escape compartmentalization into cell organelles, such as endosomes and lysosomes, and be intracellularly bioavailable. Therefore, in some embodiments, said at least one nanocarrier has a cationic lipid (such as DOTAP) or cell penetrating peptides which contain various amino acids, such as arginine or lysine residues, conferring positive charges to the peptide. These peptides can penetrate the cell and release the cargo of the nanocarrier in the cytoplasm. Such peptides may be selected from HIV-TAT, penetratin, Gramicidin S, MSI-103, MSI-103-Arg, PGLa, PGLa-Arg, Magainin 2, Magainin-2-Arg, KIGAKI, BP100, MAP, MAP-Arg, SAP, PEP-1, transportan, FP23 and others.

In some embodiments, the cationic lipid is DOTAP.

As noted above, the nanoparticles may comprise at least one nanocarrier, the nanocarrier being a nanosphere comprising a hydrophilic matrix (material), wherein the at least one active agent is hydrophilic and distributed within the hydrophilic matrix.

In some embodiments, the nanosphere hydrophilic material is selected from dextran, hylauronate, human serum albumin (HSA) being normal or cross-linked, bovine serum albumin (BSA) being normal or cross-linked, chitosan, shellac, collagen, gelatin, gum arabic, polyvinyl alcohol, cyclodextrin, each being alone or in combination with one or more of the aforementioned. In other embodiments, the hydrophilic material is human serum albumin (HSA), bovine serum albumin (BSA) or hyaluronic acid.

In some embodiments, the hydrophilic material is human serum albumin (HSA) having an average molecular weight of about 66,500 Da, or hyaluronic acid having an average molecular weight ranging in size from 20,000 up to 1,000,000 Da.

According to such embodiments, the hydrophilic active agent may be selected from therapeutic peptides or proteins, such as exenatide, insulin, growth hormone, triptorelin acetate, buserelin, nafarelin, and others; DNA, RNA, siRNA, tRNA or derivatives or fragments thereof.

In some embodiments, the hydrophilic agent is siRNA.

In other embodiments, the siRNA has the nucleotide sequence of SEQ ID NOS: 1, 2, 3, 4, 5, 6, 7, 8, 9, 10, 11, or 12.

In some embodiments, the hydrophilic material is cross-linked to lower the nanocarrier's solubility in aqueous media.

In some embodiments, where the nanocarrier is hydrophilic in nature, the nanoparticle may be in the form of a nanocapsule which comprises a hydrophobic shell (i.e. a hydrophobic nanoparticle encapsulating the hydrophilic nanocarriers). This arrangement enables the encapsulation and stabilization of hydrophilic agents, normally problematic to stabilize and deliver.

In such embodiments, the hydrophobic shell is of a polymer selected from lactic acid, poly(D,L-lactic-co-glycolic acid) (PLGA), poly(D,L-lactic acid) (PLA), poly(ε-caprolactone), poly(2-dimethylamino-ethylmethacrylate) homopolymer, poly(2-dimethylamino-ethylmethacrylate)-b-poly(ethyleneglycol)-α-methoxy-ω-metacrylate copolymers, polycyanoacrylates, polyanhydride polymers and combinations thereof.

In some embodiments, the hydrophobic shell is a PEGylated derivative of a polymer selected from lactic acid,poly(D,L-lactic-co-glycolic acid) (PLGA), poly(D,L-lactic acid) (PLA), poly(ε-caprolactone), poly(2-dimethylamino-ethylmethacrylate) homopolymer, poly(2-dimethylamino-ethylmethacrylate)-b-poly(ethyleneglycol)-α-methoxy-ω-metacrylate copolymers, polycyanoacrylates, polyanhydride polymers and combinations thereof.

In other embodiments, the hydrophobic shell is selected from lactic acid, poly(D,L-lactic-co-glycolic acid) (PLGA) and combinations thereof, including PEGylated derivatives thereof (alone or in combination). In such embodiments, the PLGA has a molecular weight of between about 4,000 and 100,000 Da.

In order to decrease cell membrane deterrence, the hydrophobic shell may have an outer surface associated with at least one polyethylene glycol (PEG) moiety.

In other embodiments of the invention, the nanoparticles may comprise at least one nanocarrier, the nanocarrier being a nanosphere comprising a hydrophobic polymer matrix; the at least one active agent contained within said nanosphere is also hydrophobic.

In such embodiments, the hydrophobic polymer matrix may be selected from lactic acid, poly(D,L-lactic-co-glycolic acid) (PLGA), poly(D,L-lactic acid) (PLA), poly(ϵ-caprolactone), poly(2-dimethylamino-ethylmethacrylate) homopolymer, poly(2-dimethylamino-ethylmethacrylate)-b-poly(ethyleneglycol)-α-methoxy-ω-methacrylate copolymers, polycyanoacrylates and combinations thereof and their PEGylated derivatives.

In other embodiments, the hydrophobic polymer matrix is selected from lactic acid, poly(D,L-lactic-co-glycolic acid) (PLGA) and combinations thereof, including mixtures with PEGylated derivatives thereof.

In some other embodiments, said PLGA has a molecular weight of between about 4,000 and 100,000 Da.

In further embodiments, the hydrophobic active agent is selected from an analgesic or anti-inflammatory agent (such as aloxiprin, auranofin, azapropazone, benorylate, diflunisal, etodolac, fenbufen, fenoprofen calcim, flubiprofen, ibuprofen, indomethacin, ketoprofen, meclofenamic acid, mefenamic acid, nabumetone, naproxen, oxyphenbutazone, phenylbutazone, piroxican, or sulindac); an enthelmintic agent (such as albendazole, bephenium hydroxynaphthoate, cambensazole, dichlorophen, ivermectin, mebendazole, oxamniquine, oxefendazole, oxantel embonate, praziquantel, pyrantel embonate, or thiabendazole); an anti-arrhythmic agent (such as amiodarone, disopyramide, flecainide acetate, or quinidine sulphate); an anti-bacterial agent (such as benethamine penicillin, cinoxacin, ciprofloxacin, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphacetamide, sulphamerazine, sulphadiazine, sulphafurazole, sulphamethoxazole, sulphapyridine, tetracycline, or trimethoprim); an anti-coagulant (such as dicoumarol, dipyridamole, nicoumalone or phenindione); an anti-depressant (such as amoxapine, meprotiline, mianserin, nortriptyline, trazodone, or tirimipramine maleate); an antidiabetic (such as acetothexamide, chlorpropamide, glibenclamide, gliclazide, glipizide, tolazamide, or tolbutramide); an anti-epileptic (such as beclamide, carbamazepine, clonazepine, ethotoin, methoin, methsuximide, methylphenobarbitone, oxcarb azepine, paramethadione, phenacemide, phenobarbitone, phenyloin, phensuximide, primidone, sulthiame, or valproic acid); an anti-fungal agent (such as amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine, terconazole, tioconazole or undecenoic acid); an anti-gout agent (such as allopurinol, probenecid or sulphin-pyrazone); an anti-hypertensive agent (such as amlodipine, benidipine, darodipine, dilitazem, diazoxide, felodipine, guanabenz acetate, isradipine, minoxidil, nicardipine, nifedipine, nimodipine, phenoxybenzamine, prazosin, reseprine or terazosin); an anti-malarial agent (such as amodiaquine, chloroquine, chlorproguanil, halofantrine, mefloquine, proganil, pyrimethamine, or quinine sulphate); an anti-migraine agent (such as dihydroergotamine mesylate, ergotamine tartarate, methysergide maleate, pizotifen maleate or sumatriptan succinate); an anti-muscarinic agent (such as atropine, benzhexol, biperiden, ethopropazine, hyoscyamine, mepenzolate bromide, oxyphencylcimine, or tropicamide); an anti-neuroplastic agent or immunosuppressant (such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine, tamoxifen citrate, testolactone, tacrolimus, or sirolimus); an anti-protazoal agent (such as benznidazole, clioquinol, decoquinate, diiodohydroxyquinoline, diloxanide furoate, dinitolmide, furzolidone, metronidazole, nimorazole, nitrofurazone, ornidazole, or tinidazole); an anti-thyroid agent (such as carbimazole or propylthiouracil); an alixiolytic, sedative, hypnotic or neuroleptic agent (such as alparzolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, dozapine, diazepam, droperidol, ethinamate, flunanisone, flunitrazepam, fluopromazine, flupenthixol decanoate, fluphenazine decanoate, flurazepam, baloperidol, lorazepam, lormetazepam, medazepam, meprobamate, methaqualone, midazolam, nitrazepam, oxazepam, pentobarbitone, perphenazine primozide, prochlorperazine, sulpiride, temazepam, thioridazine, triazolam, or zopiclone); a beta-blocker (such as acebutolol, alprenolol, atenolol, labetalol, metoprolol, nadolol, oxprenolol, pindolol, or propranolol); a cardiac inotropic agent (such as amrinone, digitoxin, digoxin, enoximone, lanatoside C, or medigoxin); a corticosteroid (such as beclomethasone, betamethasone, budesonide, cortisone acetate, desoxymethasone, dexamethasone, fludrocortisones acetate, flunisolide, flucortolone, fluticasone propionate, hydrocortisone, methylprednisolone, prednisolone, prednisone, or triamcinolone); a diuretic agent (such as acetazolamide, amiloride, bendofluazide, bumetanide, chlorothiazide, chlorthalidone, ethacrynic acid, frusemide, metolazone, spironolactone, or triamterene); an anti-Parkinsonian agent (such as bromocriptine mesylate, or lysuride maleate); a gastro-intestinal agent (such as bisacodyl, cimetidine, cisapride, diphenoxylate, domperidone, famotidine, loperamide, mesalazine, nizatidine, omeprazole, ondansetron, ranitidine, or sulphasalazine); an histamine H1-receptor antagonist (such as acrivastine, astemizole, cinnarizine, cyclizine, cyproheptadine, dimenhydrinate, flunarizine, loratadine, meclozine, oxatomide or terfenadine); a lipid regulating agent (such as bezafibrate, clofibrate, fenofibrate, gemfibrozil, or probucol); a nitrate or anti-anginal agent (such as amyl nitrate, glyceryl trinitrate, isosorbide dinitrate, isosorbide mononitrate, or pentaerythritol tetranitrate); a nutritional agent (such as betacarotene, vitamin A, vitamin B2, vitamin D, vitamin E or vitamin K); an HIV protease inhibitor (such as nelfinavir); an opioid analgesic (such as codeine, dextropropyoxyphene, diamorphine, dihydrocodeine, meptazinol, methadone, morphine, nalbuphine, or pentazocine); a sex hormone (such as clomiphene citrate, danazol, ethinyl estradiol, medroxyprogesterone acetate, mestranol, methyltestosterone, morethisterone, norgestrel, estradiol, conjugated oestrogens, progesterone, stanozolol, stibestrol, testosterone, or tibolone); or a stimulant agent (such as amephetamine, dexamphetamine, dexfenfluramine, fenfluramine or mazindol).

In some embodiments where the nanocarrier is of a hydrophobic nature, the nanoparticle may be a nanocapsule comprising a hydrophilic shell. In such embodiments, the hydrophilic shell may be selected from dextran, hylauronate, human serum albumin (HSA), bovine serum albumin (BSA), chitosan, shellac, collagen, gelatin, gum arabic, polyvinyl alcohol, cyclodextrin, alone or in combination. If needed, each of said polymers may be cross-linked.

According to some embodiments, the hydrophilic material is human serum albumin (HSA), bovine serum albumin (BSA) or hyaluronic acid.

According to other embodiments, the hydrophilic matrix is human serum albumin (HSA) having an average molecular weight of about 66,500 Da.

The drug delivery systems of the invention may be tailored and modified based on the active agent (material) to be carried therein. The nanoparticles carrying a plurality of nanocarriers may be used to carry and deliver one or more active materials. For example, a hydrophobic active material may be encapsulated in a hydrophobic nanocarrier (nanosphere or nanocapsule) and a further active material which is hydrophilic in nature may be entrapped within the hydrophilic material matrix of the nanoparticle material. Similarly, hydrophilic nanocarriers may encapsulate more than one hydrophilic active materials and the hydrophobic nanoparticle material may hold one or more hydrophobic active materials.

Depending on the final application and/or the nature of the delivery system, whether the active agent is hydrophobic or hydrophilic, it can be associated to the primary nanocarrier (being hydrophobic or hydrophilic), via chemical bonds (as defined hereinabove, e.g., polar, ionic, van der Waals, etc) and for polyanionic macromolecules, via the addition of a 'helper lipid' (such as DOTAP). This chemical association of the active agent to the nanocarriers or nanoparticles prevents leaking of the active agent and the efficacy of encapsulation process is maintained or secured (this approach may be useful depending on the final application and/or particular delivery system).

The "active agent" to be encapsulated within the plurality of nanocarriers or in the polymeric matrix of the nanocarriers and/or nanoparticles may be selected amongst vitamins, proteins, anti-oxidants, nucleic acids, short or long oligonucleotides (in different conformations), siRNA and its chemical derivatives, peptides, polypeptides, lipids, carbohydrates, hormones, antibodies, monoclonal antibodies, vaccines and other prophylactic agents, drugs, diagnostic agents, contrasting agents, nutraceutical agents, small molecules (of a molecular weight of less than about 1,000 Da or less than about 500 Da), electrolytes, immunological agents and any combination of any of the aforementioned.

In some additional embodiments, particular agents to be encapsulated in systems according to the invention include exenatide, insulin and others.

In other embodiments, the active agent is siRNA.

In further embodiments, the siRNA to be encapsulated is selected from siRNA having any one of the nucleotide sequences of SEQ ID NOS: 1 through 12.

In order to modify the hydrophibicity/hydrophilicity of a certain active material, the material may be appended with a negative or positive charge or with a lipophilic (hydrophobic) moiety.

In some embodiments, said active agent is negatively charged and the nanocarrier is also negatively charged. In such embodiments, the cationic lipid is selected from 1,2-dioleoyl-3-trimethylammonium-propane (DOTAP), stearylamine, and oleylamine.

According to some embodiments, the cationic lipid is DOTAP.

In some embodiments, where the active agent is associated with at least a region of the nanocarrier surface, the association (as generally defined above) may be directly to chemical groups present on the surface of the nanocarrier particle, or may be via one or more linking groups which chemically or physically associate the surface region with the active material. The linking group may be a single atom or a group of atoms and may be selected in a non-limiting fashion from thiols, hydroxides, amines, alkyl groups, phosphates, carboxylates, PEGs, and other known in the art.

The invention provides a nanoparticle encapsulating a plurality of nanocarriers (one or more), at least one of said plurality of nanocarriers containing at least one active agent, the active agene being siRNA.

In some embodiments, the nanocarrier further comprises a polycationic lipid, the polycationic lipid being 1,2-dioleoyl-3-trimethylammonium-propane (DOTAP).

In other embodiments, said nanoparticle has an averaged diameter of between 400 and 950 nm.

In some other embodiments, the nanoparticle material is hydrophobic. In such embodiments, the nanoparticle material is selected from PLA, PLGA and mixtures thereof.

In another one of its aspects, the invention provides a composition comprising a plurality of nanoparticles, as disclosed herein. In some embodiments, the composition is a pharmaceutical composition, and further comprising a pharmaceutically acceptable carrier.

The "pharmaceutically acceptable carriers" described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, parenteral, intravenous, intramuscular, or intraperitoneal administration are merely exemplary and are in no way limiting.

The pharmaceutical composition may be adapted for administration by a variety of routes including oral, rectal, vaginal, subcutaneous, intravenous, intramuscular, pulmonary, topical or dermal, eye drops and intranasal. Such pharmaceutical composition is prepared in a manner well known in the pharmaceutical art. In making the pharmaceutical composition of the invention, the aforementioned components are usually mixed with an excipient, diluted by an excipient or enclosed within such a carrier which can be manipulated to the desired form. Based on the particular mode of administration, the pharmaceutical composition may be formulated into tablets, pills, capsules, sachets, granules, powders, chewing gum, suspensions, emulsions, creams, ointments, anhydrous or hydrous topical formulations and solutions.

The pharmaceutically acceptable carriers, for example, vehicles, adjuvants, excipients, or diluents, are well-known to those who are skilled in the art and are readily available to the public. It is preferred that the pharmaceutically acceptable carrier be one which is chemically inert to the active formulation and each of its components and one which has no detrimental side effects or toxicity under the conditions of use.

The choice of carrier will be determined in part by the particular formulation of the invention, as well as by the particular method used to administer the composition. Accordingly, there is a wide variety of suitable formulations of the pharmaceutical composition of the present invention.

In some embodiments, the pharmaceutical composition is adapted as a delivery system for transporting a therapeutic agent, orally, parenterally or intravenous into the circulatory system (cardiovascular system) of a subject.

Formulations suitable for oral administration can consist of (a) liquid solutions, such as an effective amount of the nanoparticles, or composition comprising same, dissolved in diluents, such as water, saline, or juice (e.g. orange juice); (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active formulation in an inert base, such as gelatin and glycerin, or sucrose and acacia, emulsions, gels, and the like containing, in addition to the active formulation, such carriers as are known in the art.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (MB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

In some embodiments, the delivery system is adaptable for a facilitated targeted therapeutic delivery and controlled release administration of a therapeutically effective amount of the active agent.

As known, the "effective amount" for purposes herein may be determined by such considerations as known in the art. The amount must be effective to achieve the desired therapeutic effect, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, the effective amount depends on a variety of factors including the affinity of the ligand to the receptor, its distribution profile within the body, a variety of pharmacological parameters such as half life in the body, on undesired side effects, if any, on factors such as age and gender, and others.

The nanoparticle containing active material(s) according to the invention may be used as such to induce at least one effect, e.g., "therapeutic effect", or may be associated in conjugation with at least one other agent to induce, enhance, arrest or diminish at least one effect or side effect, by way of treatment or prevention of unwanted conditions or diseases in a subject. The at least one other agent (substance, molecule, element, compound, entity, or a combination thereof) may be selected amongst therapeutic agents, i.e., agents capable of inducing or modulating a therapeutic effect when administered in a therapeutically effective amount, and non-therapeutic agents, i.e., which by themselves do not induce or modulate a therapeutic effect but which may endow the nanoparticles with a selected characteristic, as will be further disclosed hereinbelow.

The pharmaceutical composition of the present invention may be selected to treat, prevent or diagnose any pathology or condition, depending on the active material contained within the nanoparticles. The term "treatment" or any lingual variation thereof, as used herein, refers to the administering of a therapeutic amount of the composition or system of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

In another aspect, the invention also provides a kit or a commercial package containing the composition of the invention as herein described, and instructions for use. In some embodiments, the composition of the invention or a fraction derived therefrom may be present in the kit in separate compartments or vials.

The kit may further comprise at least one carrier, diluent or solvent useful for the dissolution of the active components, the dilution thereof or generally for the preparation of the composition. The composition may be prepared by the end user (the consumer or the medical practitioner) according to the instructions provided or the experience and/or training of the end-user.

The kit may also comprise measuring tools for measuring the weight, volume or concentration of each component (active composition and/or carriers).

In another one of its aspects, the invention provides a process for obtaining the nanoparticle of the invention, as herein described, the process comprising:
- obtaining at least one nanocarrier, said nanocarrier comprising at least one active agent; and
- encapsulating said at least one nanocarrier into a nanoparticle.

Depending on the nature of the active agent (material) or plurality thereof to be contained in the system of the invention, the process of the invention may be carried out in a variety of equivalent forms. In general, the process comprises:
- selecting a polymer having hydrophobic or hydrophilic properties on the basis of whether the active agent is hydrophobic or hydrophilic, respectively;
- dissolving the polymer and the active agent in a liquid medium;
- treating said liquid medium comprising the polymer and active agent with a further liquid (where the liquid medium is organic, the further liquid is aqueous, and vice versa); and
- isolating said nanocarriers.

In some embodiments, where the active agent is hydrophobic, the nanocarrier material is hydrophobic and the nanoparticle material is hydrophilic, the process for preparing the nanoparticles of the invention comprises:
- dissolving a hydrophobic polymer in an optionally water-miscible organic solvent to form an organic phase; said organic solvent being selected, in some embodiments from ethanol, methanol, chloroform dichloromethane (DCM), diethyl ether, acetone and acetonitrile (ACN);
- contacting said organic phase with an aqueous phase, the aqueous phase optionally comprising a surfactant, to thereby obtain said nanocarriers; and
- incubating said nanocarriers with a solution of said active agent to allow association of said active agent with at least a portion of the surface of said nano carriers.

In some embodiments, the organic miscible solvent is selected from ethanol, methanol, chloroform dichloromethane (DCM), diethyl ether, acetone and acetonitrile (ACN).

As used herein, the term "contacting", or any lingual variation thereof, refers to the bringing together of the organic phase and the aqueous phase in such a way to allow intimate contact between them.

It should be noted, that the term "solution" should be given its broadest definition to encompass a liquid state in which one component is fully dissolved in another or in a liquid medium, a liquid state of emulsion (nano- or micro-emulsion) of one or more components of the precursor solution in another or in a medium, and a state of dispersion (nano- or microdispersion) of one or more components of the precursor solution in another or in a medium.

In some embodiments, where the active agent is hydrophilic, the nanocarrier material is hydrophilic and the nanoparticle material is hydrophobic, the process comprises:
- dissolving a hydrophilic polymer in an aqueous solution of the active agent to form an aqueous phase; and
- continuously adding an organic phase comprising a desolvating agent to the aqueous phase under a pH permitting the formation said nanocarriers, the active agent being distributed within the nanocarrier.

In some embodiment, the process optionally comprises cross-linking said hydrophilic polymer matrix.

In other embodiments, said pH is between 6 and 9. In some embodiments, the pH is 7.

In further embodiments, the desolvating agent is selected from acetone or ethanol, and acetonitrile.

The organic phase used in the process of the invention further comprises a positively charged lipid (cationic lipid), as define herein.

In all methods of preparing the nanoparticles of the invention, the final step of forming the nanoparticle coating around a plurality of nanocarriers may be achieved by nanospraying the nanocarriers into a solution comprising the nanoparticle polymer material. In accordance with other embodiments, said nanoparticles are obtained by encapsulation conducted in a nano-spray dryer.

In some embodiments, the process of the invention further comprises functionalizing at least a portion of the outer surface of said nanoparticle with at least one targeting moiety. In other embodiments, said at least a portion is the entire surface of the nanoparticle.

In some embodiments, said at least one targeting moiety is selected from PEG, trastuzumab (Herceptin®) recognizing HER-2 receptor overexpressed in solid tumors; AMBLK8 recognizing H ferritin; cetuximab (Erbitux®) recognizing EGFR receptors; Rituximab (MabThera®) recognizing CD20; bevacizumab (Avastin®) inhibiting the function of a natural protein called "vascular endothelial growth factor" (VEGF) that stimulates new blood vessel formation; ranibizumab (Lucentis®), providing stronger binding to VEGF-A; small molecules such as folic acid or folate; hyaluronic acid or hyaluronan; tumor penetrating peptides, typically about 6-15 kDa; epidermal growth factor (EGF); transferrin; ferritin; Arginine-Glycine-Aspartic acid (RGD) peptide; epithelial cell adhesion molecule (EpCAM); intercellular adhesion molecule 1 (ICAM-1); carcinoembrionic antigen (CEA); vasoactive intestinal peptide; CA 15-3 antigen; MUC1 protein; CD20; CD33; integrins; lymphatic targeting moieties (such as LyP-1); aptamers, such as PSMA aptamer or VEGF aptamer; oligosaccharides and others.

According to some embodiments, the targeting agent is bevacizumab (Avastin®) or ranibizumab (Lucentis®).

BRIEF DESCRIPTION OF THE DRAWINGS

In order to understand the disclosure and to see how it may be carried out in practice, embodiments will now be described, by way of non-limiting example only, with reference to the accompanying drawings, in which:

FIG. 2A: ultrafiltrate from formulations A and B—Lane No. 1—ladder, Lane No. 2 with 100 ng GFP-siRNA as control. Lanes 3, 4 are with 10 µl ultrafiltrate of A1 and A2 respectively. Lanes 5, 6 are with 4 µl ultrafiltrate of A3 and A4 respectively. Lanes 7, 8 are with 10 µl ultrafiltrate of B1 and B2 respectively. Lanes 9, 10 are with 4 µl ultrafiltrate of B3 and B4 respectively.

FIG. 2B: ultrafiltrate from formulations D and C: Lane No. 1—ladder, Lane No. 2 with 100 ng GFP-siRNA as control. Lanes 3, 4 are with 16 µl ultrafiltrate of C1 and C2 respectively. Lanes 5, 6 are with 16 µl ultrafiltrate of C3 and C4 respectively. Lanes 7, 8 are with 16 µl ultrafiltrate of D1 and D2 respectively. Lanes 9, 10 are with 16 µl ultrafiltrate of D3 and D4 respectively. In all samples numbers 1, 2 stands for duplicates from the formulation incubated with 50 µg GFP-siRNA and numbers 3, 4 stands for duplicates from the formulation incubated with 100 µg GFP-siRNA.

FIGS. 8A-8B: 1.6% HSA (200 mg) encapsulating 30 mg of negatively charged NSs of PLGA (ZP −33 mV). FIGS. 8C-8D: 0.75% HSA (56 mg) encapsulating 15 mg of positively charged NSs of PLGA (ZP +66 mV). FIGS. 8E-8F: 0.5% HSA (56 mg) encapsulating 14 mg of negatively charged NSs of PLGA (ZP −33 mV). FIGS. 8G-8H: 0.25% (28 mg) HSA encapsulating 7 mg of negatively charged NSs of PLGA (ZP −33 mV).

FIG. 12 is SEM micrograph of polymeric NCs encapsulating primary crosslinked HSA NPs.

DETAILED DESCRIPTION

Figure 1A:
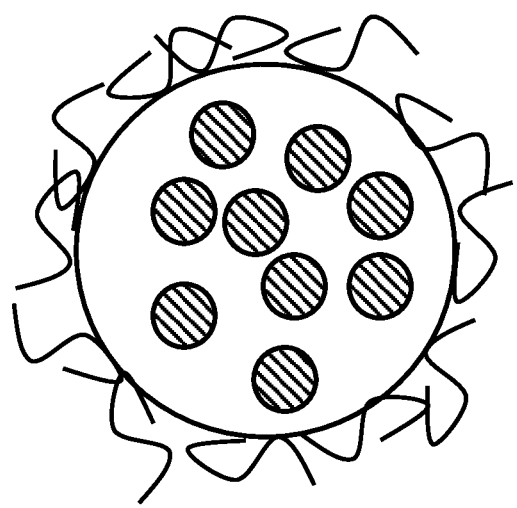
FIGS. 1A-1B are schematic diagrams of the nanospray dryer principle of action (FIG. 1B) and a nanoparticle obtained therefrom (FIG. 1A).

In the present invention, double nanoencapsulation is being used to protect and control the release of large hydrophobic or hydrophilic agents, such as siRNA. The first line of protection is achieved by loading the siRNA into primary nanocarriers (~100 nm), while the second line of stability is obtained by encapsulating the primary nanocarriers into sub-micron nanoparticles, typically with a polyethylene glycol (PEG) moiety anchored to their surface. The nanoparticles formation (typically nanocapsules, or NCs) is carried out using a nanospray drying technique [16, 23, 24].

The following two types of nanoparticles are herein described:

(a) PLGA (Poly D,L-lactic-co-glycolic acid) NPs loaded in nanocapsules were prepared using hydrophilic coating polymers; and (b) HSA (Human serum albumin) NPs loaded in nanocapsules were prepared using hydrophobic coating polymers.

In both cases, a cationic lipid, DOTAP (1,2-dioleoyl-3-trimethylammonium-propane), was added to the primary NPs to effectively load the negatively charged siRNA and to further facilitate 'endosomal escape' of siRNA after NPs cell internalization. Since all ingredients are FDA approved, such a delivery system provides a platform for systemic delivery of hydrophilic bio-macromolecules (such as siRNA) improving the drug's half-life, biodistribution and pharmacokinetics.

In drug delivery, nanoparticles (NPs) are favored over microparticles not only due to their ability to enhance drug efficacy, but to alter favorably the pharmacokinetic profile of the selected drug since they can be intravenously administrated. In addition, such nanosized systems are superior to microparticles in their penetration properties and targeting to specific cell types [12]. The targeting efficiency and prolonged circulation time of NPs are the two most important factors for their successful applications to drug delivery [13]. Targeting NPs can be active (through attachment of ligands specific for receptors at the cell target site, or passive. In passive targeting, the tendency of small NPs to accumulate in the solid tumor due to the phenomenon known as 'Enhanced Permeation and Retention' (EPR) effect is utilized [14]. Cellular uptake of NPs was found to be dependent on NP's size, geometry, charge and cell type. In general, particles smaller than 1 µm can be internalized into cells through several endocytotic pathways [13]. Furthermore, attachment of polyethylene glycol (PEG) moieties to the surface of NPs results in steric hindrance that leads to reduced aggregation and plasma protein adsorption (opsonization) as well as uptake by the reticuloendothelial system (RES)—while prolonging blood circulation time [15]. Finally, to protect from aqueous phase degradation and ensure stability of NPs upon long term storage, dry powdered formulations are required. Lyophilization (freeze drying), usually accompanied with the addition of cryoprotecting excipient or spray drying processes are the two major, well established procedures applied for such a purpose.

Figure 1B:
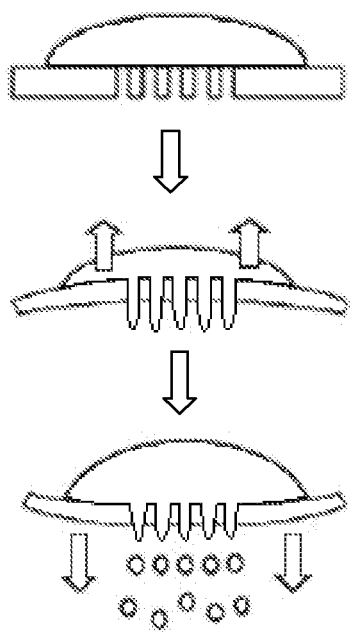

Spray drying is a process which converts liquids or suspensions into dry powders at a continuous single step process. However, this technique fails to efficiently form and collect fine particles <2 µm [16]. Recently, a new generation of laboratory scale spray dryers was developed by Buchi, enabling the generation of particles in the size range of 300 nm to 5 µm for small samples quantities (few milligrams or milliliters) at high yields (>70%). This technology allowed the formation of NPs by spray drying, resulting in the general structure shown in FIG. 1A which is a nanoparticle comprising a plurality of nanocarries, the nanocarriers comprising an active agent. This nanospray dryer (NSD), schematically illustrated in FIG. 1B, utilizes a vibrating mesh technology for fine droplets generation. Generally describing, a piezoelectric crystal driven spray head is incorporated with a small spray cap that contains a thin perforated membrane (spray mesh) having an array of precise micron-sized holes, which upon vibration, creates millions of sized droplets in range of 3-15 µm (typical median size of 5-7 µm, depending on the mesh size). Furthermore, unlike conventional spray dryers operating on turbulent flow, this new technology operates on a laminar flow; hence gentle heating is achievable, thus making the system compatible for heat-sensitive biopharmaceutical products.

Over the last decade, in addition to small molecular drugs, bio-macromolecules delivery, such siRNA is considered for therapy, using NPs/NCs as carriers. siRNA (small interfering RNA), a short sequence of RNA molecules (19-30 bp long duplexes) can be used to silence the expression of a specific gene, via inducing degradation on its complementary mRNA, in a well defined mechanism [17]. Since the discovery of siRNA, numerous attempts were made to develop drugs based on siRNA. However, major barriers arise in delivery of siRNA, due to its physicochemical nature. siRNA is a large (~13 kDa), hydrophilic, negatively charged molecule and as such requires transfection vehicles to penetrate the cell membrane and to gain access to the cytosol. Furthermore, after cell penetration (usually by endocytosis), an 'endosomal escape' mechanism is required. In addition, systemic delivery of free siRNA is hampered due to very short half-lives in the blood and fast renal clearance. To overcome these disadvantages in delivery of siRNA in-vivo, a variety of chemical modifications were introduced on the siRNA molecule, preserving its activity and thereby improving its resistance to RNAses cleavage and increasing its half-life in human serum [18]. In addition, naked or chemically modified siRNAs were incorporated in diverse delivery systems, based on non viral lipids (cholesterol, liposomes), protein carriers (fusogenic or cell-penetrating peptides), cyclodextrin or biodegradable polylactide copolymers nanoparticles with or without conjugation with cationic lipids.

The nanocarriers of the invention, without wishing to be bound by theory, provide protection, biocompatibility, improved stability, desired biodistribution and pharmacokinetics profiles to the encapsulated hydrophilic bio-macromolecule (i.e. siRNA), resulting in a unique delivery system with improved therapeutic properties.

Materials and Methods

Materials

PLGA: Poly (D,L-lactic-co-glycolic acid) (50:50) (R504H) MW 48,000 Da, and PEG-PLGA (RGP50105) MW 5,000+45,000 Da were purchased from Boehringer (Ingelheim, Germany). The following materials were purchased form the following companies: Dextran 40 (MW 40,000 Da), Teva (Jerusalem, Israel); Sodium Hyluronate (HA), MW 200,000 Da, Bioberica (Barcelona, Spain); DOTAP (1,2-dioleoyl-3-trimethylammonium-propane-chloride salt), MW 698.5 Da, Lipoid GmbH (Frigenstr, Germany); Commercial Human Serum Albumin (HSA) 20% solution for i.v. injection (Zenlab 20 or Biotest), Kamada (Beit-Kama, Israel) and supplied by Hadassah hospital. HAS, MW 66,500 Da, Macrogol 15 hydroxystearate (Solutol HS 15) obtained from BASF (Ludwigshafen, Germany). Polyethylene glycol (PEG) MW 4,000 Da, Polysorbate 80 (Tween 80), Gluteraldehyde 8% sol. in water, Trypsin (from porcine pancreas), RNase & DNase free Ultra pure water and Phosphate buffered saline (PBS) (Bioreagent, pH 7.4), were all purchased from Sigma (St. Louis, Mo., USA). Acetone, Ethanol, Dichloromethane, Chloroform, and Acetonitrile were all HPLC grade. Other chemicals and solvents were of analytical reagent grade and used without further purification. For all experiments done with siRNA only Ultra pure water was used (Sigma or Beit-Haemek), while for all the other blank systems (without siRNA), double-distilled water (DDW) was used throughout the study.

siRNA:

Anti EGFR (Epidermal Growth Factor Receptor) siRNA (EGFR-siRNA) (21 bp, MW 13,400 Da) and scrambled siRNA (21 bp, MW 13,821 Da), for control purpose were purchased from Ambion (Austin, Tex., USA).

```
EGFR-siRNA:
                                        (SEQ ID NO: 1)
  S (5'→3')  CCAUAAAUGCUACGAAUAUtt (SEQ ID NO: 2)
  AS (5'→3') AUAUUCGUAGCAUUUAUGGag scrambled siRNA:
                                        (SEQ ID NO: 3)
  S (5'→3')  UAACGACGCGACGACGUAATT
```

-continued

```
                                    (SEQ ID NO: 4)
AS (5'→3') UUACGUCGUCGCGUCGUUATT
```

In the above sequences, chemical modifications consisted of a few LNA modifications; lower case letter=DNA base.

Anti Green Fluorescent Protein (GFP) siRNA (GFP-siRNA) (21 bp, MW 14,352 Da), and Cholesterol modified GFP-siRNA (Chol-GFP siRNA) (21 bp, MW 15,079 Da), were provided by Roche (Kulmbach, GmbH) and were used for most of experiments (especially for estimation of drug loading).

```
GFP-siRNA:
                                    (SEQ ID NO: 5)
S (5'→3') AuAucAuGGccGAcAAGcAdTsdT (SEQ ID NO: 6)
AS (5'→3') UGCUUGUCGGCcAUGAuAUdTsdT

Chol-GFP siRNA:
                                    (SEQ ID NO: 7)
S (5'→3') (Chol)-linker-AuAucAuGGccGAcAAGcAdTsdT (SEQ ID NO: 8)
AS (5'→3') UGCUUGUCGGCcAUGAuAUdTsdT
```

In the above sequences, chemical modifications: lower case letter=2' O-methylated nucleoside, dT=desoxy-thyamin, sdT=desoxy-thyamin phosphorothioate, underlined=overhang.

```
Anti- EGFR -siRNA synthesized 'in house'
using EGFR-siRNA
                                    (SEQ ID NO: 9)
S* (5'→3') CCAUAAAUGCUACGAAUAUtt (SEQ ID NO: 10)
AS (5'→3') AUAUUCGUAGCAUUUAUGGtt
and (SEQ ID NO: 11)
S* (5'→3') CCAUAAAUGCUACGAAUAUtt (SEQ ID NO: 12)
AS (5'→3') AUAUUCGUAGCAUUUAUGGtt
```

In the above sequences, chemical modifications: underlined=2' O-methylated nucleoside, lower case letter=DNA base, *addition of (Chol)-linker or NIR dye molecule in the 5' position will also be made.

Methods and Experimental Methodology

PLGA NSs Preparation

Preparation of nanospheres was made based on the 'polymer interfacial deposition' method [19]. In brief, the polymer PLGA 48 kDa was dissolved in a water-miscible organic solvent (acetone). Then the organic phase was added rapidly and under stirring (~900 RPM) to the aqueous phase, which typically contains a surfactant (Solutol® HS 15). As a fast escape of acetone to the water phase occurs, the hydrophobic polymer spontaneously forms spherical negatively charged nanometric spherical particles (50-200 nm).

For formation of positively charged PLGA NSs, DOTAP (1,2-dioleoyl-3-trimethylammonium-propane-chloride salt) was added to the acetonic phase in different percentages. The formulations were evaporated (at 37° C.) to remove all acetone traces, and further concentrated to a final volume of 5 ml aqueous phase, then centrifuged for 10 min at 4,000 RPM (precipitation was removed and dried—found to be no more than 1% (w/w)), and washed (×10) with DDW using VivaSpin-6 (300 kDa, Vivascience) in order to reduce the percentage of Tween. The final percentage of each component in the washed formulation was: 1.5% (w/v) PLGA and 0%, 0.04%, 0.2% or 0.4% (w/v) DOTAP (Formulations A, B, D and C, respectively).

Size, Size Distribution and Zeta Potential Measurements of Primary NSs

Physicochemical characterization of primary NSs (made from PLGA or from crosslinked HSA) was measured by dynamic light scattering, using Zetasizer Nano ZS (Malvern Instruments, Malvern, UK). All samples were diluted 1:100 in HPLC grade water (pH=5.5) prior to measurements. When siRNA loaded NSs were characterized, RNase free water with 0.01% NaCl was used (pH=5.5).

Loading Efficacy of siRNA in PLGA NSs

For incubation with siRNA, the formulation were made at the same manner detailed above, but instead of using water (HPLC grade) as aqueous phase, RNase free water (RNFW) were used for formation and washing steps. Briefly, 0.1 ml of washed PLGA NSs were taken from each formulation (1.5 mg PLGA content) and incubated with different amounts of GFP-siRNA (50 µg, 100 µg) for 1 hr with mild shaking at room temp. After incubation each formulation was washed (×10) with RNFW (using 300 kDa Nanosep centrifugal centricones, Pall) and the total ultrafiltrate was collected, lyophilized and reconstituted with 500 µl RNFW, from which, 150 µl were injected to HPLC. GFP-siRNA content in the ultrafiltrate was calculated based on calibration curves made by reversed phase HPLC (RP-HPLC).

High-Pressure Liquid Chromatography (HPLC)

Calibration curves for the different siRNAs used were made using HPLC (Shimadzu LC-2010C) with a Clarity 3 um Oligo-RP column 50×4 6 mm (Phenomenex, USA). The siRNA was dissolved in RNFW or in RNF buffer (100 mM NaCl, 50 Mm Tris), prior to injection. Mobile phase: A-RNase free Buffer (100 mM TEAA), B-Acetonitrile. Long Gradient (for Cholesterol modified siRNA): B/A (10:90) to (90:10) in 40 min, then another 10 min of B/A (10:90). Short Gradient (for none Cholesterol modified siRNA): B/A (10:90) to (40:60) in 15 min, then another 10 min of B/A (10:90). Flow rate: 1 ml/min, UV-Detection: 260 nm and 280 nm.

Gel Electrophoresis with Polyacrylamide Gel (PAGE)

For siRNA integrity (stability) evaluation 8% (19:1) native polyacrylamide gels (PAGE) was used. Electrophoresis was carried out at 200V for 50 min, in Tris-Borate-EDTE (TBE) as running buffer. For siRNA staining, 0.01% of EtBr was used. Gels were visualized under a UV transilluminator.

Protocol for Evaluation of Loading Efficacy of GFP-siRNA on PLGA NSs

PLGA NSs are dissolved in chloroform until a clear solution forms, followed by the addition of an equal volume of RNFW. Samples are vortexed and centrifuged (5 min at 4,000 RPM). The upper aqueous phase (with free siRNA) is collected. This procedure is repeated twice. Next, the collected aqueous phase is lyophilized. Determination of siRNA content is assessed by RP-HPLC, after reconstitution of lyophilized samples in RNF buffer. Since NSs with DOTAP and siRNA may form an 'ion-pair', addition of heparin (highly negative charged molecule) to aqueous phase is examined, following an incubation for 1 hr at 37° C., under mild shaking, in order to ensure that all siRNA is released in its free form.

Primary Crosslinked HSA NSs Preparation

Prior to use, commercial HSA was desalted for 24 hr in DDW using a cellulose membrane (MWCO 14,000) from Medicell International (Liverpool road, London), in order to remove salts and all preservative traces. In order to produce nanometric HSA NPs, the well known method of pH-coacervation [20] (also known as desolvation technique) was applied. Briefly, HSA solution, adjusted to a specific pH, was transformed into nanospheres by continuous (~1 ml/min) addition of desolvating agent, under constant, rapid stirring (~960 RPM or 40 HZ) at room temp. Addition of desolvating agent was continued until sufficient turbidity appeared (usually between 40 to 80% (v/v) of desolvating agent), then the crosslinking process was carried out with glutaraldehyde for at least 2 hr at room temperature under milled shaking. After crosslinking, desolvating agent was evaporated (37° C.) and centrifuged for 10 min at 4,000 RPM (precipitation was removed, dried and determined gravimetrically). NSs were washed (×10) with DDW, at three different cycles of centrifugation (4,000 RPM, 4° C.), using vivaspin 300 kDa (Viva science). In some cases acetone phase contained DOTAP.

Loading Efficacy of siRNA on Crosslinked HSA NSs

For encapsulation of siRNA inside crosslinked HSA NSs, siRNA was added to HSA solution prior the addition of desolvating phase. The rest of procedure was made exactly in the same manner detailed above, when instead of using DDW, RNAse free water (RNFW) was used. After crosslinking, the NSs were washed and the total ultrafiltrate was collected, lyophilized and reconstituted with 500 µl RNFW, from which, 160 ul were injected to HPLC. Since partial degradation of free siRNA in the ultrafiltrate was observed, the preferred way to determine siRNA content in the NSs is to directly determine siRNA content in the particle (after its digestion), and not based on the free siRNA (un-encapsulated) in the ultrafiltrate.

A Protocol for Determination of siRNA Content in the Crosslinked HSA NSs

The total weight of HSA per 100 µl of suspension (after wash) was quantified gravimetrically. Then 1-2 mg of washed HSA NPs encapsulating siRNA was diluted to 1 ml with RNase free PBS buffer (adjusted to pH=7.5 using 0.5 M NaOH solution) and digested with 20 to 150 µg Trypsin for 60, 90 or 180 min, at dark and under mild shaking at 37° C., till a clear solution was formed. In case sample containing DOTAP, Heparin (90 µg) was added to the aqueous phase, 0 or 60 min after the addition of Trypsin. The free siRNA quantity was determined using RP-HPLC, in the presence of Trypsin or without it.

The Trypsin as well as the fragments of digested HSA can be removed by precipitation using (phenol/chloroform) (1:1) mixture.

Encapsulation of PLGA NSs into NCs Using Nanospray Dryer—Aqueous Mode

NCs were prepared via spray drying on the Nano Spray Dryer B-90 (BÜchi Labortechnik AG, Flawil, Switzerland), operating at 'open loop' mode, hence air was flowing through the system. In all experiments gas flow was about 120 l/min 100% spraying and 4 µm mesh size membrane were used in all experiments.

Encapsulation of HSA NSs into NCs Using Nanospray Dryer—Organic Mode

NCs were prepared via spray drying on the NSD B-90 operates at 'closed loop' mode, hence, $N_2$ (g) and $CO_2$ (g) are flowed in the system instead of air. In all experiments gas flow was about 120 l/min. The air soaked with volatile vapors and humidity, transferred to a Dehumidifier unit, for drying and condensation, then returned dry to the system in a circular path. Spray drying was carried out at low temperatures (Tin=30°-60° C.) with mesh size membrane 4 µm.

Melting Point Measurements for siRNAs

Melting point measurements for different siRNAs (21-mer) used were performed on a UV-visible spectrophotometer (Cary 300) at 260 nm, by elevating the sample temperature from 20° C. to 85° C. at rate of 1° C./min. All siRNAs were dissolved in buffer (48 mM Tris, 96 mM NaCl, pH 7.1) to obtain a concentration of 4-10 ng/µl.

Thermal Analysis by Differential Scanning Calorimeter (DSC)

DSC measurements were made for the polymers (PLGA 48 kDa and PEG-PLGA 50 kDa), and performed at a temperature range of −20° C. to 220° C. using a Mettler DSC 1 Star System (calibrated with In standards) at a heating rate of 10° C./min, under a nitrogen atmosphere.

SEM (Scanning Electron Microscope) and EDS (Energy Dispersive X-Ray Spectroscopy)

Geometry, size and surface morphology of the spray-dried NCs (and encapsulated NSs) were observed by a High Resolution Scanning Electron Microscope (HR-SEM) with High stable Schottky Field Emission Source (Sirion, model: Quanta 200 FEI, Germany), 5 kV. Prior to imaging, the samples were dispersed onto carbon sticky tabs and coated with gold and palladium mixture for 90-120 sec. In case of primary NSs dispersed in water, the samples were highly diluted, then spattered on glass and left to evaporate overnight. Element analysis of the specimen was made by EDS (Energy Dispersive X-ray Spectroscopy), with X-MAX20 SDD Inca 450 EDS LN2 free detector (Oxford Instruments, UK), using low voltage of 5 kV, with spectral resolution of 129 eV.

A Method for Evaluation of Size Distribution for Spray Dried NCs

Since the regular Zetasizer Nano ZS is limited for measurements of particles smaller than 4 µm as well as for relatively homogeneous dispersions, a sufficient particle size distribution for the spray dried NCs can only be made by means of laser diffractometry using a Mastersizer 2000E (Malvern Instruments, UK). Approximately 4 mg of sample was needed for each measurement in order do disperse it at 120 ml of dispersant.

Span value was calculated by:

$$\mathrm{Span}=(d90-d10)/d50$$

wherein d50 was the volume median size; d90, 90% of the volume had a size smaller than d90; d10, 10% of the volume had a size smaller than d10.

Low Span Value Indicated a Narrow Size Distribution.

A Protocol for Determination of the Spray Drying Encapsulation Efficacy

For separation between different NCs populations by size, size exclusion chromatography (SEC) was applied. Then, in order to determine the content of HSA NSs encapsulated inside a specific population of large PLGA NCs, first desolvation of the PLGA NCs in chloroform was made. Then, upon centrifugation (10,000 RPM, 15 min) the primal HSA NPs was separated as sediment, isolated and its content was validated by Bicinchoninic Acid (BCA) Protein Assay kit or by the nitrogen content (detected by simple microanalysis). For HSA NCs encapsulating primary PLGA NPs, NCs with known weight was degraded upon incubation with aqueous solution of Trypsin (PBS buffer pH of 7.5 at 37° C.), then HSA content was quantified using BCA and the PLGA quantity was estimated by subtraction. When NCs encapsulating primary NSs loaded with siRNA, the total content of isolated siRNA was determined (after NCs disassembling and NSs digestion).

In-Vitro Release Kinetic Profile Determination of EGFR-siRNA

The kinetic profile for EGFR-siRNA released from primary NSs and secondary NCs, will be determinate in-vitro, in the same manner detailed at Hagigit et al. [21]

Cell Culture

A-431 human epithelial squamous carcinoma cells and other colorectal carcinoma cells, will be maintained in Dulbecco's Modified Eagle's Medium (DMEM) containing 10% fetal bovine serum, 2 mM L-glutamine and 10000 U/ml penicillin and 100 ug/ml streptomycin. The medium will be replaced every two days. The cells will be grown at 37° C., 6% $CO_2$ in a $CO_2$ incubator. Confluent flasks will be splitted at 1:10 ratio after trypsinization of the cultures with 0.25 ml Trypsin solution (Beit Haemek, Afula, Israel). All experiments will be carried out in a clean room according to ISO7 requirements (10000 particles/$m^3$).

NPs Stability in Cell Culture Medium

Size measurements, using Zetasizer Nano ZS will be made for the NSs, after different times of incubation in A-431 cell culture medium, in the same manner as detailed at [22].

NCs Stability Evaluation

Size measurements using Mastersizer X, and morphology evaluation using SEM, will be made for the final NCs after storage in different conditions (4 and 37° C.) for 4, 8 and 12 weeks.

NPs Cytotoxicity in A-431 Cells

The cell proliferation will be tested over a time period of 144 h, in the presence of 5, 1, 0.1 and 0.01 mg/ml NPs concentration per well, in the same manner described at [21].

Uptake of FITC-Labeled HSA NSs in A-431 Cells

In order to produce a 2% FITC-labeled HSA NSs, 1.9 mg of FITC-BSA (Bovine Serum Albumin) was added to 4 ml of 2% HSA solution. The particles were made in the same way as detailed previously, just under dark. The washed NSs were then filtrated through cellulose acetate sulphonate filter (0.2 um, Whitman). Next, aliquots of the FITC-labeled HSA NPs (61.2 µl and 122.45 µl) were diluted in DMEM buffer into a total volume of 1.5 ml, in order to produce concentrations of 1 mg/ml and 2 mg/ml, respectively, per well. For cell labeling, 150,000 A-431 cells were placed on cover slides and left overnight to adhere. The following day the adherent cells were incubated with the aliquots of FITC-labeled HSA NSs for 4 h or 22 h, followed by three washes with phosphate buffered saline (PBS). Thereafter the cells were fixed with 4% paraformaldehyde (Sigma-Aldrich) and washed three times with PBS. In the negative control experiments, the FITC-labeled HSA NSs incubation step was omitted while the other steps remained the same. The cells were examined in a FluoView FV300 confocal laser scanning microscope (Olympus, Tokyo, Japan).

Evaluation of Anti EGFR-siRNA Silencing Efficacy in A-431 Cells Using an In-Cell NIR Model Anti EGFR-siRNA silencing efficacy will be performed based on the novel method developed and detailed in Cohen et. al [23]. Knockdown efficacy of EGFR mRNA will be confirmed by RT-PCR (Reverse Transcription-Polymerase Chain Reaction) using relevant primers and EGFR protein levels will be quantified by western blotting.

Xenograft Tumor Studies in Mice

A-431 tumor cells will be cultured. Subconfluent cells (70%-80%) will be harvested after brief treatment with 0.25% trypsin and resuspended in Hank's balanced salt solution for inoculation. Tumor cell suspensions ($3-5\times10^6$ cells) will be injected SC in a volume of 0.2 ml into the right flank of each mouse. 8 to 10 mice will be randomly assigned to each treatment group, and treatments will be conducted for up to 4 weeks. The doubled nanovehicle will be injected in the jugular vein, at the appropriate dosage. Tumor measurements will be made periodically with manual calipers (at least once a week), and tumor volumes will be calculated using the formula: $0.52 \times length \times width$. At the end of the study, tumors will be excised and weighed, and then for some studies. In parallel the tumors will be bioimaged noninvasively with NIR labeled EGF probe.

Results

PLGA NSs Preparation in Organic Phase

The first type of primary NSs were prepared from PLGA 48 kDa (Poly D,L-lactic-co-glycolic acid, 50:50), with or without addition of cationic lipid (DOTAP), producing negatively or positively charged NSs. The NSs were prepared using the well established technology of 'polymer-interfacial deposition' method. Four different blank formulations were selected in order to test siRNA loading efficacy through interfacial interactions (electrostatic & hydrophobic). The four formulations (see Table 1), differ in their DOTAP content (Formulations A, B, D and C, containing 0%, 0.04%, 0.2%, and 0.4% (w/v) of DOTAP, respectively).

Physicochemical Characterization

Physicochemical characterization for the PLGA NSs was made, prior and after incubation (1 hr at room temp.) with GFP-siRNA (50 and 100 µg). The results are detailed in Table 1.

Based on these results, GFP-siRNA adsorption is clearly observed, leading to a change in the physicochemical nature of the NSs (ZP, PDI and size). While ZP for negatively charged NPs (formulation A) remained negative, formulation B changes from the slightly positive to negative even with 50 µg of GFP-siRNA. For NSs with a pronounced positive charge (formulations D and C-ZP above 40 mV) we observe a decrease in ZP; particularly for formulation D.

TABLE 1

Physicochemical characterization for the PLGA NSs, prior and after incubation (1 hr at room temp.) with GFP-siRNA

| Formulation | Conditions of measurement | Mean diameter [nm] | Mean ZP [mV] | PDI |
| --- | --- | --- | --- | --- |
| A | No incubation with siRNA | 68.8 ± 22.1 | −28.6 ± 14.8 | 0.10 |
|   | After incubation with 50 µg GFP-siRNA and washing | 78.1 ± 39.5 | −25.8 ± 10.7 | 0.21 |
|   | After incubation with 100 µg GFP-siRNA and washing | 88.9 ± 44.5 | −27.8 ± 10.7 | 0.17 |
| B | No incubation with siRNA | 103.1 ± 32.7 | +11.2 ± 9.9 | 0.09 |
|   | After incubation with 50 µg GFP-siRNA and washing | 124.0 ± 56.7 | +44.0 ± 7.0 | 0.12 |
|   | After incubation with 100 µg GFP-siRNA and washing | 226.7 ± 98.5 | +2.2 ± 4.0 | 0.34 |
| C | No incubation with siRNA | 119.9 ± 46.7 | +49.7 ± 10.6 | 0.16 |
|   | After incubation with 50 µg GFP-siRNA and washing | 145.5 ± 62.0 | +45.8 ± 7.0 | 0.16 |
|   | After incubation with 100 µg GFP-siRNA and washing | 204.7 ± 114.2 | +44.4 ± 7.4 | 0.22 |

Polydispersity of size distribution (PDI), mean hydrodynamic diameter and Zeta potential (ZP), N=3, of negatively or positively charged primary PLGA NSs before and after incubation with GFP-siRNA. Incubation was done in duplicates.

Effective Loading of siRNA on Primary PLGA NSs

In order to determine the loading efficacy of siRNA after incubation with the different PLGA NSs, NSs were washed and the content of unbound siRNA in the collected ultrafiltrate was quantified by RP-HPLC (Table 2). The percent of siRNA associated with the NSs was calculated from the difference of the total siRNA (used for incubation), to that of free siRNA in the ultrafiltrate.

Figure 2A:
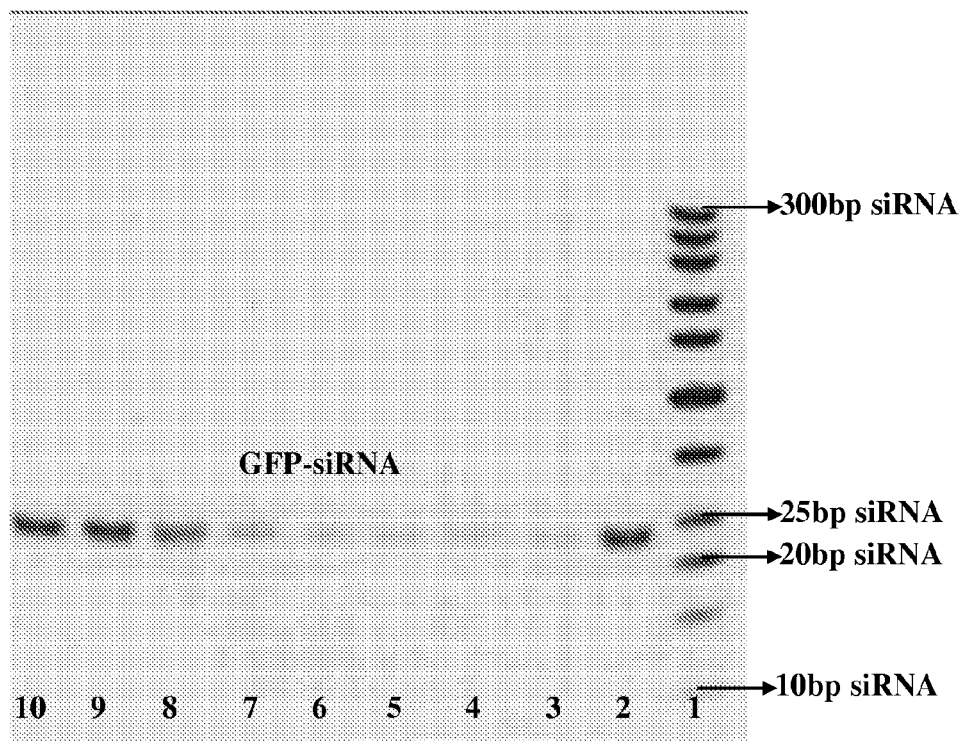
FIGS. 2A-2B are integrity evaluations by gel retardation assay (PAGE 8%) for GFP-siRNA from ultrafiltrate of washed PLGA NSs, after 1 hr of incubation.
Figure 2B:
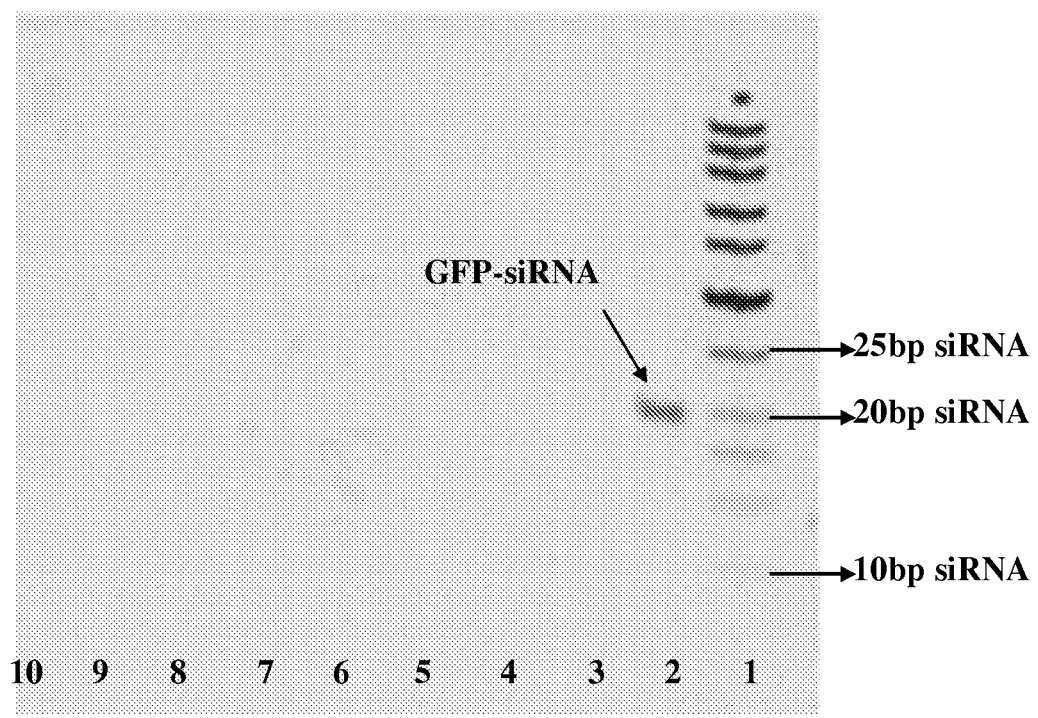

According to Table 2, in formulations containing 0.2% (w/v) of DOTAP and above (formulations C and D) full siRNA adsorption occurs. These results demonstrate that positive Zeta potential of ~50 on the PLGA NSs surfaces, induces strong and efficient adsorption of 100 ng siRNA per 1.5 mg of NSs. Insufficient loading occurs with slightly positive NSs (formulation B) and intermediate values occur for negatively charged NSs (formulation A). These results are further validated by gel retardation assay (PAGE 8%) (FIG. 2) showing no free siRNA is found in the ultrafiltrate of formulations C and D (on the contrary to the free siRNA detected in the ultrafiltrate of formulations A and B).

TABLE 2

Loading efficacy of GFP-siRNA on 1.5 mg of PLGA NSs.

| For-mula-tion | Quantity of GFP-siRNA used for incubation [µg] | Calculated average of free GFP-siRNA at total ultrafiltrate | | Calculated average of GFP-siRNA adsorbed to PLGA NPs | |
|---|---|---|---|---|---|
| | | Quantity [µg] | Percentage [%] | Quantity [µg] | Percentage [%] |
| A | 50 | 16.4 ± 0.8 | 32.7 ± 4.7 | 33.7 ± 1.6 | 67.3 ± 4.7 |
|   | 100 | 56.6 ± 2.8 | 56.6 ± 4.9 | 43.4 ± 2.1 | 43.4 ± 4.9 |
| B | 50 | 28.8 ± 3.8 | 57.5 ± 13.2 | 21.3 ± 2.8 | 42.5 ± 13.2 |
|   | 100 | 79.8 ± 3.0 | 79.8 ± 3.7 | 20.2 ± 0.8 | 20.2 ± 3.7 |
| C | 50 | ND | ND | *50 | *Above 99 |
|   | 100 | ND | ND | *100 | *Above 99 |
| D | 50 | ND | ND | *50 | *Above 99 |
|   | 100 | ND | ND | *100 | *Above 99 |

(*Based on calibration curves, the minimum amount of siRNA needed for detection through RP-HPLC is 360 ng (0.7% of 50 µg), hence, the percent of siRNA associated can be determined only in 99.3% accuracy. ND—not detected.)

The observation that formulation B shows poor loading capacity, can be explained by its low stability and tendency to aggregate (typical for particles with ZP value smaller than 20 mV). No fragmentation of the free siRNA was observed in HPLC chromatograms or upon evaluation by gel retardation assay (PAGE 8%), see FIG. 2.

HSA NSs Preparation in Aqueous Phase

Primary NSs ~100 nm, made from crosslinked HSA (Human Serum Albumin) were examined. The method of pH-coacervation was applied for this purpose. By changing different parameters (pH, type and quantity of desolvating agent used (ethanol or acetone), % HSA in solution and stirring speed) control the size of the formed NSs was achieved. The best results were obtained at 2% HSA solutions when acetone was used as desolvating agent. Selected results are shown in Table 3 and indicate that the smallest particles were obtained with acetone at pH 7 and 9.

TABLE 3

Physicochemical characterization for the HSA NPs (*Massive sediment appeared (64%(w/w)). In other samples sediment was negligible).

| Sample | pH | Desolvating agent | Total acetone added [ml] | Mean diameter [nm] | Mean ZP [mV] | PDI |
|---|---|---|---|---|---|---|
| 1* | 7 | Ethanol | 10 | 241 ± 71 | −35 ± 5 | 0.07 |
| 2 | 8 | Ethanol | 10 | 166 ± 44 | −35 ± 8 | 0.05 |
| 3 | 9 | Ethanol | 7 | 152 ± 43 | −51 ± 8 | 0.06 |
| 4 | 7 | Acetone | 10 | 58 ± 30 | −38 ± 9 | 0.24 |
| 5 | 8 | Acetone | 21 | 131 ± 55 | −36 ± 7 | 0.14 |
| 6 | 9 | Acetone | 9 | 61 ± 25 | −54 ± 10 (53%) −37 ± 8 (25%) | 0.13 |

Physicochemical Characterization

Figure 3A:
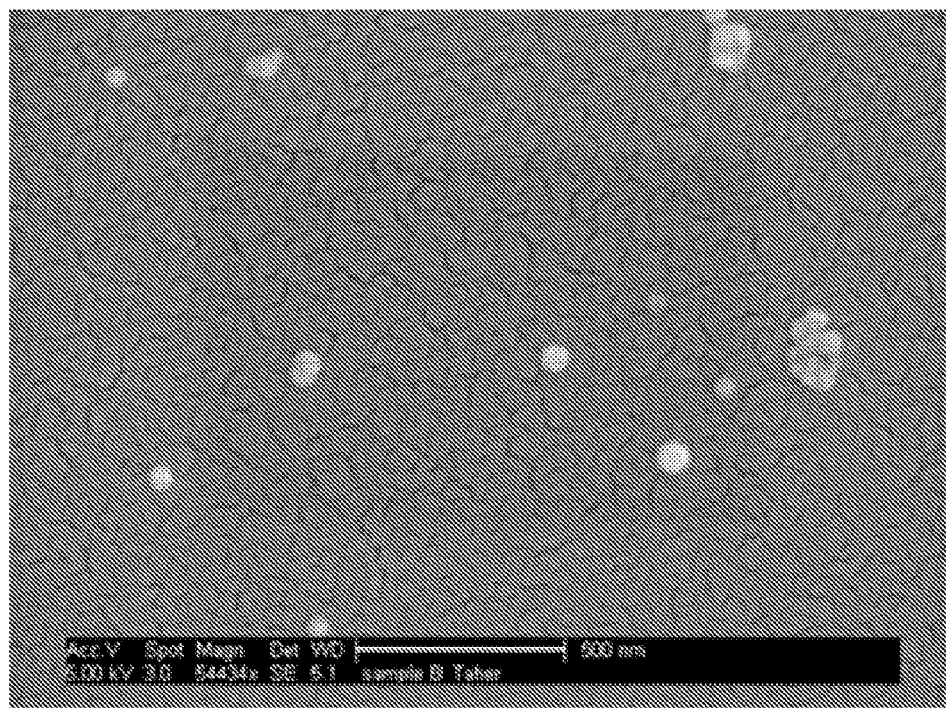
FIGS. 3A-3B are SEM characterizations of highly diluted crosslinked HSA NSs (mean size 58±30 nm, ZP −38±9).
Figure 3B:
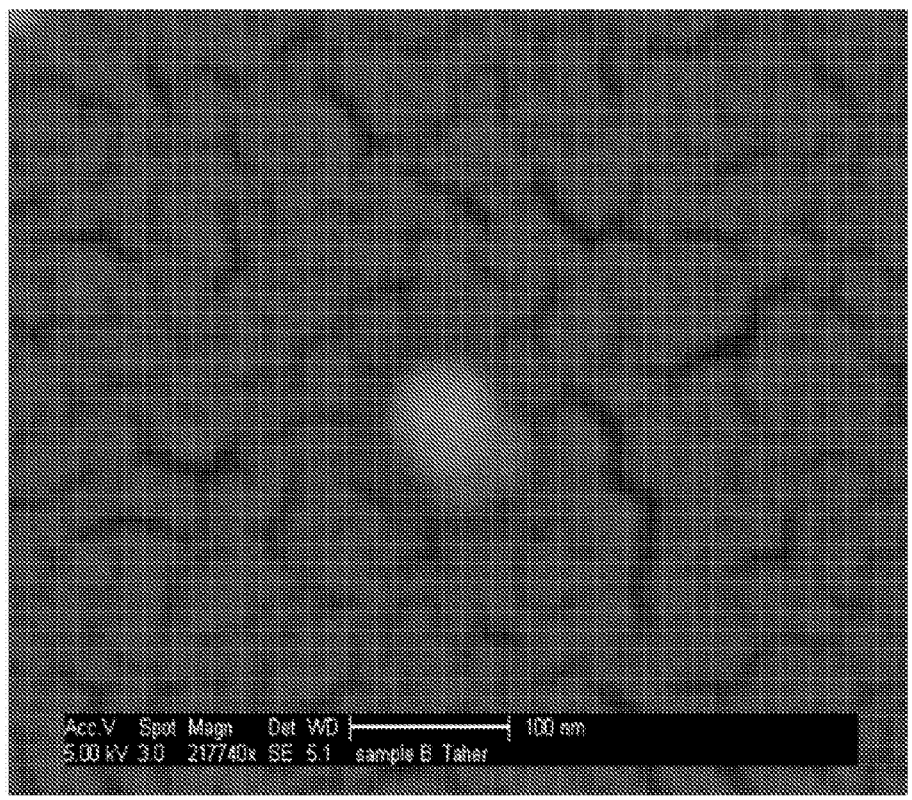

The physicochemical characterization for the crosslinked HSA NSs, shows that small, spherical and negatively charged NSs were formed, and their size distribution (from 40 to 300 nm) and polydispersity, are influenced by the pH and type of desolvating agent (Table 3 and FIGS. 3A-3B). In all pH tested, acetone produced smaller NSs with higher PDI values compared to ethanol.

Polydispersity of size distribution (PDI), mean hydrodynamic diameter and Zeta potential (ZP), N=3, of primary crosslinked HSA NSs prepared from 4 ml (2% HSA solution) at different pH with acetone or ethanol as desolvating agent, stirred at ~960 RPM.

The isoelectric point of HSA is about 5.0. As the pH of the aqueous solution is more basic, we gain more negatively charged carboxylic group on its surface that repels HSA molecules. Based on this idea, the smaller particles (~100 nm) are formed at pH 9. However, by utilizing the process described above, HSA NSs at the required size were obtained already at pH 7, by using acetone instead of ethanol (Table 3).

Effective Loading of siRNA in Primary HSA NSs

To encapsulate siRNA effectively inside the crosslinked HSA NSs, a scaling down process was made, requiring additional adjustment of parameters; working with 0.6 ml of 2% HSA solution instead of 4 ml. In addition, the cationic lipid DOTAP ('endocytosic agent') was also added to increase siRNA encapsulation efficacies. Blank systems (without siRNA) displayed in Table 4, showed that in some cases massive sediment appeared together with the formation of NSs. The best results obtained at pH 8 and 9 (samples 5, 9 and 10)—small NSs formed with the lowest sediment percentage.

TABLE 4 loading of siRNA in primary HAS NSs

| Sample | pH | DOTAP | Total acetone added [ml] | Mean diameter [nm] | Mean ZP [mV] | PDI | Sediment % [w/w] |
|---|---|---|---|---|---|---|---|
| 1 | 6.6 | − | 1.5 | 155 ± 55 | −36 ± 9 (78%) 0.7 ± 4 (18%) | 0.12 | 90 |
| 2 | 6.6 | + | 0.5 | 276 ± 156 | −44 ± 5 | 0.26 | 81 |

TABLE 4-continued loading of siRNA in primary HAS NSs

| Sample | pH | DOTAP | Total acetone added [ml] | Mean diameter [nm] | Mean ZP [mV] | PDI | Sediment % [w/w] |
|---|---|---|---|---|---|---|---|
| 3 | 7.3 | − | 1.5 | 139 ± 43 | −41 ± 8 | 0.08 | 54 |
| 4 | 7.3 | + | 1.5 | 129 ± 55 | −43 ± 8 | 0.16 | 60 |
| 5 | 8 | − | 1.5 | 80 ± 28 | −43 ± 10 | 0.13 | 21 |
| 6 | 8 | + | 1.5 | 90 ± 36 | −48 ± 11 | 0.13 | 43 |
| 7 | 8 | − | 2.4 | 228 ± 143 | −19 ± 5 | 0.24 | <1 |
| 8 | 8 | + | 2.4 | 3587 ± 330 | −7 ± 3 | 0.29 | <1 |
| 9 | 9 | − | 1.5 | 135 ± 62 | −63 ± 7 (50%) −36 ± 9 (50%) | 0.26 | 1 |
| 10 | 9 | + | 1.5 | 79 ± 43 | −28 ± 6 | 0.26 | 11 |

Based on these findings, encapsulation of 200 µg siRNA was also performed in basic pH (Table 5).

TABLE 5 loading of siRNA in primary HAS NSs, 200 µg siRNA

| Sample | pH | DOTAP | siRNA type | Total acetone added [ml] | Mean diameter [nm] | Mean ZP [mV] | PDI | Sediment % [w/w] |
|---|---|---|---|---|---|---|---|---|
| 1 | 9 | − | GFP | 1.5 | 107 ± 31 | −52 ± 6 (63%) −31 ± 8 (37%) | 0.07 | 8 |
| 2 | 9 | − | Chol-GFP | 1.5 | 109 ± 39 | −34 ± 8 (68%) −62 ± 5 (32%) | 0.13 | 15 |
| 3 | 9 | + | GFP | 1.5 | 88 ± 30 | −33 ± 9 (90%) −28 ± 5 (10%) | 0.1 | 33 |
| 4 | 9 | + | Chol-GFP | 1.5 | 113 ± 32 | −42 ± 9 | 0.07 | <1 |
| 5 | 8 | + | GFP | 1.5 | 81 ± 32 | −35 ± 8 | 0.23 | <1 |
| 6 | 8 | + | Chol-GFP | 1.5 | 119 ± 53 | −37 ± 7 | 0.34 | <1 |
| 7 | 8 | + | GFP | 2.4 | 171 ± 90 | −23 ± 5 | 0.32 | <1 |
| 8 | 8 | + | Chol-GFP | 2.4 | 88 ± 33 | −19 ± 6 (40%) −48 ± 7 (40%) | 0.14 | <1 |
| 9 | 7 | + | GFP | 1.5 | 93 ± 39 | −43 ± 6 | 0.14 | 0 |
| 10 | 7 | + | Chol-GFP | 1.5 | 93 ± 39 | −23 ± 8 (70%) −39 ± 6 (30%) | 0.13 | 0 |

Addition of desolvating agent in high volumes (70-80% (v/v)) was made to promote HSA NSs formation, but also to induce a sufficient siRNA encapsulation. Another strategy to obtain high encapsulation, was to include the lipophilic derivate of GFP-siRNA (5'-Cholesteryl-GFP-siRNA, i.e. Chol-GFP-siRNA). The results detailed in Table 5 indicate that at pH 8 and 7, with samples containing DOTAP, addition of siRNA (GFP or Chol-GFP), reduced dramatically the appearance of sediment (as observed in the blank samples upon addition of 1.5 ml of acetone—Table 4). At pH 9, the same phenomenon was seen only when Chol-GFP-siRNA was used.

Polydispersity of size distribution (PDI), mean hydrodynamic diameter and Zeta potential (ZP), N=3 and weight percentage of sediment evolved upon formation of primary crosslinked HSA NSs, prepared from 0.6 ml (2% HSA solution) at different pH with different amounts of acetone. (+/−) refers to acetone phase with 0.03 mg DOTAP or without DOTAP (α-acetone phase with 0.015 mg DOTAP).

Physicochemical characterization of primary crosslinked HSA NSs made with acetone upon encapsulation of 200 µg of GFP-siRNA or Chol-GFP-siRNA. (+/−) refers to acetone phase with 0.03 mg DOTAP or without DOTAP. Molar ratio of DOTAP:siRNA is 3:1.

Figure 4A:
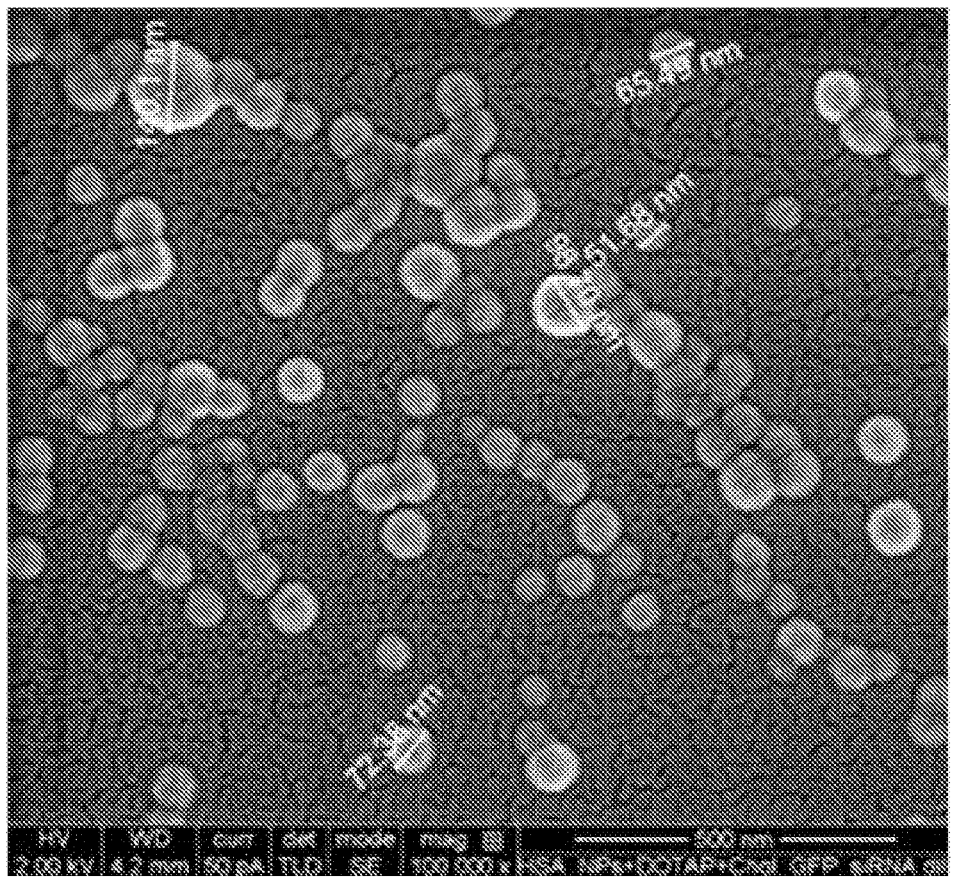
FIGS. 4A-4B are SEM characterizations of highly diluted crosslinked HSA NSs with 0.03 mg DOTAP, encapsulating siRNA (FIG. 4A: NSs with Chol-GFP-siRNA, FIG. 4B: NPs with GFP-siRNA).
Figure 4B:
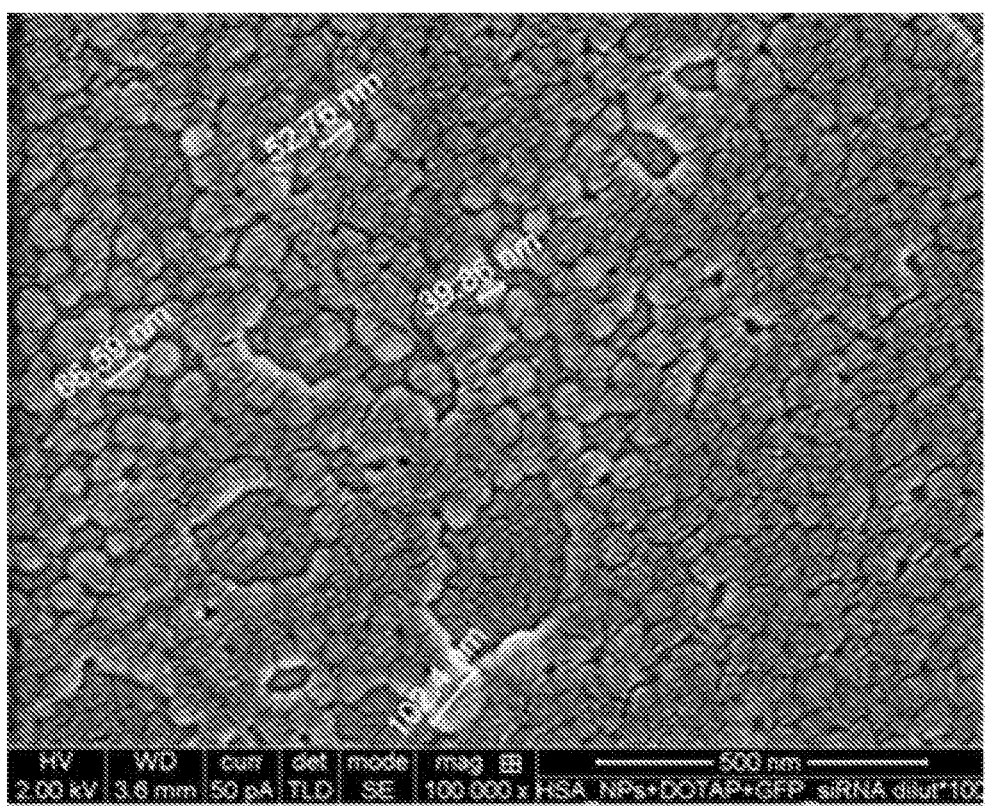

SEM characterization was made to the new crosslinked HSA NSs (loaded with DOTAP and siRNA) (FIGS. 4A-4B). It is clearly seen that the addition of DOTAP, as well as the encapsulation of siRNA (GFP or Chol-GFP), did not change the spherical shape of the formed NPs, already observed for the blank system (FIG. 3).

Figure 5:
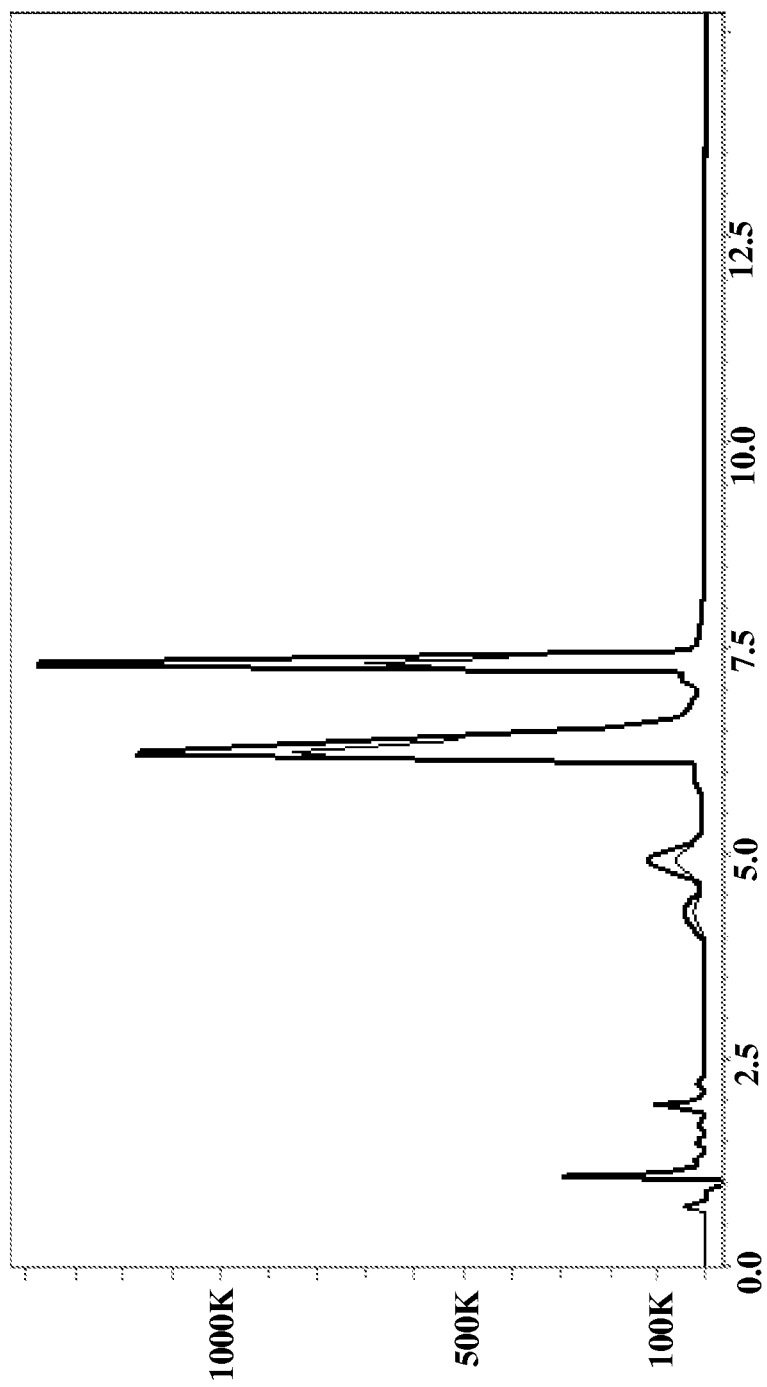
FIG. 5 is an HPLC chromatogram for GFP-siRNA extracted from crosslinked HSA NSs made with 0.03 mg DOTAP and 200 μg siRNA at pH 8 and untreated GFP-siRNA control, injected at the same gradient. The thick line is for absorbance at 260 nm and the thin line for absorbance at 280 nm. For siRNA (unlike proteins or peptides) the ratio $A_{260/280}$ is in the range of 1.8 to 2. The peak at app. 7.5 is attributed to the presence of GFP-siRNA extracted from crosslinked HSA NSs.
Figure 6:
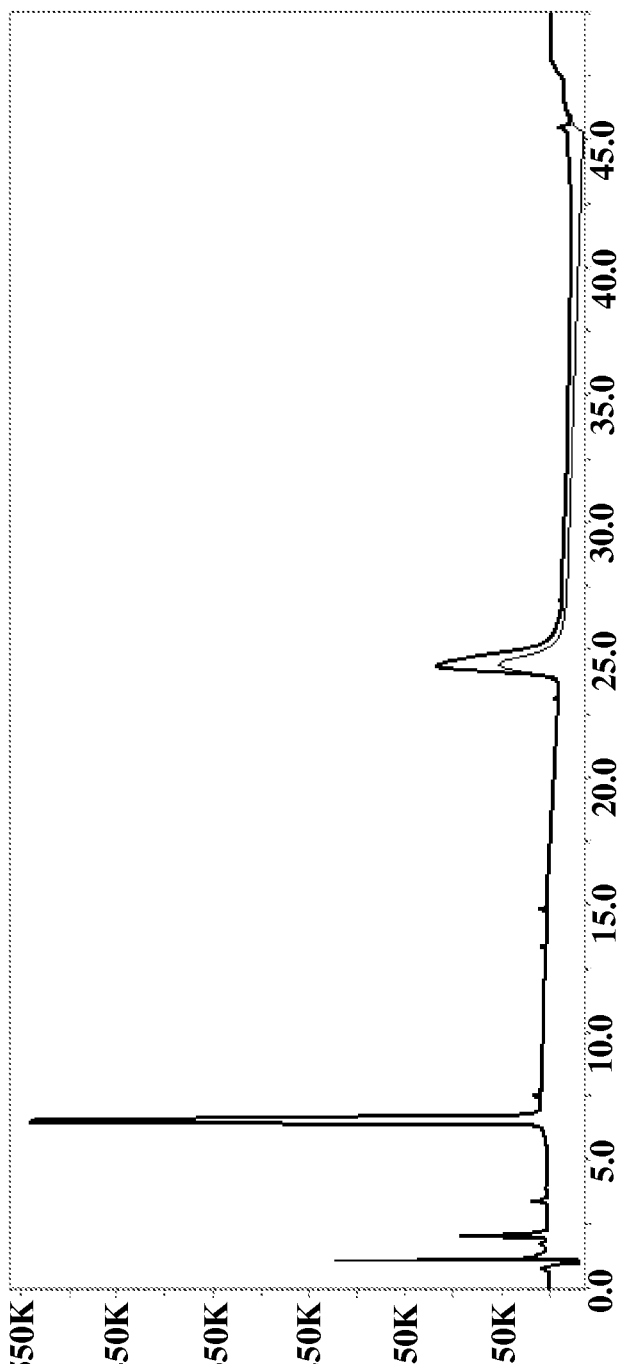
FIG. 6 is an HPLC chromatogram for Chol-GFP-siRNA extracted from crosslinked HSA NSs made with 0.03 mg DOTAP and 200 μg siRNA at pH 8 and untreated Chol-GFP-siRNA control, injected at the same gradient. The thick line is for absorbance at 260 nm and the thin line for absorbance at 280 nm. For siRNA (unlike proteins or peptides) the ratio $A_{260/280}$ is in the range of 1.8 to 2. The peak at app. 25.0 is attributed to the presence of Chol-GFP-siRNA extracted from crosslinked HSA NSs.

In order to determine the encapsulation efficacy of siRNA in the crosslinked HSA NSs, the washed NSs were digested with Trypsin till a clear solution was formed and the total siRNA content was detected using RP-HPLC and calculated based on AUC. According to the protocol we have developed in our lab (for detailing see section E), the reliability of such method in quantification the released siRNA, is highly efficient (FIGS. 5-6). The encapsulation efficacies for the HSA NSs produced in different pH conditions are summarized in Table 6. A few trends can be concluded; In the presence of DOTAP, the best encapsulation (~40%) accepted at the low basic pH (pH 8 and 7). At pH 9, removal of the DOTAP from NSs, have reduced encapsulation efficacies. This effect is more pronounced when the non cholesterol modified siRNA (GFP-siRNA) is used.

TABLE 6 encapsulation efficacies for the HSA NSs, 200 µg of siRNA -
Encapsulation efficacy summary for crosslinked HSA NSs made
with 200 µg siRNA (GFP or Chol-GFP) at different pH conditions
(pH of 7, 8 or 9) with or without addition of 0.03 mg DOTAP.
Experiment was made in duplicates and the average value is
displayed. Determination was made by RP-HPLC.

| pH | DOTAP | siRNA type | % encapsulation | Encapsulated is RNA (µg) |
|---|---|---|---|---|
| 9 | − | GFP | 9 | 18 |
| 9 | + | GFP | 24 | 48 |
| 8 | + | GFP | 42 | 84 |
| 7 | + | GFP | 43 | 86 |
| 9 | − | Chol-GFP | 16 | 32 |
| 9 | + | Chol-GFP | 26 | 52 |
| 8 | + | Chol-GFP | 40 | 80 |
| 7 | + | Chol-GFP | 39 | 76 |

Nanoencapsulation of Primary NSs into NCs by Nanospray Drying Approach

PLGA NS Loaded Nanocapsules Preparation Using Hydrophilic Coating Polymers

To produce stable, small, spherical NCs (empty or loaded with primary PLGA NSs), with intact envelop and in high yields, numerous formulations with different parameters were investigated:

(1) type of water soluble polymers including Dextran 40 (MW=40 kDa), Sodium Hyluronate (HA, MW=200 KDa) and Human serum Albumin (HSA, MW=66.5 kDa); (2) % (w/v) of hydrophilic polymer and PLGA NSs in water dispersed phase; (3) $T_{in}$ ($T_{in}$ is the inlet temperature, the temperature of the drying air/gas which flows linearly), and (4) addition of surfactant (Tween 80). In order to form the smallest submicron droplets, the smallest mesh size membrane (4 µm) was used.

The overall results of the extensive formulations studied led to the following observations:

(1) Spraying process with HA was insufficient due to its high viscosity (even at 0.1% (w/v) solution).

Figure 7A:
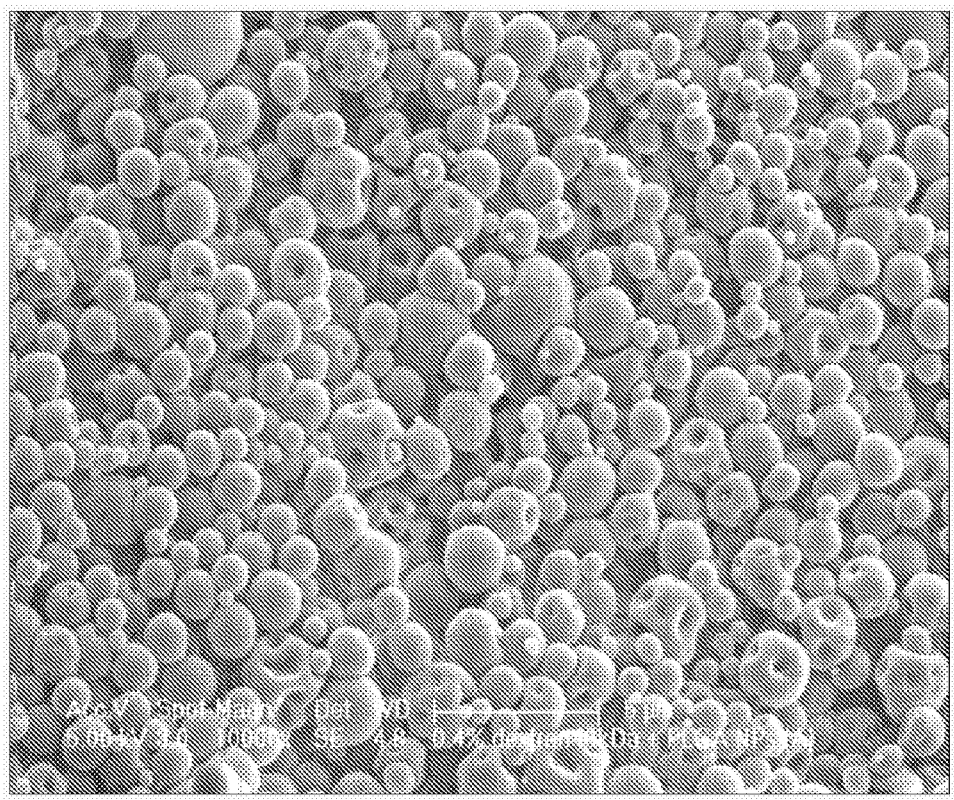
FIGS. 7A-7B are SEM micrographs of Dextran NCs encapsulating PLGA NSs. The NCs produced by the spray drying process of 0.4% (w/v) Dextran 40 in DDW (40 mg) consists of 30 mg of PLGA NSs (~100 nm, ZP of −33 mV).
Figure 7B:
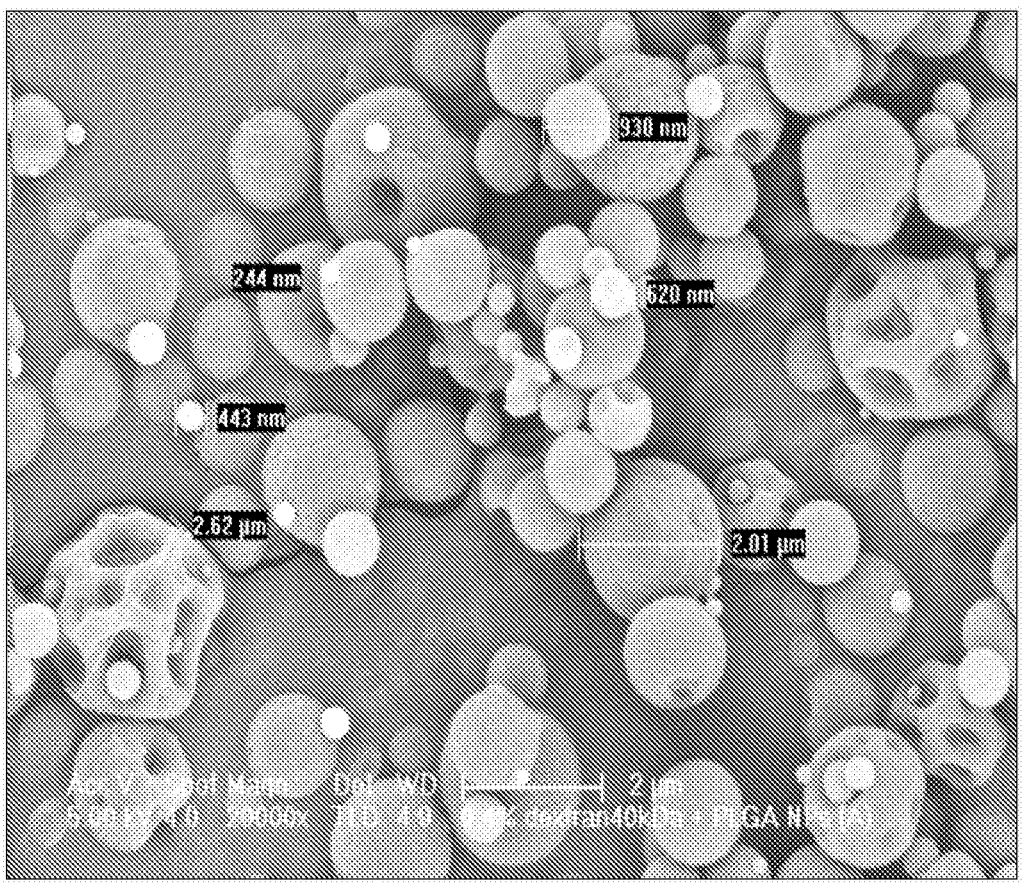
Figure 8A:
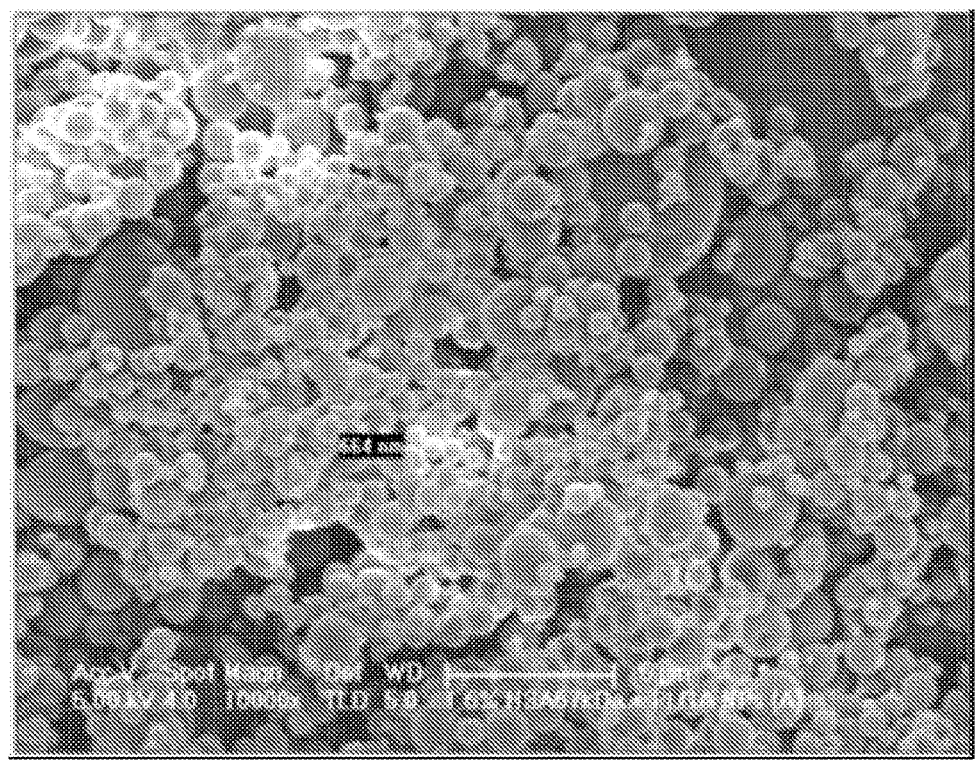
FIGS. 8A-8H are SEM micrographs of HSA NCs encapsulating primary PLGA NSs. The NCs produced by the spray drying process of HSA in different % (w/v) in DDW consist of PLGA NSs (~100 nm).
Figure 8B:
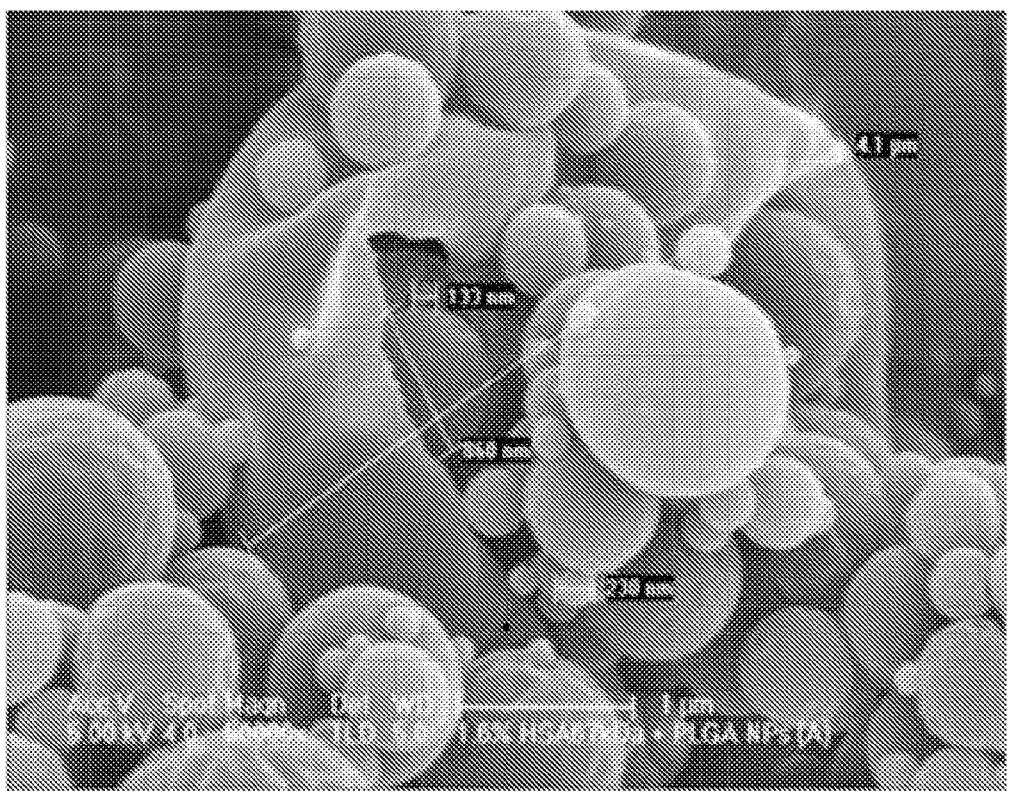
Figure 8C:
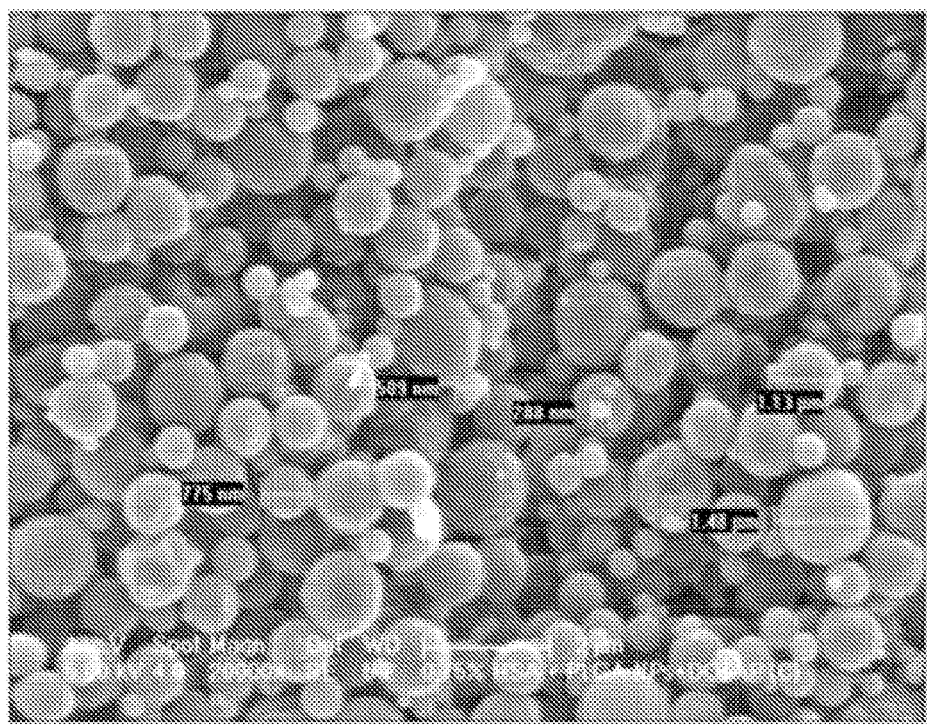
Figure 8D:
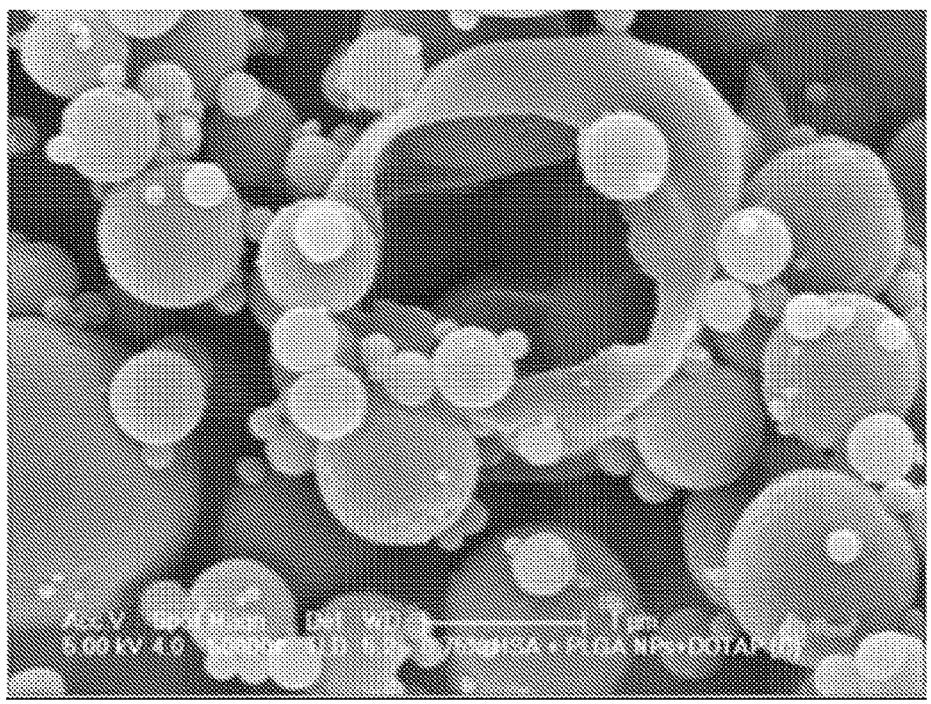
Figure 8E:
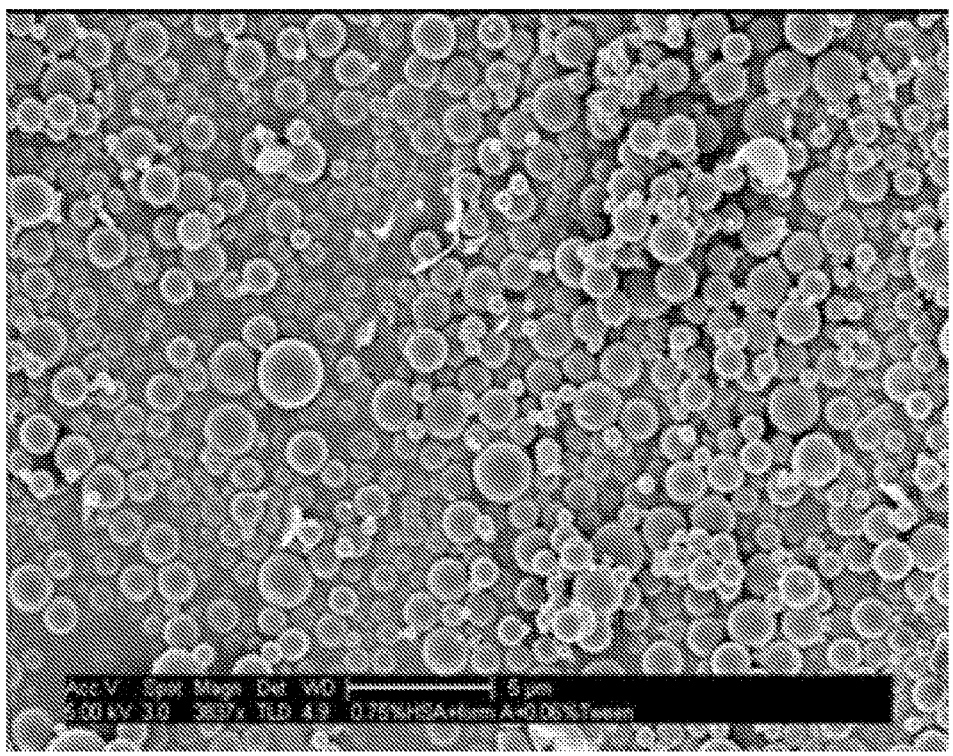
Figure 8F:
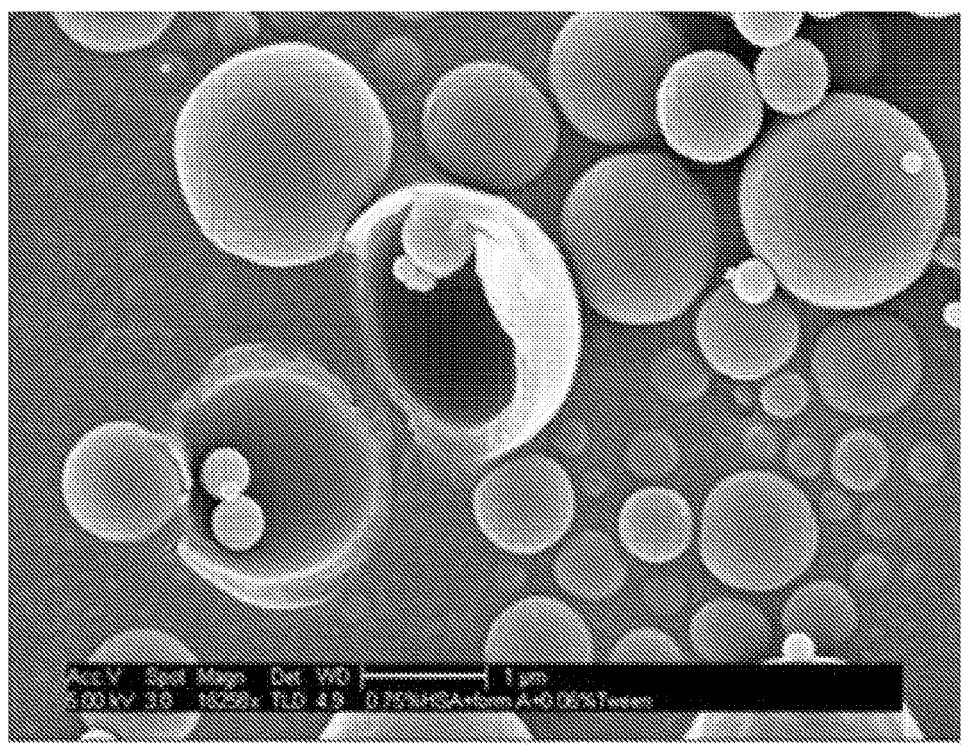
Figure 8G:
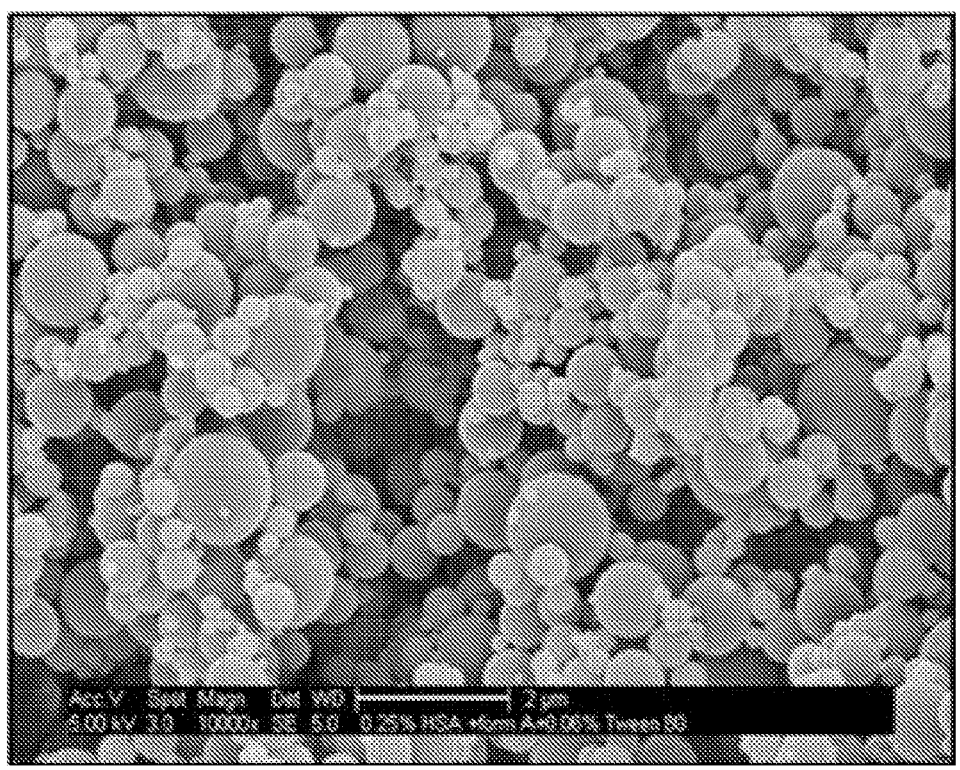
Figure 8H:
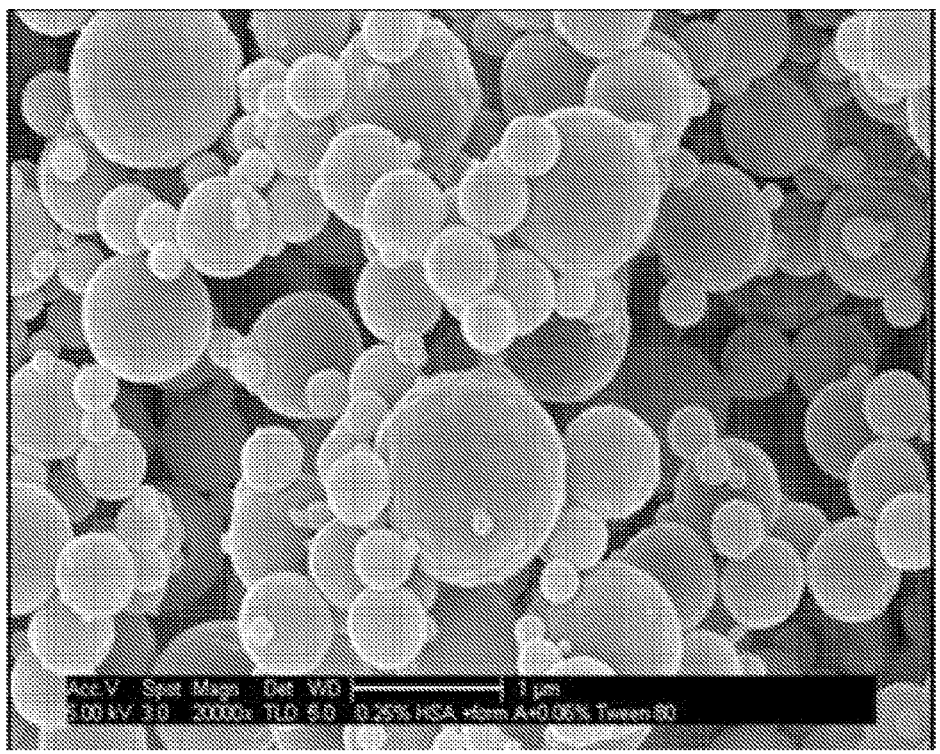

(2) PLGA NSs encapsulation using Dextran produced spherical NCs with perforated surfaces (FIG. 7).

(3) The best results were obtained when HSA was used at a range of concentrations of 0.1% to 1.6% (w/v) in aqueous phase.

(4) Empty HSA NCs were successfully prepared, as well as HSA NCs containing various amounts of PLGA NSs (positively and negatively charged).

(5) SEM measurements confirmed that: (a) In all cases, small, spherical NCs exhibiting intact surface were formed, and (b) When the concentration of HSA in DDW decreased, smallest NCs were formed (FIGS. 8A-8H). From FIGS. 8A-8H, it is deduced that the decrease in HSA concentration from 1.6% to 0.25% (w/v) resulted in the formation of NCs with decreasing size. Specifically, a small fraction of NCs decreased from 7 to 2 µm while most NCs population decreased from 2 to 0.5 µm, respectively.

Optimization of Nanoencapsulation Process

Optimization for the spray drying process was made only for the following parameters:

(1) Surface morphology—the best results obtained when HSA was used, as reported above.

(2) Particle size—upon reduction of solid concentration in the aqueous phase, the smallest NCs (0.3-2 µm) are formed, as reported above.

(3) Yields—addition of surfactant (Tween 80) at 0.06% (w/v) led to significant improvement of the yields achieved in the process, and in some cases improved the spraying rate (Table 7).

TABLE 7

Optimization for the nanospray drying process performed
at aqueous mode (*with negatively charged PLGA
NSs in a molar ratio of 4:1 HAS:PLGA)

| HSA in aqueous solution* [% w/v] | Yield [% w/v] | | Spraying rate [ml/min] | |
|---|---|---|---|---|
| | Without Tween 80 | with 0.06% Tween 80 | Without Tween 80 | with 0.06% Tween 80 |
| 0.1 | — | 96 | — | 0.05 |
| 0.25 | 11 | 77 | 0.02 | 0.03 |
| 0.5 | 30 | 98 | 0.02 | 0.16 |
| 0.75 | 21 | 90 | 0.03 | 0.05 |

Operating temperature—to produce dried NCs, different temperature of the drying air ($T_{in}$) were tested (80, 100 and 120° C.). Attempts to form dried NCs at 70° C. were not effective. We found that spray draying 80° C. was quite effective for our formulations, when siRNA was not included.

The temperature at which the 50% of siRNA strands are denatured is called the melting temperature, or Tm. The Tm for various siRNAs (21 mers) used in our research, was measured and found to be: 78, 77 and 72° C. for GFP-siRNA, Chol-GFP-siRNA and EGFR-siRNA, respectively. With all examined siRNAs, beginning of separation was already observed at 60° C. (data not shown).

Based on these results, we can conclude that exposing siRNAs to temperatures higher than 60° C. is not recommended, leading us to favor nanospray drying process performed at low temperatures (≤60° C.), usually efficient upon working with volatile organic solvents.

HSA NS Loaded Nanocapsules Preparation Using Hydrophobic Coating Polymers

To produce the desirable spherical submicron NCs (empty or loaded with primary HSA NSs), with a smooth interface and in high yields, together with spray drying at low temperatures (≤60° C.) different parameters were changed and tested: (1) type of organic disperse phase, (2) $T_{in}$, (3) type of hydrophobic polymers used for encapsulation—PLGA 48 kDa and PEG-PLGA 50 kDa [5 kDa for PEG+45 kDa for PLGA]), (4) % (w/v) of hydrophobic polymer and crosslinked HSA NSs in organic dispersed phase, (5) addition of surfactant (Tween 80 or PEG 4000) and (6) % spraying. Based on our previous experience acquired through operating the NSD B-90 in aqueous mode, only mesh size membrane (4 µm) was used in all experiments, and relatively small percentage of solids—0.07 to 0.26% (w/v) were dispersed in the organic phase, in order to produce NCs with size <1 µm.

(1) Several volatile organic solvents were tested as optional dispersed phases (ethanol, methanol, dichloromethane, diethyl ether, acetone and acetonitrile). The best results were obtained with acetone and acetonitrile (ACN) and therefore the majority of encapsulation experiments were made with these solvents.

(2) The spray drying were performed at temperatures of 60° C. or 50° C., when ACN was used, or at 40° C. or 30° C. when the more volatile acetone was utilized.

(3) In all the performed experiments, the yields were low (35% at most), probably due to the volatile nature of the solvents, leading to the appearance of "crustification" around the spraying head (appearance of solid aggregates or crystals). Such sedimentation blocks the vibrating membrane, and as a consequence, leads to a poor process with low yields and high polydispersity. This phenomenon was more pronounced when acetone was used instead of ACN.

(4) Addition of surfactant: Tween 80 (0.06% w/v), PEG 4000 (0.03% w/v), Pluronic F-68 (0.008% w/v), or lyoprotecting materials such as: trehalose (0.008% w/v), or sucrose (0.008% w/v), didn't help to prevent 'crustification' or diminishing the high polydispersity of the samples. Upon their addition, the yields were negligible, especially when Tween was used and the polydispersity of the formed NCs was high.

Figure 9A:
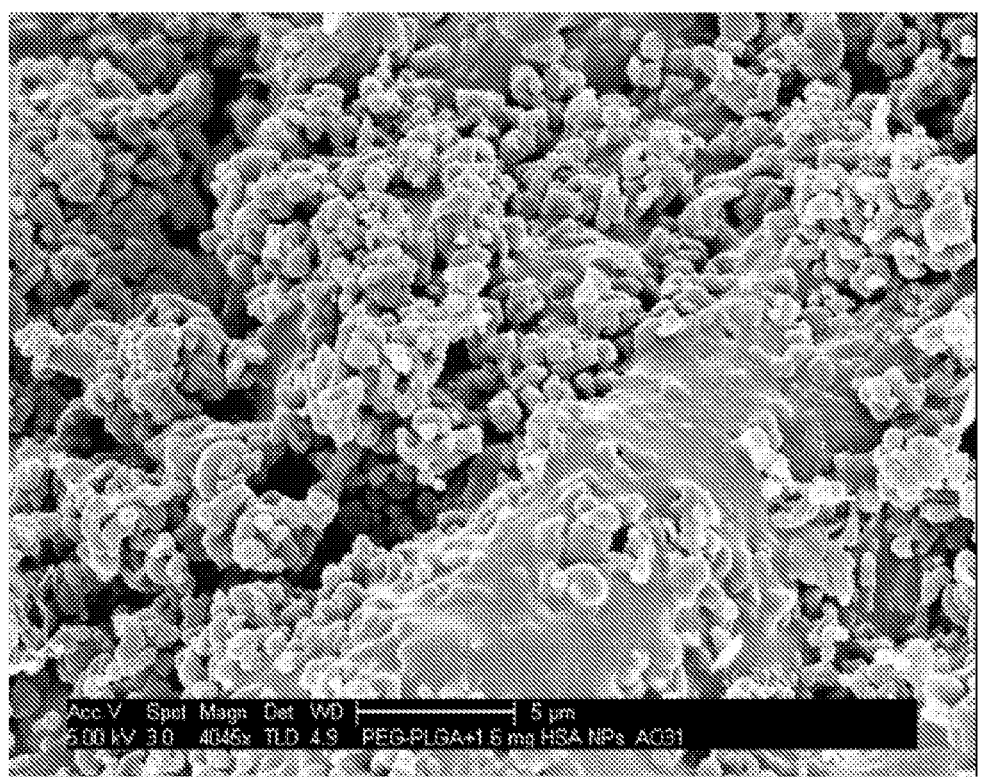
FIGS. 9A-9B are SEM micrographs of PEG-PLGA NCs encapsulating primary crosslinked HSA NSs. The NCs prepared by the spray drying process of PEG-PLGA (10.5 mg) in acetone consist of 1.6 mg HSA NSs (~100 nm, ZP −51 mV). During the spraying process appearance of crust on the spraying head was observed, leading to fusion of the NCs.
Figure 9B:
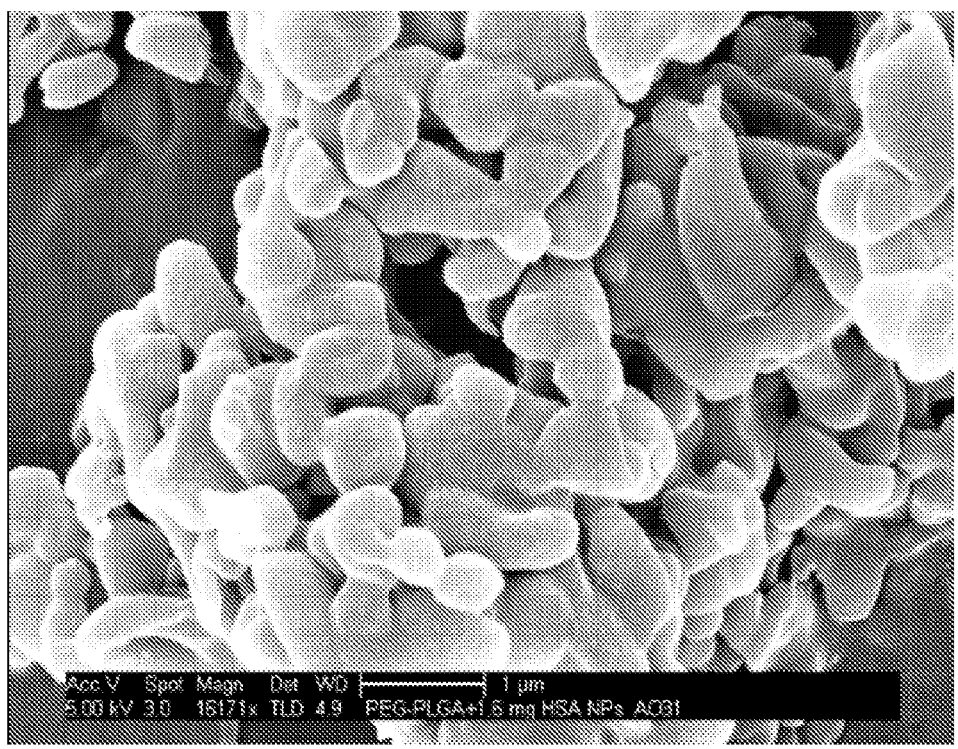

(5) When low parameter spraying is applied (60% instead of 100%), the temperature of the spraying head ($T_h$) is higher than $T_{in}$ by 12° C. and can lead to fusion of the formed NCs, as displayed in FIGS. 9A-9B. When 100% spray is applied $T_h$ is higher from $T_{in}$ only by 7-8° C.

Figure 10A:
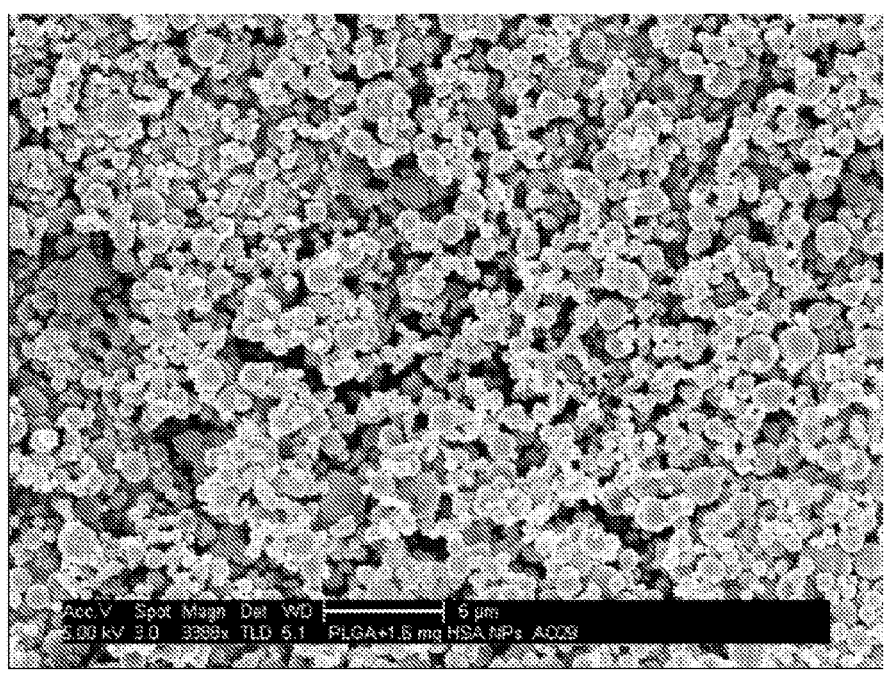
FIGS. 10A-10B are SEM micrographs of PLGA NCs encapsulating primary crosslinked HSA NSs. The NCs prepared by the spray drying process of PLGA (9.8 mg) in acetone consist of 1.6 mg HSA NSs (~100 nm, ZP −51 mV).
Figure 10B:
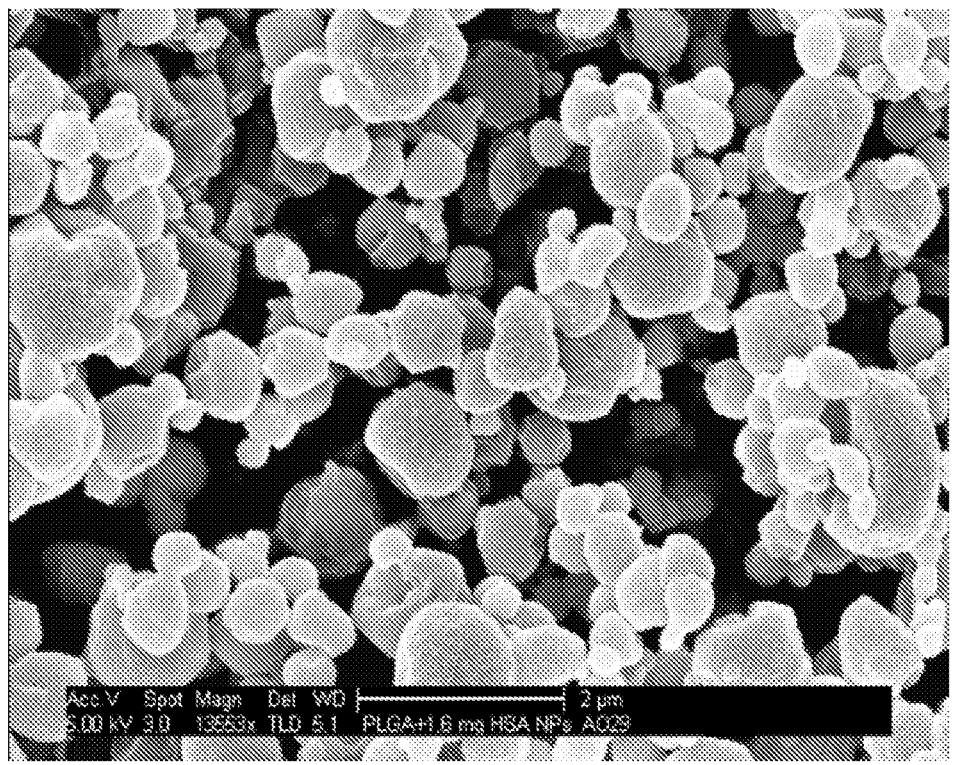

(6) Unlike PLGA, which produced spherical NCs in all tested samples (FIG. 10), PEG-PLGA was found to be more sensitive to head heating, hence in some cases, yielded amorphous NCs, as shown in FIGS. 9A-9B. DSC measurements support this assumption, with glass transition (Tg) values of 46.5° and 31° C., for PLGA and PEG-PLGA, respectively.

(7) Reducing solids content in the sample by 2 fold (from 0.21% to 0.13%), led to improvement in yields by 2 fold (from 16% to 35%).

(8) By sample dilution (20 ml of acetone instead of 10 ml), we have managed to increase the amount of dispersed HSA NSs by 6 fold (from 1.6 mg to 10 mg), without reducing yields (~20%).

Figure 11A:
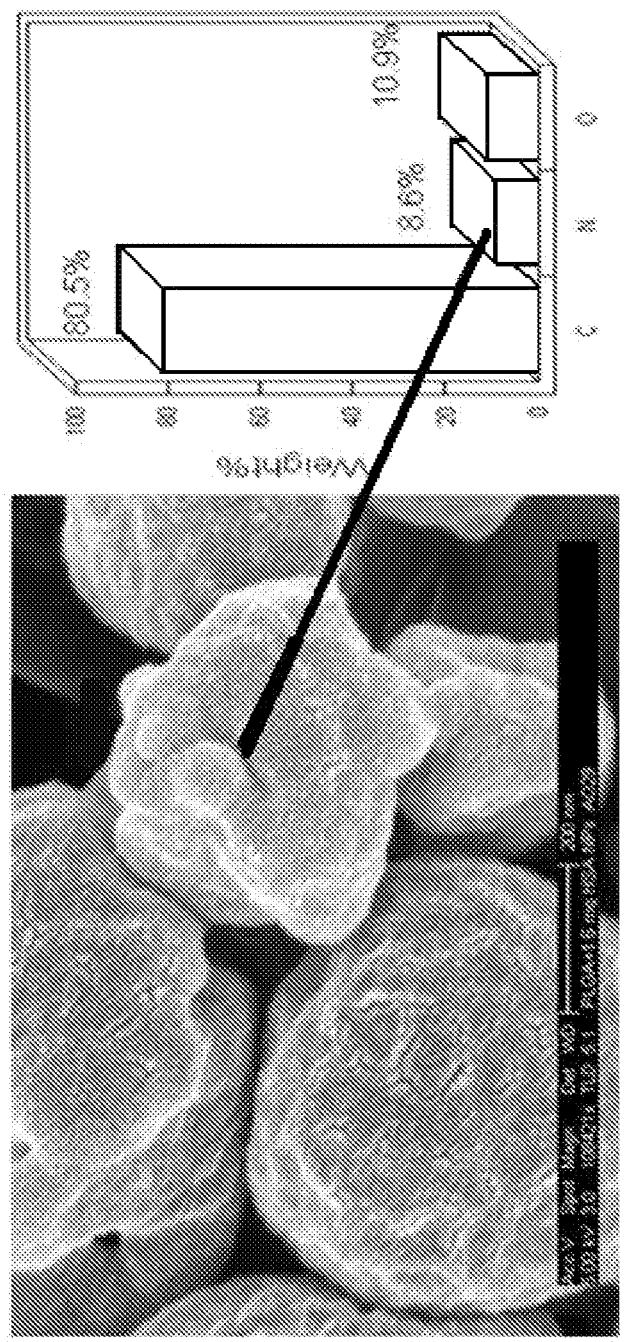
FIGS. 11A-11B are SEM micrographs of (A) PLGA NCs encapsulating 1.6 mg of primary crosslinked HSA NPs and of (B) PEG-PLGA NCs encapsulating 1.6 mg of primary HSA NSs and their element analysis using EDS (Energy Dispersive X-ray Spectroscopy). The nitrogen can originate only from the HSA NSs.
Figure 11B:
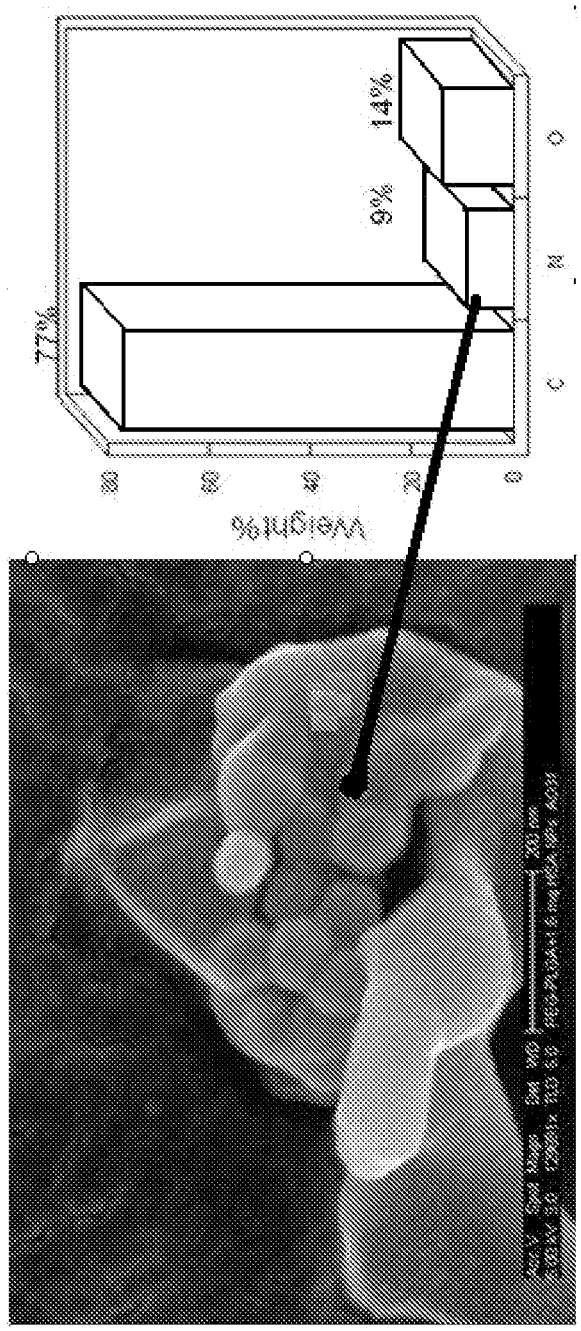

Encapsulation of primary HSA NSs inside the organic polymers (PEG-PLGA & PLGA) was validated using EDS (Energy Dispersive X-ray Spectroscopy), as demonstrated in FIG. 11.

Figure 12A:
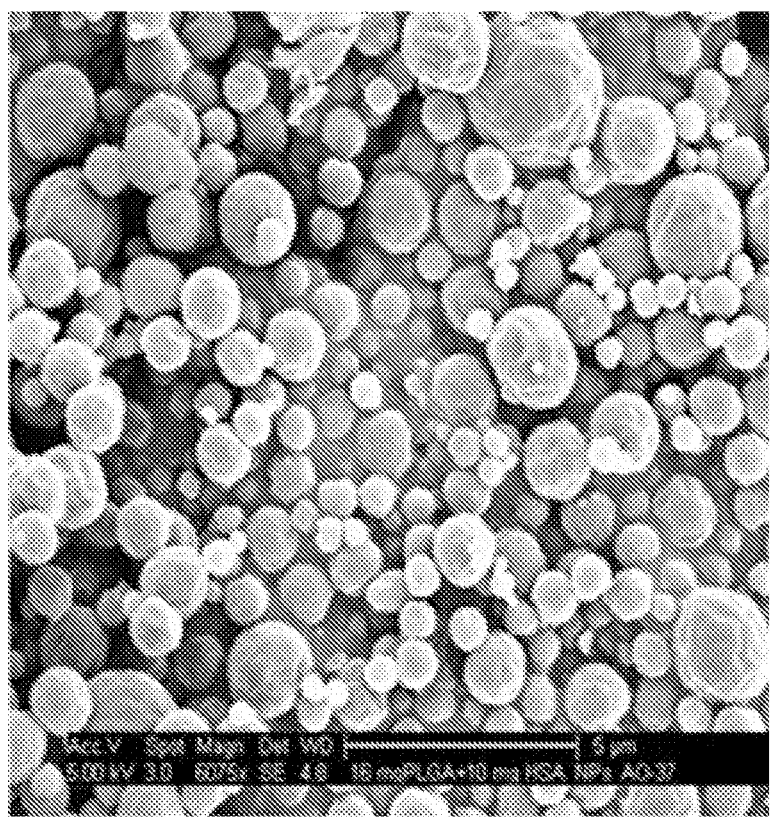
FIG. 12A: PLGA NCs.
Figure 12B:
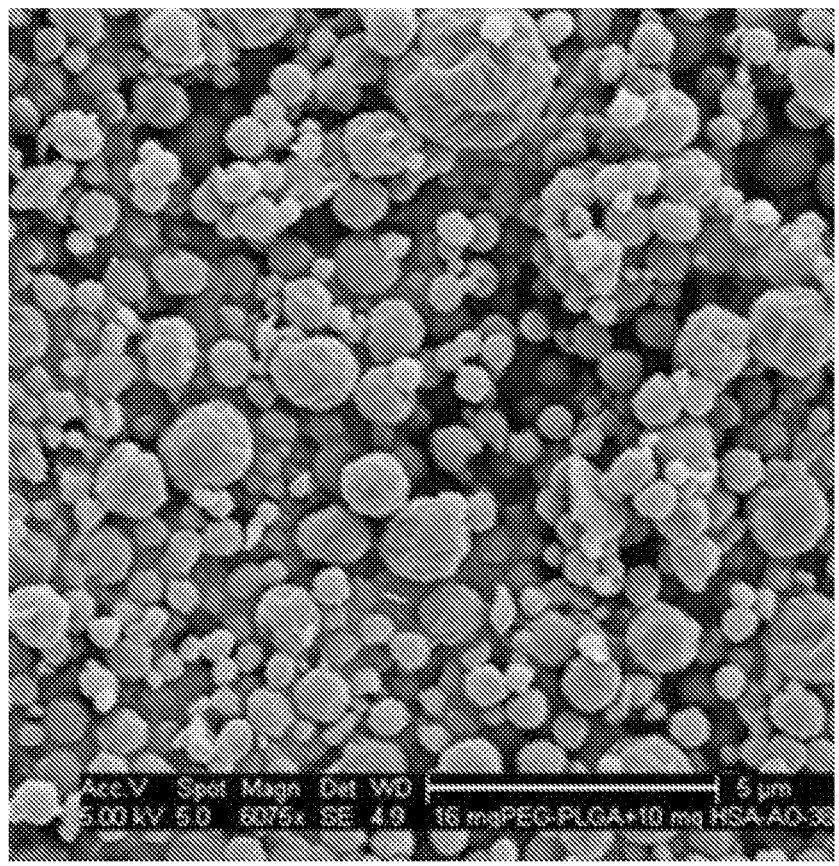
FIG. 12B: PEG-PLGA NCs. The NCs made by spray drying process of polymer (16 mg) in acetonitrile consist of 10 mg crosslinked HSA NSs (~100 nm, ZP −43 mV).

Increased amount of dispersed crosslinked HSA NSs together with the prevention of massive crust formation around the spraying head, were achieved by using mainly ACN as the disperse organic phase. Furthermore, when ACN was used and the $T_{in}$ was reduced from 60° C. to 50° C., no crustification occurred, and the membrane was clear throughout the entire spraying process resulting in the formation of spherical sub-micron NCs when PLGA or PEG-PLGA were applied (FIG. 12). However, still relatively low yields (~30%) are obtained. This parameter will be further examined and optimized.

Size Distribution of the Loaded NCs

Two samples with 0.1% solids content were made in ACN (samples AO-66 and AO-68), forming PLGA NCs loaded with HSA NPs encapsulating siRNA. We can clearly see favored formation of the desired submicron NCs. Another sample with 1% solids (sample AO-57) of empty 50 kDa PLGA NCs was prepared for comparison.

All PLGA NCs (empty or loaded with primary HSA NPs), were made by Nano spray dryer B-90, operates at organic phase (Acetonitrile, $T_{in}$ 50° C.). The dried NCs are stored at dark room at 4° C., in sealed vials, prior to characterization.

In order to characterized the dried NCs using Mastersizer 2000E, each sample was dispersed in water (DDW, 2 mg/ml) using vortex, then left to stirred (with stirrer) over night in an ice bath till a turbid homogeneous dispersion is formed.

All measurements at Mastersizer 2000E were made in a stainless steel sample dispersion unit (120 ml volume), with an active stirring (no need in sonication or addition of surfactant). The results (calculated by Volume or Number), were compared to images accepted by SEM measurements previously made for the dried sample.

Figure 13A:
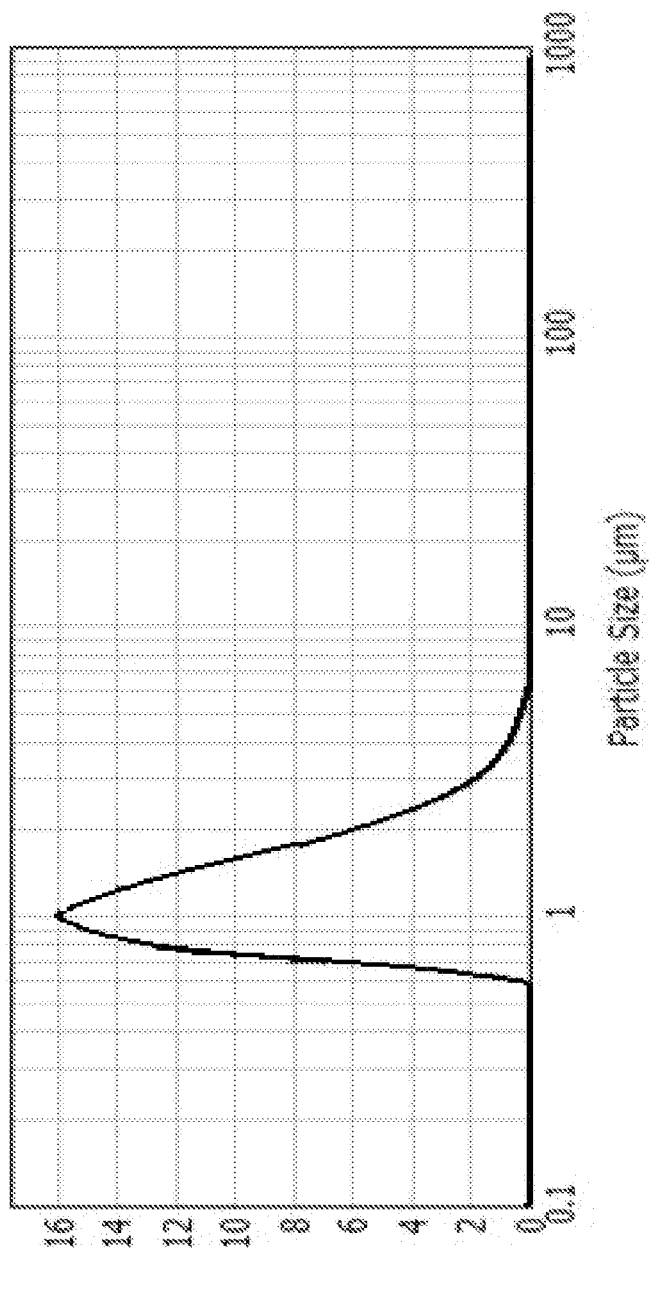
FIGS. 13A-13B are size distribution and SEM micrographs of sample AO-57: PLGA (50 kDa) NCs encapsulating of primary crosslinked HSA NSs.
Figure 13B:
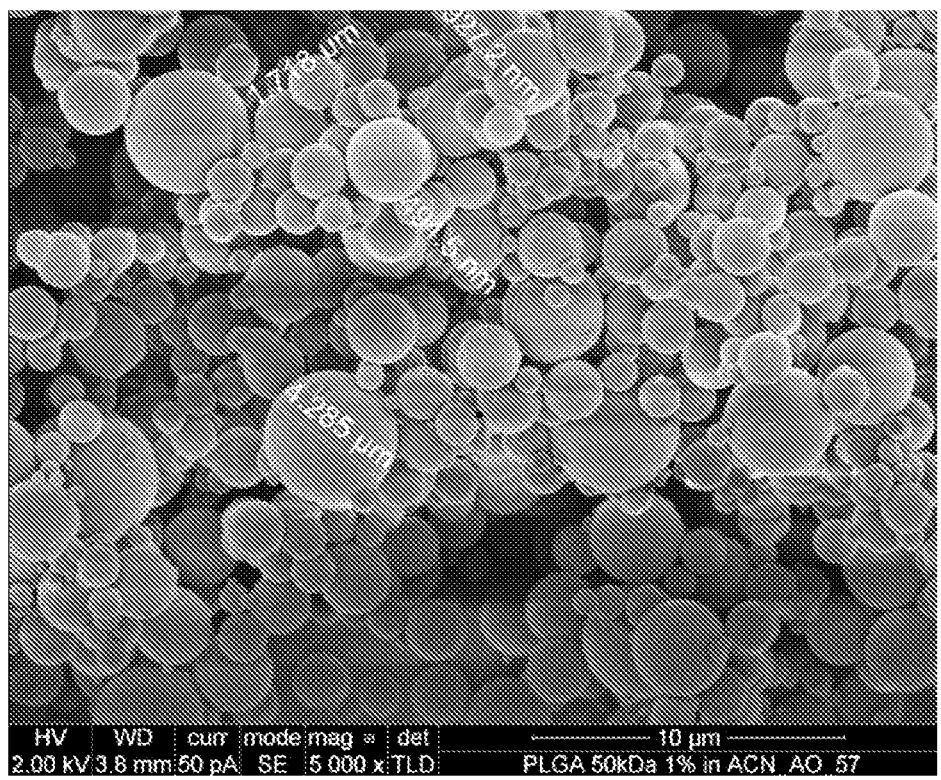
Figure 13C:
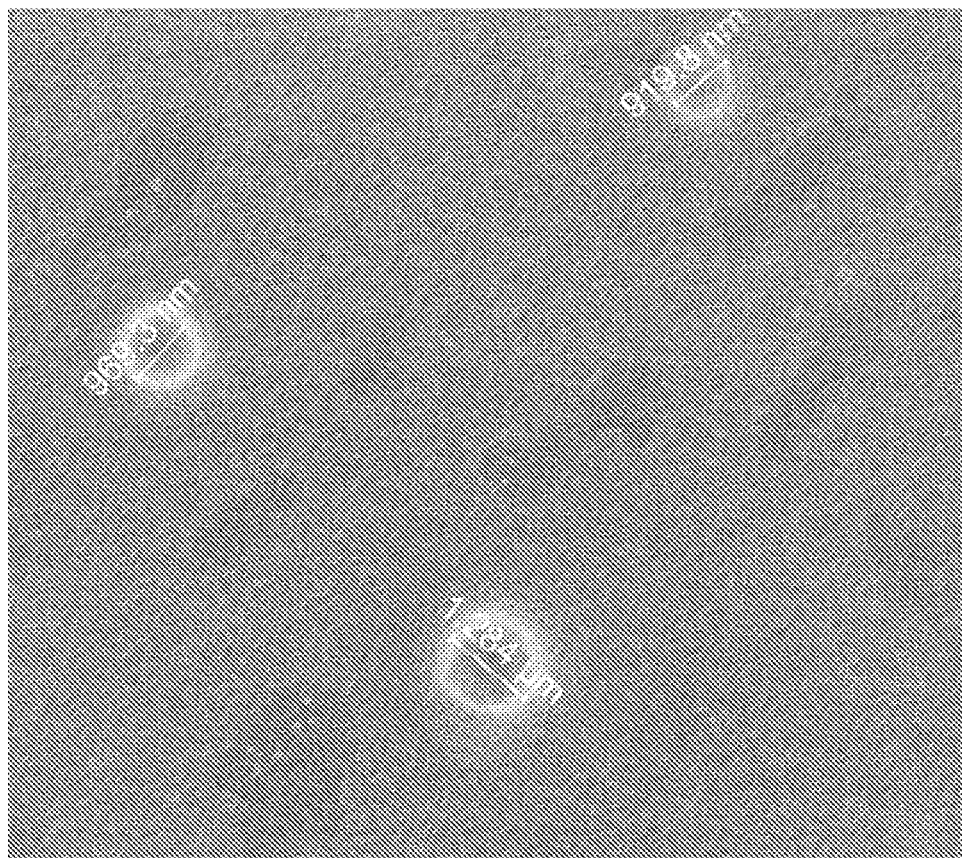
FIG. 13C are NCs dispersed in water after 4 days
Figure 14A:
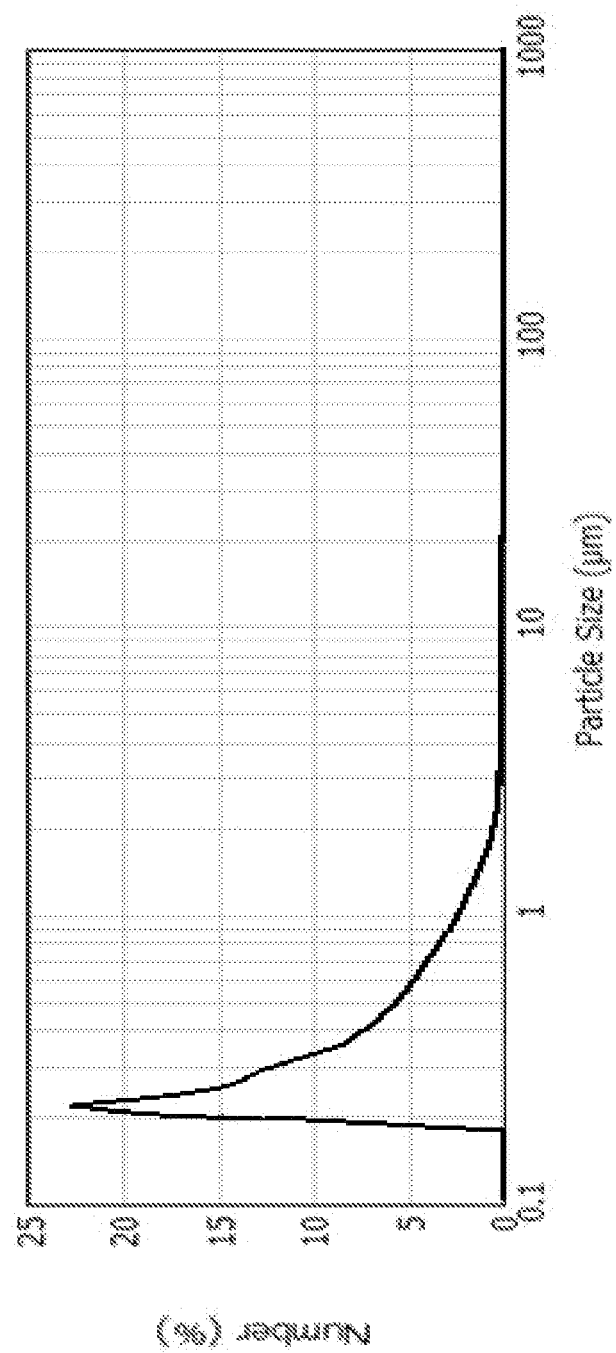
FIGS. 14A-14B are size distribution and SEM micrographs of sample AO-66: PLGA (50 kDa) NCs encapsulating of primary crosslinked HSA NSs loaded with GFP-siRNA. The NCs made by spray drying process of polymer (42 mg) in 40 ml acetonitrile consist of 12.6 mg crosslinked HSA NSs (~100 nm, ZP −43 mV).
Figure 14B:
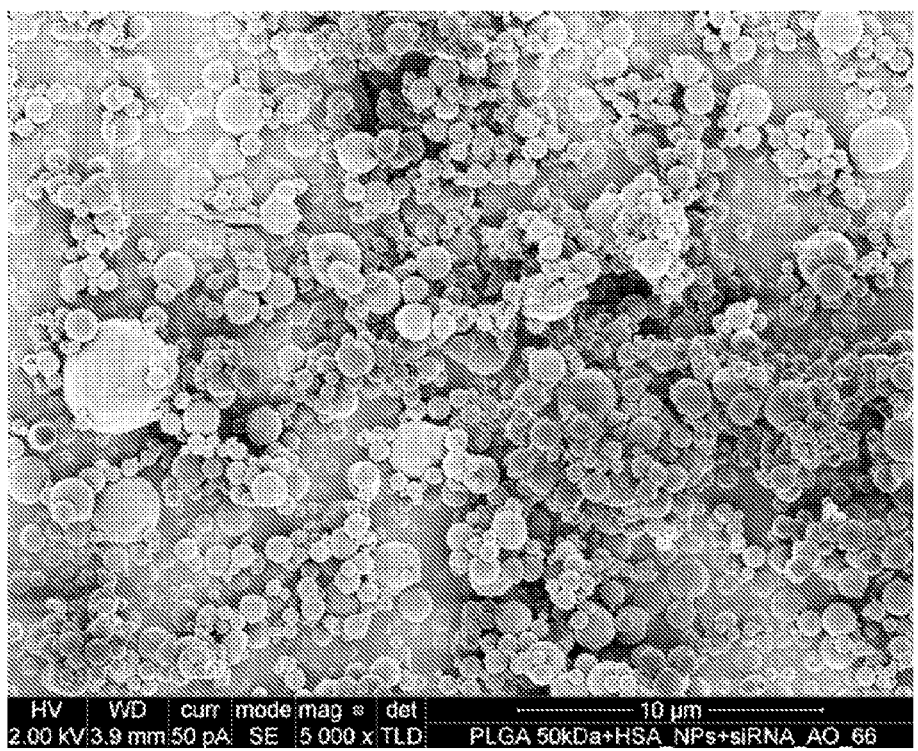
Figure 15A:
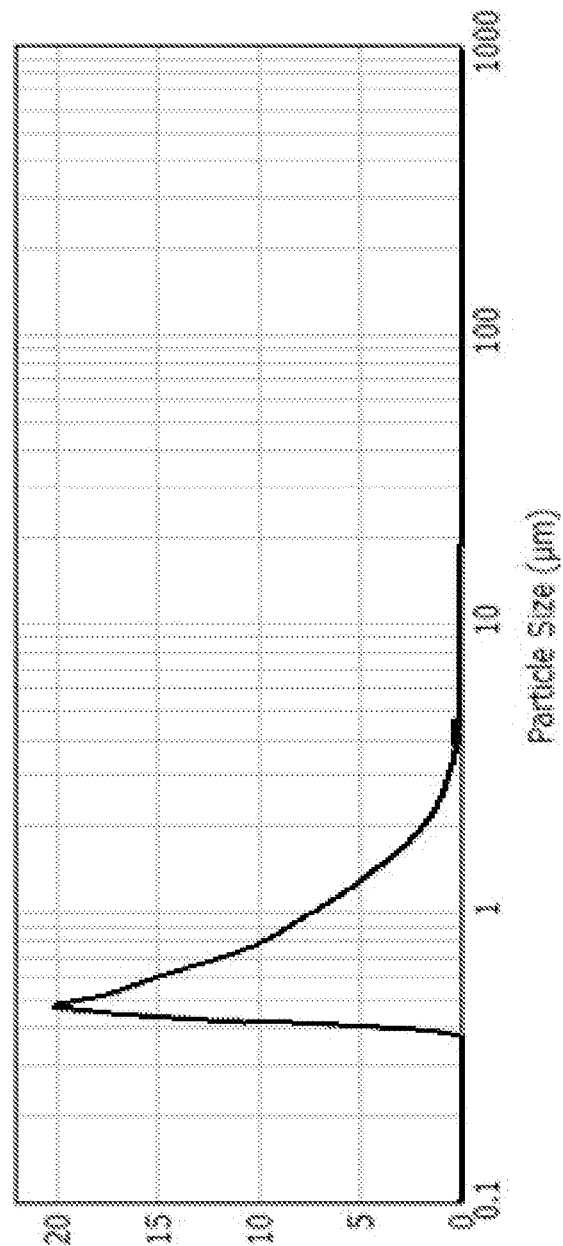
FIGS. 15A-15B are size distribution and SEM micrographs of sample AO-68: PLGA (50 kDa) NCs encapsulating of primary crosslinked HSA NSs loaded with Chol-GFP-siRNA. The NCs made by spray drying process of polymer (64 mg) in 60 ml acetonitrile consist of 15 mg crosslinked HSA NSs (~100 nm, ZP −43 mV).
Figure 15B:
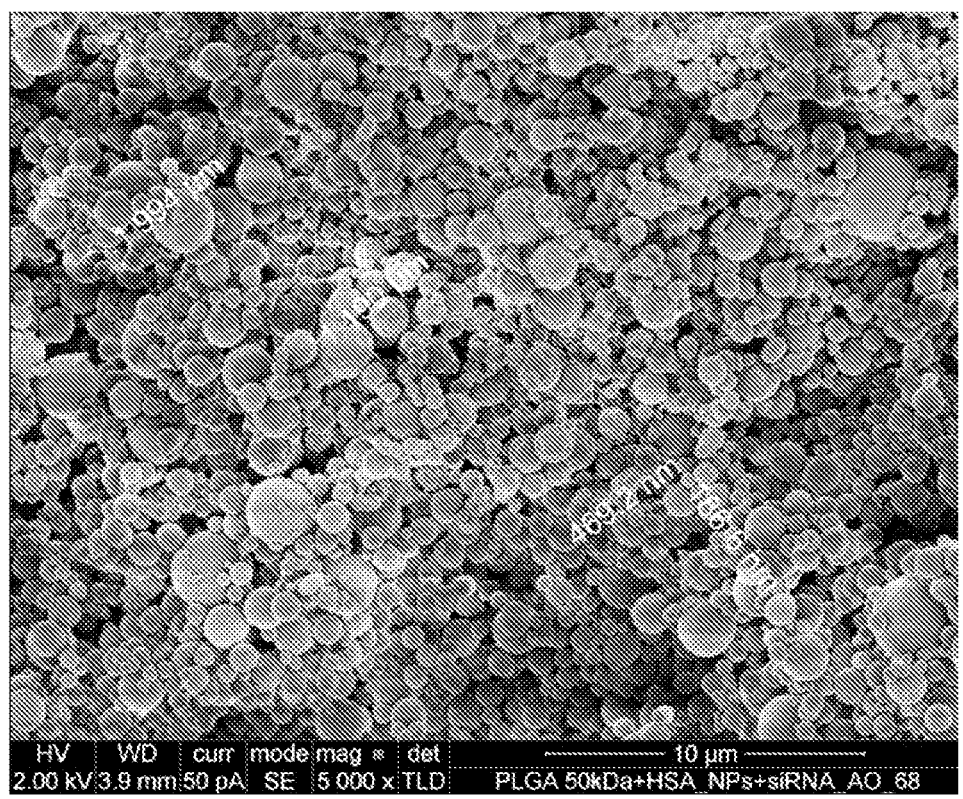

Based on size measurements by volume, made with laser diffraction technique using Mastersizer 2000E (Malvern), it was found that for sample AO-68, 80% of the NCs population is under 1 μm (with 56% under 0.724 μm) and Span value of 1.472. For sample AO-66 better results obtained; 94% of the NCs population is under 1 μm (with 86% under 0.724 μm) and Span value of 2.077. Low span value means low polydispersity (FIGS. 13-15). For comparison purpose, a sample with 1% solids (PLGA) content was measured too (sample AO-57), revealing formation of bigger NCs; 94% of the NCs population is under 2.5 μm (with 42% under 1 μm and only 4% under 0.724 μm). These results are encouraging and show promise potential for the nanoencapsulation technique made with highly diluted formulations contain ~0.1% solids content.

Integrity Evaluation of Encapsulated siRNA

Figure 16A:
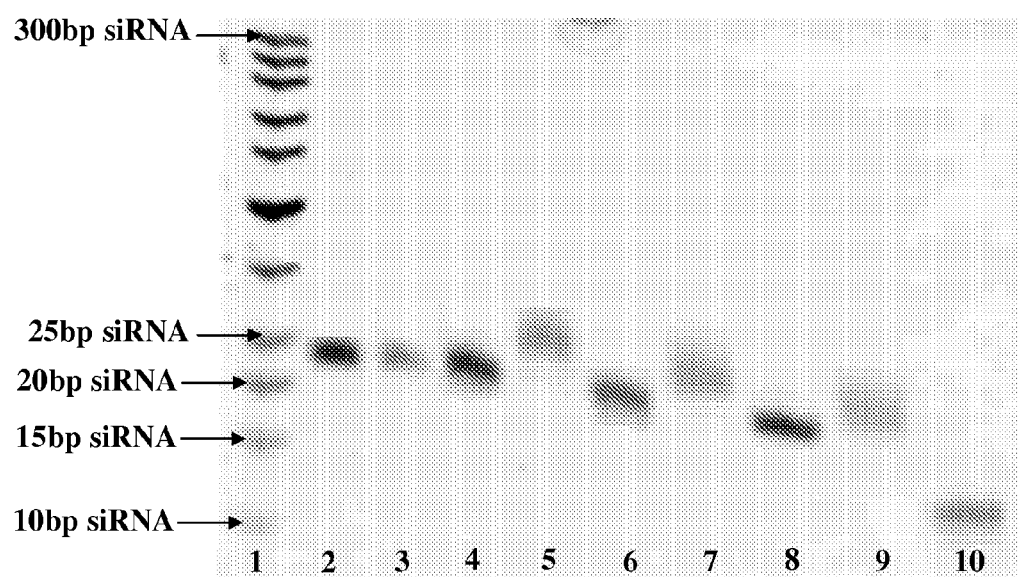
FIGS. 16A-16B are gel retardation assays (PAGE 8%) for evaluation of free siRNA integrity after exposure to different conditions. Integrity evaluation was made for GFP-siRNA (FIG. 16A) and Chol-GFP-siRNA (FIG. 16B). Lane No. 1—ladder, Lane No. 2, 3—controls with 100 and 50 ng of untreated siRNA respectively. Lanes 4, 6 and 8, with siRNA exposed to pH 7, 8 and 9, respectively. Lanes 5, 7 and 9, with siRNA exposed to pH 7, 8 and 9 in the presence of glutaraldehyde (0.014% (v/v)), respectively.
Figure 16B:
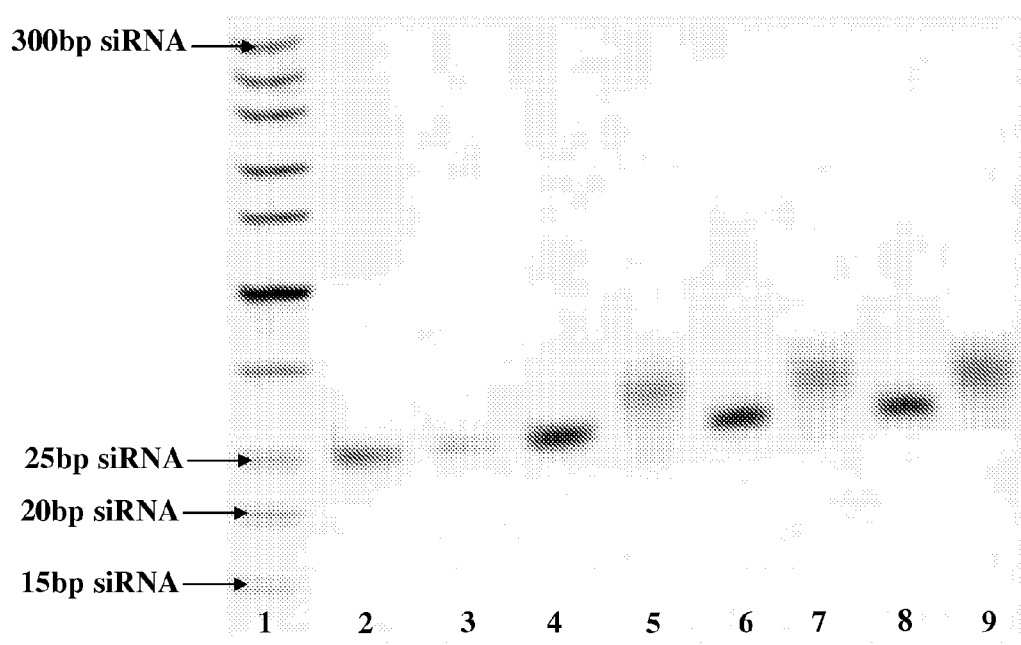

During the primal encapsulation process of siRNA in the HSA NSs it has been exposed to materials with distractive potential such as basic pH conditions and the presence of cross linker (glutaraldehyde) who can interact with the primal amine present in the nucleic bases: Guanine, Adenine or Cytosine. Hens, the need in siRNA integrity evaluation arise. First, integrity evaluation of the free siRNA (GFP-siRNA and Chol-GFP-siRNA) was made. The siRNAs were exposed to the same conditions used for production of crosslinked HSA NSs (3 hr at aqueous solutions with pH of 7, 8 or 9 with or without the presence of glutaraldehyde), then a fraction from each sample was analyzed using HPLC (data not shown) and gel retardation assay (PAGE 8%) (FIG. 16). The results, shows increase sensitivity of siRNAs as the pH becomes more basic, while Chol-GFP-siRNA revealed improved resistant to basic pH (8 and 9) compared to GFP-siRNA. On the other hand, the two types of siRNA found to be highly sensitive to the presence of the cross linker, in all the pH tested, leading to a formation of 'heavy' specie runs slower at the gel—implying a possible distractive crosslinking process occurred to the siRNA.

Figure 17A:
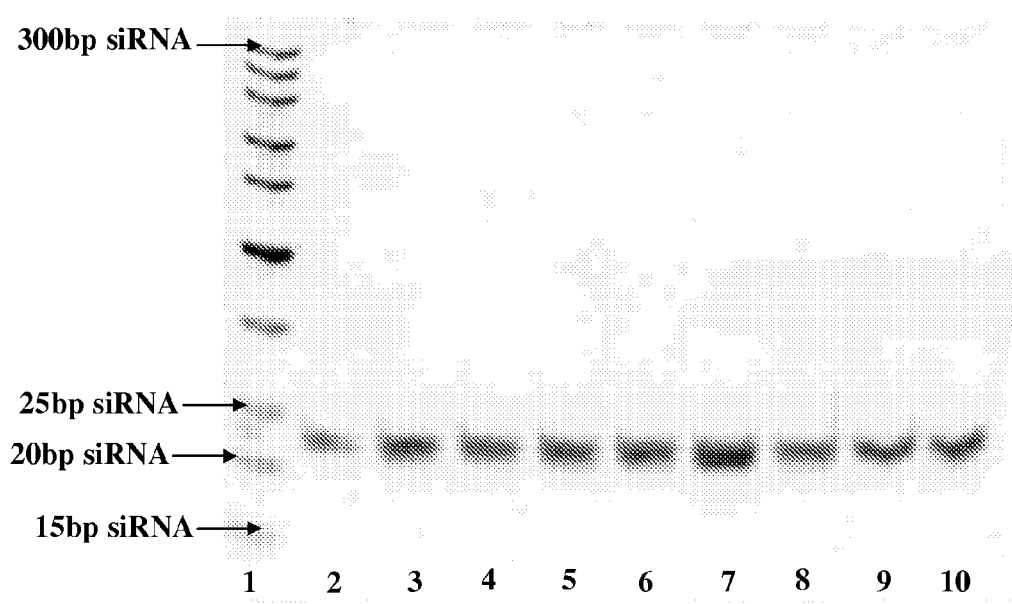
FIGS. 17A-17B are gel retardation assays (PAGE 8%) for evaluation of extracted siRNA. Integrity evaluation was made for GFP-siRNA (FIG. 17A) and Chol-GFP-siRNA (FIG. 17B). Lane No. 1—ladder, Lane No. 2—control with 100 ng of untreated siRNA. Lanes 3-8 with siRNA extracted from primal crosslinked HSA NSs (produced in different pH conditions), Lanes 9 and 10, with siRNA extracted from NCs loaded with the primal crosslinked HSA.
Figure 17B:
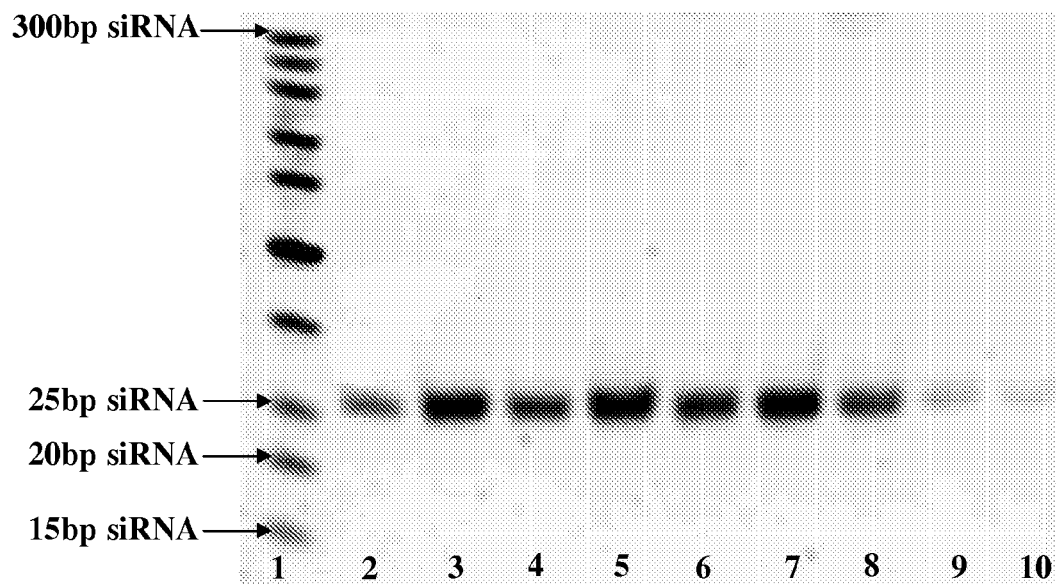
Figure 18A:
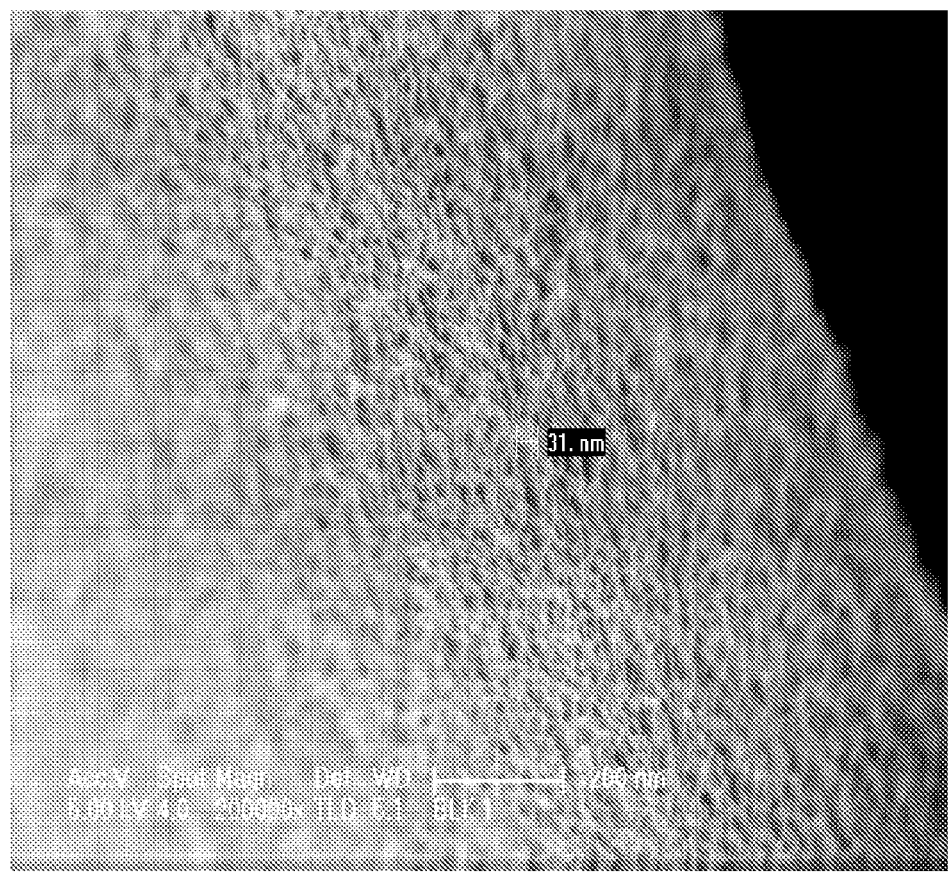
FIG. 18A is a SEM imaging of BSA NSs following preparation and washings using the Vivaspin technique. The NSs were dried at room temperature on a slide following spreading of one droplet of the dispersion.
Figure 18B:
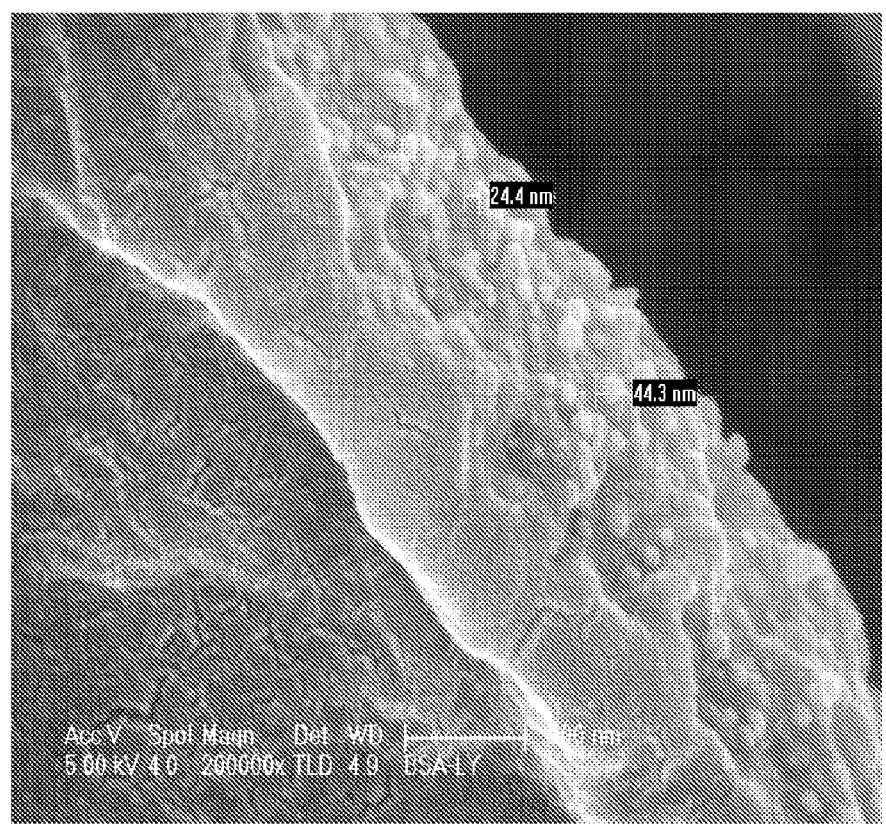
FIG. 18B is a SEM imaging of BSA NSs following preparation and washings using the Vivaspin technique. The NSs were dried at room temperature on a slide following spreading of one droplet of the dispersion.

Later, siRNAs were extracted from the primal crosslinked HSA NSs (produced in different pH conditions), and their integrity was assessed using HPLC (data not shown) and gel retardation assay (PAGE 8%) (FIG. 17). Furthermore, the stability of siRNAs extracted from NCs loaded with the primal crosslinked HSA was also examined (FIG. 15—lanes No. 9 & 10), since secondary encapsulation process performed under heat ($T_{in}$ is 50° C.), using the nano spray drying technique. Based on the PAGE results represent at FIG. 17, we can clearly see that the siRNAs (Chol-GFP- or GFP) encapsulated in the primal or secondary NCs, stayed intact and runs like the untreated siRNA (lane No. 2), and no fragmentation appeared. Based on the HPLC results, the exact amount of encapsulated siRNA was determined. In the future, the activity of the extracted siRNAs will need to be verified 'in-vitro'.

Protocol 1—Conjugation of Ranibizumab (Lucentis) or Bevacizumab (Avastin) to Nanospheres' Surface MAb Wash and Quantity Determination The Ranibizumab and bevacizumab were washed using 8.5 cm dialysis bag (Medicell international, 12-14K) in order to remove amino acids such as hystidine or glycine that can interact with the LC-SMCC spacer and interfere with the MAb activation. The dialysis bag was washed in 2 liters DDW prior to the addition of Ranibizumab. Then about 500 μl of Ab were washed in a total volume of 3 liters PBS conc. ×10, without magnesium and calcium diluted in DDW at a pH of 7.4. Following overnight wash, the Ab total volume was adjusted to achieve a concentration of 2 mg/ml Ab in PBS and the Ab was centrifuged in 4° C. at 14,000 rpm for 15 minutes to remove residuals of glycerol from the dialysis bag. The Ranibizumab concentration was then determined using a spectrophotometer at wave length of 280 nm.

MAb Activation with the Spacer LC-SMCC

The amine group ($NH_2$) on the MAb and the ester group (—R—COO) on the LC-SMCC were reacted to create an amide bond, the reaction took place under rotation at 180 rpm in 4° C. for 2 hours. The molar ratio of MAb to LC-SMCC was 1:100, more specifically; 50 µl of the spacer solution in DMSO (1 mg/100 µl) were added to 2 mg MAb (1 ml). Final DMSO concentration did not exceed 5%. When-needed, for Non-Activated MAb validation, 0.5 mg of residues MAb were added to about 12.5 µl of DMSO to keep the same ratio of DMSO to MAb and was incubated under the same conditions. Following the activation Ranibizumab was centrifuged in eppendorfs at 14000 rpm, 4° C., for 10 minutes and the supernatant was withdrawn and washed to eliminate any residues of LC-SMCC that did not react with the MAb and to achieve a final concentration of 1 mg/ml Ab. 2 mg (1 ml) were washed with a total volume of 15 ml in PBS×2.5 (pH=7) using a vivaspin with 30000 MWCO under 4000 rpm, 10-15 minutes at 4° C. The process was performed for the Non-Activated MAb as well.

NSs Preparation Process

Two formulations were manufactured according to the same protocol. For the preparation of NPs, 75 mg Resomer 504H, 75 mg PLGA 50-50 45000 PEG 5000 (50,000 KD), 10 mg OCA linker were dissolved in 25 ml acetone. The organic phase was injected to 50 ml of the aqueous phase, which contained 50 mg Solutol® RH under stirring at a rate of 900 rpm. The stirring continued under the same conditions for 15 minutes following injection and then the formulation was evaporated at 37° C., at a stirring rate of 30 rpm for about 1 hour. When evaporation finished the pH was corrected to 6.8-7 using NaOH 0.1 N and the final volume was completed to 5 ml with water for HPLC. Finally, the formulation was centrifuged for 10 minutes at 4000 rpm, room temperature to remove polymer sediment.

NSs Incubation with Ranibizumab and Bevacizumab—Preparation of the nanoMAb

The thiol-group on the OCA linker and the spacer melaimide were reacted overnight at room temperature. 2 ml formulation with 2 mg MAb (at a solution concentration of 1 mg MAb/ml) were reacted in a scintillation bottle under mild stirring (500 rpm). Non-Activated MAb was also incubated with the NSs overnight under the same conditions.

NanoMAbs Washing

At the next morning the samples were washed with water for HPLC over a 300,000 MWCO vivaspin at 4000 rpm, 4° C. to eliminate residues of Mab that did not react with the NSs. The wash volume was ×10 from the formulation volume. The Non-Activated NanoMAbs and NSs were washed at the same conditions. The residuals were collected in a 15 ml polypropylene tubes and kept under −80° C. until freeze-drying, while the formulations were concentrated to achieve the original volume of the formulations before the wash.

NSs and NanoMAbs Characterization

100 µl from each formulation was diluted in 1000 µl of water for HPLC, filtered via 0.2 µm PVDF filter and analyzed using the Malvern Zetasizer (Malvern Instruments, Malvern UK) to determine the zeta potential and particles diameter size.

Protocol 2—Nanoencapsulated Ranibizumab and Bevacizumab with Crosslinked Bovine Serum Albumin (BSA)

Primary Crosslinked BSA NSs Preparation

In order to produce nanometric BSA NSs, the well known method of pH-coacervation (also known as desolvation technique was applied). Briefly, BSA solution, adjusted to a specific pH, was transformed into nanoparticles by continuous (~1 ml/min) addition of desolvating agent, under constant, rapid stirring (~960 RPM or 40 HZ) at room temp. Addition of desolvating agent is continued until sufficient turbidity appears (usually between 40 to 80% (v/v) of desolvating agent), then the crosslinking process is carried out with glutaraldehyde for at least 2 hr at room temperature under milled shaking. After crosslinking, desolvating agent was evaporated (37° C.) and centrifuged for 10 min at 4,000 RPM (precipitation was removed, dried and determined gravimetrically). NSs were washed (×10) with DDW, at three different cycles of centrifugation (4,000 RPM, 4° C.), using vivaspin 300 kDa (Viva science).

Avastin Double Nano-Encapsulation of Non-Cross Linked BSA NSs Using Nanospray

Bevacizumab was transferred to polysorbate 20 solution by dialysis. (cut off 14 KDa, three time 2 hrs in 500 ml Tween-20 (0.4 mg/ml), room temperature). The Ab was then nano-encapsulated with BSA as described in previous report. After injection of the acetone to the aqueous solution containing the peptide and the albumin to elicit formation of BSA NSs during strong vortex, an aliquot of 0.75 ml of the suspension was withdrawn and incorporated immediately to 24 ml of acetonitrile containing 16 mg PLGA (50K) with stirring. This suspension was then evaporated using the nanospray dryer. Final solution: DDW 1.01%, acetone 2.02%, acetonitrile 96.97%. Solids composition: Ab 1.9%, albumin 37.7%, PLGA 60.4%. Final solids concentration over all solution was 0.104%; Nanospray conditions: 4 µm mesh, at 50° C.

Encapsulation of BSA NSs Using Nanospray Dryer—Organic Mode

NCs were prepared via spray drying on the NSD B-90 operates at 'closed loop' mode, hence, $N_2$ (g) and $CO_2$ (g) are flowed in the system instead of air. In all experiments gas flow was about 120 l/min. The air soaked with volatile vapors and humidity, transferred to a Dehumidifier unit, for drying and condensation, then returned dry to the system in a circular path. Spray drying was carried out at low temperatures (Tin=30°-60° C.) with mesh size membrane 4 µm.

Loading Efficiency of Ranibizumab and Bevacizumab onto Crosslinked BSA NSs

For encapsulation of the Ranibizumab or bevacizumab inside crosslinked BSA NPs, Ranibizumab or bevacizumab was added to BSA solution prior the addition of desolvating phase. The rest of procedure was made exactly in the same manner detailed above. After crosslinking, the NCs were washed and the total ultrafiltrate was collected, lyophilized and reconstituted with 500 µl DDW.

Physicochemical Characterization

100 µl from each formulation was diluted in 1000 µl of water for HPLC, filtered via 0.2 µm PVDF filter and analyzed using the Malvern Zetasizer (Malvern Instruments, Malvern UK) to determine the zeta potential and particles diameter size.

SEM and EDS

Geometry, size and surface morphology of the spray-dried NCs (and encapsulated NSs) were observed by a High Resolution Scanning Electron Microscope (HR-SEM) with High stable Schottky Field Emission Source (Sirion, model: Quanta 200 FEI, Germany), 5 kV. Prior to imaging, the samples were dispersed onto carbon sticky tabs and coated with gold and palladium mixture for 90-120 sec. In case of primary NCs dispersed in water, the samples were highly diluted, then spattered on glass and left to evaporate overnight. Element analysis of the specimen was made by EDS (Energy Dispersive X-ray Spectroscopy), with X-MAX20 SDD Inca 450 EDS LN2 free detector.

The amine groups detected by the EDS can only originate from the presence of albumin nanocarriers inside the Nanoparticles since no other excipient in the formula do contain amine groups Table 8 summaries the physicochemical profile of two formulations which were prepared by protocol-2 (Nanoencapsulated Avastin with crosslinked bovine serum albumin (BSA); whereas Table 9 summaries the physicochemical profile of one formulation which was prepared by protocol-1 (Conjugation of Avastin to nanospheres' surface). Blank batch state for formulation without protein where Ab batch state for formulation loaded with protein.

TABLE 8

Size and zeta potential of BSA-NPs following Vivaspin washings

| Formulation batch | Ab present | Diameter of NSs (nm) | PDI | Zeta potential (mV) |
|---|---|---|---|---|
| Novastin-003 | Blank | 97.12 ± 1.097 | 0.251 | 45.8 ± 1.52 |
|  | Ab | 177.4 ± 3.161 | 0.083 | 47.9 ± 0.416 |
| Novastin-006 | Blank | 203.4 ± 2.178 | 0.124 | 49.9 ± 0.436 |
|  | Ab | 212.2 ± 2.139 | 0.112 | 51.9 ± 0.513 |

TABLE 9

Size and zeta potential of INPs following Vivaspin washings.

| Formulation batch | Diameter of NSs (nm) | PDI | Zeta potential (mV) | Ab concentration | % crosslinking |
|---|---|---|---|---|---|
| Novastin-005 | 69.62 ± 0.333 | 0.121 | 56.5 ± 6.43 |  |  |
|  | 70.09 ± 0.769 | 0.14 | 48.7 ± 0.208 | 8.486 | 95.8 |

Evaluation of free Ab in BSA-NP by gel electrophoresis (protocol-2) was carried out by using the following parameters: NuPAGE Novex Bis-Tris Mini Gels (Invitrogen), gradient 4-12%, denaturing sample but non reduced, MOPS Running buffer, coomassie Blue G-250 staining (limit detection 0.1 µg of protein). Electrophoresis was applied 15 days following batch formation.

As was evident from the results (results not shown), bands density was quantified to obtain Ab concentrations. No Ab was found in the formulations washings indicating that all the Ab have been encapsulated in the BSA-NPs. Only low release of the encapsulated Ab was obtained during the electrophoresis. No effective procedure to denature the NPs and liberate the Ab has yet been found.

In-Vitro Evaluation

Uptake in a-431 Cells of Primary HSA NSs

Figure 19A:
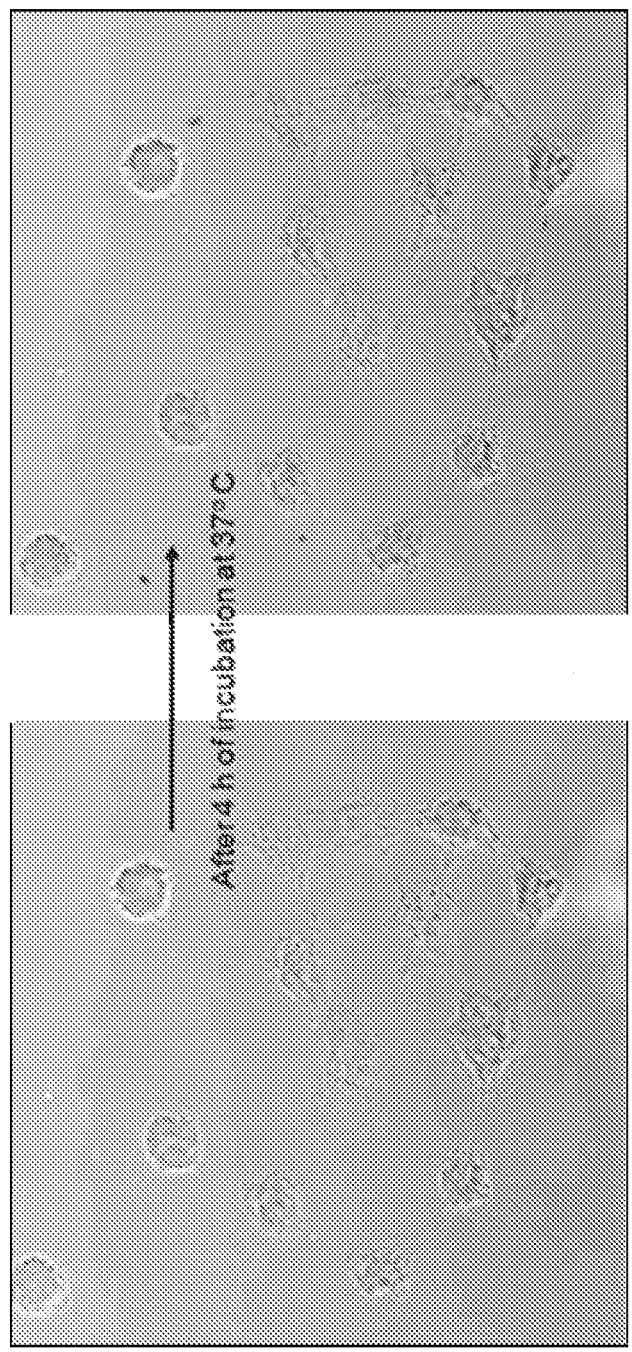
FIGS. 19A-19B show uptake of 2% FITC-labeled HSA NPs in A-431 cells using CLSM. Uptake after 4 h (FIG. 19A) and 22 h (FIG. 19B) of incubation at 37° C. NPs concentration is 2 mg/ml (1.5 ml per well).
Figure 19B:
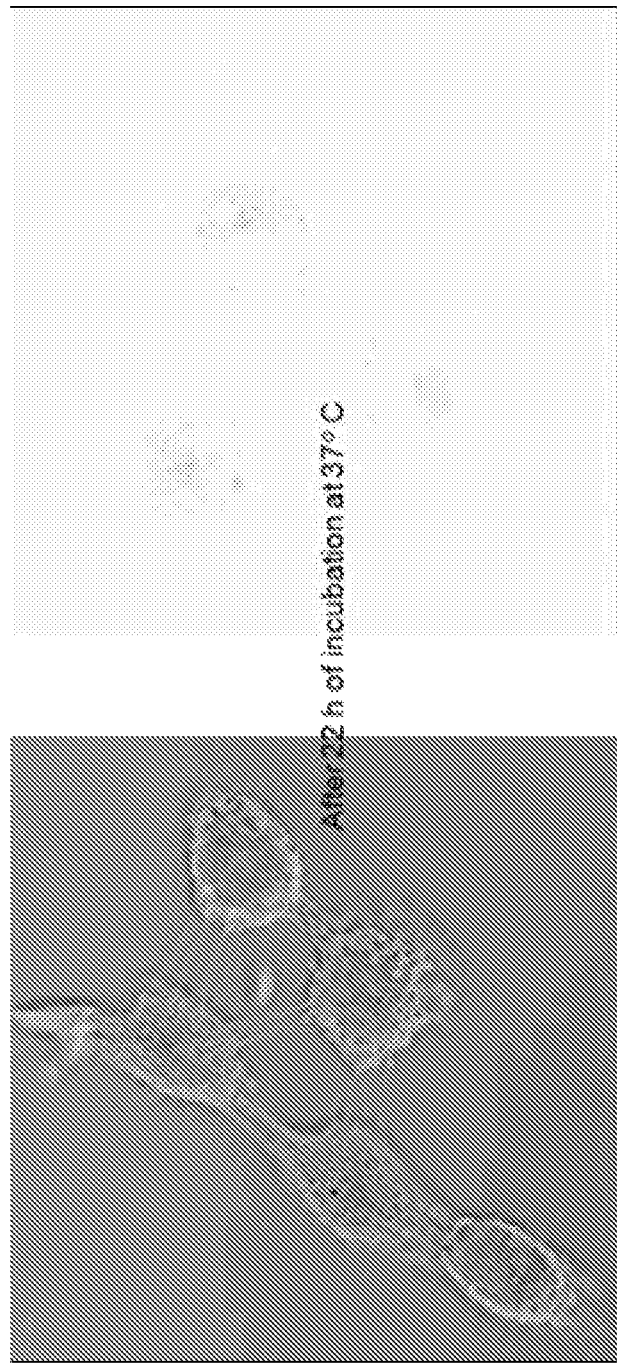

2% FITC-labeled crosslinked HSA NSs were incubated with A-431 cells (concentrations of 1 mg/ml and 2 mg/ml per well) at 37° C. over 4 h and 22 h. Based on Confocal laser scanning microscopy (CLSM), a high level of uptake was observed after just 4 h (for the two concentrations examined). After 22 h of incubation, no spots of NPs were detected outside the cells (FIGS. 19A-19B).

These findings substantiate the ability of HSA NSs to deliver loaded drug (e.g. siRNA) into target cells.

The invention claimed is:

1. A polymeric nanoparticle encapsulating a plurality of nanocarriers, wherein:
   said plurality of nanocarriers are in a form selected from the group consisting of nanocapsules and nanospheres;
   at least a portion of the plurality of nanocarriers comprises at least one active agent; and
   said nanoparticle is prepared by nanospraying and has an average diameter of between 400 and 950 nm.

2. The nanoparticle of claim 1, wherein the plurality of nanocarriers are obtainable by nanospraying.

3. The nanoparticle of claim 1, wherein a material of the nanoparticle and/or a material of the plurality of nanocarriers are cross-linked.

4. The nanoparticle of claim 1, wherein the plurality of nanocarriers further comprises a polycationic lipid being 1,2-dioleoyl-3-trimethylammonium-propane (DOTAP).

5. The nanoparticle of claim 1, being in a form of a nanocapsule or a nanosphere independent of the form of the plurality of nanocarriers.

6. The nanoparticle of claim 1, wherein said active agent is selected from the group consisting of a vitamin, a protein, an anti-oxidant, a nucleic acid, a short or long oligonucleotide, a siRNA, chemical derivatives of siRNA, a peptide, a polypeptide, a lipid, a carbohydrate, a hormone, an antibody, a monoclonal antibody, a vaccine, a prophylactic agent, a drug, a diagnostic agent, a contrasting agent, a nutraceutical agent, a small molecule, an electrolyte, an immunological agent, and combinations thereof.

7. The nanoparticle of claim 6, wherein the active agent is siRNA.

8. The nanoparticle of claim 6, wherein said active agent is hydrophobic and is selected from the group consisting of an analgesic agent; an anti-inflammatory agent; an enthelmintic agent; an anti-arrhythmic agent; an anti-bacterial agent; an anti-coagulant; an anti-depressant; an antidiabetic; an anti-epileptic; an anti-fungal agent; an anti-gout agent; an anti-hypertensive agent; an anti-malarial agent; an anti-migraine agent; an anti-muscarinic agent; an anti-neuroplastic agent; an immunosuppressant; an anti-protazoal agent; an anti-thyroid agent; an alixiolytic; a sedative; a hypnotic; a neuroleptic agent; a beta-blocker; a cardiac inotropic agent; a corticosteroid; a diuretic agent; an anti-Parkinsonian agent; a gastro-intestinal agent; an histamine H1-receptor antagonist; a lipid regulating agent; a nitrate; an anti-anginal agent; a nutritional agent; an HIV protease inhibitor; an opioid analgesic; a sex hormone; and a stimulant agent.

9. The nanoparticle of claim 1, having an outer surface associated with at least one targeting agent.

10. The nanoparticle of claim 9, wherein said at least one targeting agent is selected from the group consisting of a monoclonal antibody; a small molecule; hyaluronic acid; hyaluronan; tumor penetrating peptides; epidermal growth factor (EGF); transferrin; ferritin; Arginine-Glycine-Aspartic acid (RGD) peptide; epithelial cell adhesion molecule (EpCAM); intercellular adhesion molecule 1 (ICAM-1); carcinoembrionic antigen (CEA); vasoactive intestinal peptide; CA 15-3 antigen; MUC1 protein; CD20; CD33; integrins; lymphatic targeting moieties; aptamers; and oligosaccharides.

11. The nanoparticle of claim 10, wherein said monoclonal antibody is selected from the group consisting of trastuzumab; AMBLK8; cetuximab; Rituximab; ranibizumab; and bevacizumab.

12. The nanoparticle of claim 11, wherein said at least one targeting agent is selected from ranibizumab and bevacizumab.

13. The nanoparticle of claim 10, wherein said small molecule is selected from the group consisting of folic acid and folate.

14. The nanoparticle according to claim 1, wherein said active agent is contained within the at least a portion of the plurality of nanocarriers or associated with a region of an outer surface of the at least a portion of the plurality of nanocarriers.

15. The nanoparticle of claim 9, wherein said at least a portion of the plurality of nanocarriers has an outer surface associated with at least one further targeting agent.

16. The nanoparticle of claim 15, wherein said at least one targeting agent is identical to said at least one further targeting agent.

17. The nanoparticle of claim 15, wherein said at least one targeting agent is different from said at least one further targeting agent.

18. The nanoparticle of claim 1, wherein said at least one active agent is negatively or positively charged.

19. The nanoparticle of claim 18, wherein said active agent is negatively charged and the at least a portion of the plurality of nanocarriers further comprises a cationic lipid or a cell penetrating peptide.

20. The nanoparticle of claim 19, wherein said cationic lipid is selected from the group consisting of 1,2-dioleoyl-3-trimethylammonium-propane (DOTAP), stearylamine, and oleylamine.

21. The nanoparticle of claim 19, wherein said cell penetrating peptide is selected from the group consisting of HIV-TAT, penetratin, Gramicidin S, MSI-103, MSI-103-Arg, PGLa, PGLa-Arg, Magainin 2, Magainin-2-Arg, KIGAKI, BP100, MAP, MAP-Arg, SAP, PEP-1, transportan, and FP23.

22. A process for obtaining the nanoparticle of claim 1, the process comprising:
(a) obtaining at least one nanocarrier, said nanocarrier comprising at least one active agent; and
(b) encapsulating said at least one nanocarrier into said nanoparticle.

23. A nanospraying process for obtaining the nanoparticle of claim 1, the process comprising:
transporting through a screen having one or more orifices of a predetermined size a colloidal composition comprising a plurality of nanocarriers and a nanoparticle material in a liquid medium,
wherein:
said plurality of nanocarriers comprises at least one active agent,
said nanoparticle material is at least partially soluble in said liquid medium, and
the size of said orifices determines a size of the nanoparticles.

24. The nanoparticle of claim 1, wherein:
a material of the plurality of nanocarriers and the active agent are both hydrophilic or a material of the plurality of nanocarriers and the active agent are both hydrophobic; and
a material of the nanoparticle is hydrophilic or hydrophobic.

25. The nanoparticle of claim 24, wherein a hydrophobic material of the nanoparticle and/or the plurality of nanocarriers is selected from the group consisting of lactic acid, poly(D,L-lactic-co-glycolic acid) (PLGA), poly(D,L-lactic acid) (PLA), poly(c-caprolactone), poly(2-dimethylaminoethylmethacrylate) homopolymer, poly(2-dimethylaminoethylmethacrylate)-b-poly(ethyleneglycol)-α-methoxy-ω-methacrylate copolymers, polycyanoacrylates, polyanhydride polymers, and combinations thereof.

26. The nanoparticle of claim 24, wherein:
said material of the nanoparticle is hydrophobic, and
an outer surface of said nanoparticle is associated with at least one polyethylene glycol (PEG) moiety.

27. The nanoparticle of claim 24, wherein a hydrophilic material of the nanoparticle and/or the plurality of nanocarriers is selected from the group consisting of dextran, hylauronate, normal or cross-linked human serum albumin (HSA), normal or cross-linked bovine serum albumin (BSA), chitosan, shellac, collagen, gelatin, gum arabic, polyvinyl alcohol, cyclodextrin, and combinations thereof.

28. The nanoparticle of claim 27, wherein said active agent is hydrophilic and is selected from the group consisting of therapeutic peptides and proteins.

29. The nanoparticle of claim 27, wherein said active agent is hydrophilic and is selected from the group consisting of exenatide, insulin, growth hormone, triptorelin acetate, buserelin, and nafarelin.

* * * * *